US011578327B2

(12) United States Patent
Merico et al.

(10) Patent No.: US 11,578,327 B2
(45) Date of Patent: Feb. 14, 2023

(54) OLIGONUCLEOTIDE THERAPY FOR WILSON DISEASE

(71) Applicant: Deep Genomics Incorporated, Toronto (CA)

(72) Inventors: Daniele Merico, Toronto (CA); Erno Wienholds, Toronto (CA); Frank Schmitges, Princeton, NJ (US); Matthew O'Hara, Toronto (CA)

(73) Assignee: Deep Genomics Incorporated, Toronto (CA)

( * ) Notice: Subject to any disclaimer, the term of this patent is extended or adjusted under 35 U.S.C. 154(b) by 0 days.

(21) Appl. No.: 16/970,088

(22) PCT Filed: Feb. 14, 2019

(86) PCT No.: PCT/US2019/018076
§ 371 (c)(1),
(2) Date: Aug. 14, 2020

(87) PCT Pub. No.: WO2019/161105
PCT Pub. Date: Aug. 22, 2019

(65) Prior Publication Data
US 2021/0032629 A1 Feb. 4, 2021

Related U.S. Application Data

(60) Provisional application No. 62/630,565, filed on Feb. 14, 2018.

(51) Int. Cl.
*C12N 15/113* (2010.01)
*A61K 31/7088* (2006.01)
*A61P 43/00* (2006.01)

(52) U.S. Cl.
CPC ...... *C12N 15/1137* (2013.01); *C12N 2310/11* (2013.01); *C12N 2310/315* (2013.01); *C12N 2310/3525* (2013.01)

(58) Field of Classification Search
CPC ............ C12N 15/1137; C12N 2310/11; C12N 2310/33; C12N 2310/315; C12N 2310/3525; C12N 2320/33; A61K 31/7088
See application file for complete search history.

(56) References Cited

U.S. PATENT DOCUMENTS 3,687,808 A 8/1972 Merigan et al.
5,994,517 A 11/1999 Ts'o et al.
(Continued)

FOREIGN PATENT DOCUMENTS

CN 105986015 A * 10/2016
EP 1752536 A1 2/2007
(Continued)

OTHER PUBLICATIONS

Skerra, A. (Nucleic Acids Research, 1992 vol. 20:3551-3554).*
(Continued)

*Primary Examiner* — Terra C Gibbs
(74) *Attorney, Agent, or Firm* — Clark & Elbing LLP

(57) ABSTRACT

The present disclosure provides antisense oligonucleotides, compositions, and methods that target ATP7B exon 6 or a flanking intron, thereby modulating splicing of ATP7B pre-mRNA to increase the level of ATP7B mRNA molecules having exon 6, e.g., to provide a therapy for Wilson disease. The present disclosure provides an antisense oligonucleotide including a nucleobase sequence at least 70% complementary to an ATP7B target sequence in exon 6, a 5'-flanking intron, a 3'-flanking intron, or a combination of exon 6 and the 5'-flanking or 3'-flanking intron.

28 Claims, 5 Drawing Sheets
Specification includes a Sequence Listing.

(56) References Cited

U.S. PATENT DOCUMENTS

| | | | |
|---|---|---|---|
| 7,491,805 B2 | 2/2009 | Vargeese et al. | |
| 8,178,503 B2 | 5/2012 | Rigoutsos et al. | |
| 9,127,276 B2 | 9/2015 | Prakash et al. | |
| 9,714,421 B2 | 7/2017 | Prakash et al. | |
| 9,867,882 B2 | 1/2018 | Manoharan et al. | |
| 9,890,382 B2 | 2/2018 | Bentwich et al. | |
| 9,920,379 B2 | 3/2018 | Bentwich et al. | |
| 2004/0101854 A1* | 5/2004 | Bennett | C07H 21/04 435/6.14 |
| 2005/0244851 A1 | 11/2005 | Blume et al. | |
| 2007/0048756 A1 | 3/2007 | Mei et al. | |
| 2007/0050146 A1 | 3/2007 | Bentwich et al. | |
| 2012/0094374 A1 | 4/2012 | Bentwich et al. | |
| 2016/0257961 A1 | 9/2016 | Bradshaw et al. | |
| 2017/0151339 A1 | 6/2017 | White et al. | |
| 2018/0009837 A1 | 1/2018 | Crooke et al. | |
| 2018/0305689 A1 | 10/2018 | Saetrom et al. | |
| 2018/0326070 A1 | 11/2018 | Manoharan et al. | |
| 2019/0070213 A1 | 3/2019 | Aznarez et al. | |

FOREIGN PATENT DOCUMENTS

| | | | | |
|---|---|---|---|---|
| EP | 1783645 A1 | 5/2007 | | |
| JP | 2007-252277 A | 10/2007 | | |
| WO | WO-95/06714 A1 | 3/1995 | | |
| WO | WO-1995/008641 A1 | 3/1995 | | |
| WO | WO-2002/053728 A2 | 7/2002 | | |
| WO | WO-2004/035819 A2 | 4/2004 | | |
| WO | WO-2004052300 A2 * | 6/2004 | | C12N 15/1137 |
| WO | WO-2013105022 A2 * | 7/2013 | | A61P 35/00 |
| WO | WO-2015002978 A2 * | 1/2015 | | C12Q 1/701 |
| WO | WO-2015/188197 A2 | 12/2015 | | |
| WO | WO-2016/118726 A2 | 7/2016 | | |
| WO | WO-2017/100461 A1 | 6/2017 | | |
| WO | WO-2017/106283 A1 | 6/2017 | | |
| WO | WO-2017/222248 A1 | 12/2017 | | |

OTHER PUBLICATIONS

Havens et al., "Splice-switching antisense oligonucleotides as therapeutic drugs," Nucelic Acids Res. 44(14): 6549-6563 (2016).

International Search Report and Written Opinion for International Application No. PCT/US2019/018076, dated Jul. 30, 2019 (49 pages).

Sliedregt et al., "Design and Synthesis of Novel Amphiphilic Dendritic Galactosides for Selective Targeting of Liposomes to the Hepatic Asialoglycoprotein Receptor," J. Med. Chem. 42(4):609-618(1999).

Snyder et al., "Recent advances in the use of protein transduction domains for the delivery of peptides, proteins and nucleic acids invivo," Expert Opin Drug Deliv. 2(1):43-51 (2005) (10 pages).

Englisch et al., "Chemically Modified Oligonucleotides as Probes and Inhibitors," Angew Chem Int Ed. 30(6): 613-29 (1991) (17 pages).

Margarit et al., "Mutation analysis of Wilson disease in the Spanish population—identification of a prevalent substitution and eight novel mutations in the ATP7B gene," Clin Genet. 68(1):61-68 (2005).

Hua et al., "Antisense-mediated exon inclusion," Methods Mol Biol. 867: 307-23 (2012).

Loudianos et al., "Abnormal mRNA splicing resulting from consensus sequence splicing mutations of ATP7B," Hum Mutat. 20(4): 260-6 (2002).

Xu et al., "ATP7B antisense oligodeoxynucleotides increase the cisplatin sensitivity of human ovarian cancer cell line SKOV3ipl," Int J of Gynecol Cancer. 18(4): 718-722 (2007).

* cited by examiner

SEQUENCE LISTING

```
<160> NUMBER OF SEQ ID NOS: 170

<210> SEQ ID NO 1
<211> LENGTH: 85826
<212> TYPE: DNA
<213> ORGANISM: Homo sapiens

<400> SEQUENCE: 1
cacaaaacca cttttcctc ctgggcctcc aggcctgcca tgagagaggc tgccatgaag      60
gtctccgaca ttgcctggag acattttccc ccatggtctt caggattaac attaggctcc    120 ttgctactt tgaaaatttc tgcagccagc ttgaatttct cctaaaaaaa tgggtctttc     180
ttttctactg cattgtcagg ctgcaaattt tctgaacttt tatgctctgt tccgcttta     240 aaatggaatg cttttaagag cacccaagtc acttcttgaa ttctttgctg cttagaaatt    300
tcttacacca gataccctaa atcatctctt tcaagttcaa agttccacaa atctctaggg    360
caggggcaaa atgcctctag tacctttgct aaaacataag aggagtcacc tttctccagt    420
tcccaacaag ttcttcatct ccatctgaga ccacctcagc ctggatttcg ttgtccatat    480
cactatccgc attttgttca aagccattca acaagtctct aggatgttcc aaactttccc    540
acattttcct ggcttcttct gagccctcca aactgttcca gcctctgcct gttgcccagt    600
tccaaagtcg cttccacatt tttgggtatc tcttcagcag caccccactc tactggtact    660
aatttatggt accaagttca ttttcacgct gctgataaag acatactcga aactgggaac    720
aaaaataggt ttaattggat ttacagttcc acatggctat gaggcctcag aatcatggcg    780
ggaggcataa ggcacttctt acatggtggc agcaagagaa aaatcagaaa gaagcaaaag    840
cagaaacccc tgataaaccc catcagatct cgtgaactta ctcactatca cgagaatagc    900
atgggaaaga ttggccccca tgattcaatt acctcccct ggatccctcc cacaacatgt     960
gggcattctg ggagataaaa ttcaacttga ggtttgggtg gggtcacggc caaaccatat   1020
cacatagttt tcactgccca catgaaaaca tacaaattca tcagaaaagt aaattttgct   1080 tttttagat acagggtctc actctgtcac ccaggctgaa gtgcagtggt gcaatcatag    1140
caatcactgc agccccaaac tccttggctc aagcgatcct cctgcctcag actcctgaga   1200
agctggaact acaggtgcat gccaccacac ccagctaatt aaaaaaatgt tttttgtaga   1260
aatagggttt tgctatgttg cccaggctgg tctcaaactc ttggcctcaa gtaatcctcc   1320
tgccttggcc ttccaaagca ttgagattac aggcatgagc tgctgcacct ggccagaagt   1380
aaatatttta ttgatattta gttttgacat aaagttctca tgtgggattt cctattgtga   1440
acaaatcctc atttgttcct attgtgaaca atctcatgt gggatttcct actgtgtact    1500
tgaagaggta tttgactcta tttgaaatcc cacatgagca ctttatttca aagctgaaat   1560
aattggtcta aaataatttg gtctttatat tctttataca cctttatact cttaaaaatt   1620
ttactgagga tacaatagag cttttgttta catcagagtt tctcatcctt gacactactg   1680
acattttgga ccaaataatt atttgttgcg gaggttgtcc tatgtattat atttagtagc   1740
```

```
atctttggtc ttgacccact tagatgccag tagcaccctc ccaatcaaaa ttatcagttg    1800
ggcatggtgg ctcatgcctg taatcccaac attttgggag gctgaggtgg gaggattgct    1860
tgagcccagg agttcaaggc tgtagtaagc tatgatcatg ccactgcact ccagcctggg    1920
caacagagca agactcttat ctctaaaaaa aaaattaaaa aaaaaaagcc ctccagatat    1980
tgccaaatgc caaatgtctt gcgaagggca aaatcaccc ctggttgaga accagtggtt     2040
tacactgctt atatctacca atatttagca tattagaaat gaaaactaaa gaactttaaa    2100 cttttatga attcatttga aaataaaaat tctttcataa cacattaaca tattttatt      2160 aaaaactat cttttccaaa ccaaaaaaag aaatttagca agaagggtgc caatgattta    2220 cacttttgc aaatcttttt aatgtctggc ttaacgtgaa accagatagt ggctcctcct     2280
ttctgtttct gcattcaatc tagtgatatg ttgttttgt tgaagtatat gaagaaaatt     2340
caggctaact tagacatgta gtaggaaaag ggagtatatt ttaatatata ttgatcttat    2400
gtttaaaata tatttaactt ttcagctagt tacagatatt cttctctgat gctagaccac    2460
atttgacaag ttatgcagtt tcttaatgtc agttgcaata cagactctga aaccctatca    2520
atgacctttt cacactgtta attaaaatcc actatcactt agttttatcc gctatcactt    2580
ttgcacttat caacatagta aaataggcaa atattacatt aatgttatta taaaaacaga    2640
tttgttgagg atccattgaa gggccttggg acctgcatgg tccatggagc acaatttgag    2700
aaccactgcc ttaaaggatg aacagagtct gacaaaagtg gtaagattta tcatttattt    2760
aacatttgga atatatgaat tcataaaagc aacactacag aggacagttt gctttctcag    2820
gacactcttt caaaagctta tttaaaatgc agctgaccca tataatgtaa aggttttct     2880 ggcaattcct tcaaataatt taggtgggaa aattcatgtg acaagctttt caaactgaac    2940
tattaaacat ttaacttaaa agctgcataa taactaaagt taaacctgtc ctttaagtct    3000
ggttagtgag tttattttaaa cattataatg taaagcactg aggaatatta cgtatgacag    3060
ggaagaacca aaaggctctg ataacagact ttctcattca aaatgtttaa agtaatgatt    3120
acagaatttg aagtagagtg gacaaaaacg aagaagaaat gcctgaactt ttgaaagaat    3180
taggtatata ctgctattca ggaagctatg gtgttaatta taaattttca gcctgaacaa    3240
aaatatgtag gtggtaaaaa aactaggtag gtagaatata ctaggccttc tgttttatta    3300
gtggagggca aggcatttaa aatacagtag tactacaaca acaaaggtgg aaaaaagcct    3360
gggagttttt tcaccaaaat gttaacagtg gctatctccg gatggtagca ttcctggggt    3420 ttttttccttt tacttatcta tttttctaatt tttctagaag aaacagcata tacacgtaat    3480
acaaataaaa taatattta tgtaacttct tacatcataa aaattaaagt aacagattat     3540
caaaaagcag aggattcaac ataagcttta tatttaagtg acgtgttaac aatggcagtt    3600
ttggtgagtt taagagtaga aactaagatg agaaggaaga tccggtttct tctttaccga    3660
aaagagacat gatagattgg aaaatgtctc gtggctcaat cgtaaagaaa aataaggaat    3720
gaatatgaat aatttatgac agactaactg gagtgtgaaa gggaaaaaaa aagctgaagc    3780
agggaaggga actcgacccc tcggccaaca gtgaagcaga agaaaacgcg gtaaattgag    3840
tctttaagac ctagtctatt ccagtctata tagaagaccc ccaagaaaaa gaaagactgc    3900
tcattggcct gagaaattac cttagattca tgacaaggaa ggccatttgc ccgcaaaatt    3960
tagctacact ggacgggcaa gtaccctac agaagagaaa acgtctgtga gcccacacga    4020
ccggctgctc acctcaacaa cttgcacagg caccagctcc tttcgccggc cgccatcttc    4080
```

```
cgccgacccc cgaactcagg aaacgcttca cttctttt ccctattggc tcctgagaaa    4140
gcaagccgtg ctcgccccgc ccccacgggc caattgtgcg ttactattgg ttactggtag    4200
ccgcttccca cggccttcca gccaatagaa tatgccgagg cgtagactag tgttcggcgt    4260
ggcgcacacg gctcccgccc ccgtgggcgg gacagcagtg gggggttggg ctgaggaggg    4320
cgtggcctgt gattgacagc cgtcgctccc tccctcggcc acctccccca ctagaagccc    4380
ccgcctgggc gcctgcgccc ccgttccgg cccaaagccc gccgcccgtt ggaggccatt    4440
ggctggcctt tgcgcacagc ggatcgattt tccaggtgcg gagttcactc ttgccgcggt    4500
tgcttccttt gggacccacg gcgtccggca gccaggcgca gagtccgagg aggggcagc    4560 gcagagcgga cccgacgcgg cgccgccggg caccttcccc gcaggcggtg ggtgagccct    4620
gggagctgag tctgcggccc ggctctgcgc agctcacctg ccctcccgct cccgcacacg    4680
cgtgagatcc cagtacagtg tcggagcgca ccagcgcgag gtggccgaga ccgcggagga    4740
ggacaggcct ccgccctgcg gcgccggcac ggcagaggac attgtggcac tggcacggca    4800
gagaacactg tggcaccggc ggggccggca gttccagggt gggcactccc agccacctgg    4860
ggagtgggcg agggtccgag gcccactctc ccctcacgct ctcatcccg tgccccagg    4920 tcgggaggac ggcggcgcgc aactttgaat catccgtgtg aagagggctg cggcttcccc    4980
ggtcccaaat gaaggggcgg ttccggacc cctgtttgct ttagagccga gccgcgccga    5040
tgccctcaca ctctgcgcct cctctcccgg gactttaaca ccccgctctc ctccaccgac    5100
caggtgacct tttgctctga gccagatcag agaagaattc ggtgtccgtg cgggacgatg    5160
cctgagcagg agagacagat cacagccaga gaaggggcca gtcggaaagt gagttttgtt    5220 ccccgcgtc cgcgcagcgt gctcactccc accaggagga ttttcctccc cgcgttcggc    5280
gcttactcgc ccccaggggg tgcgcaggga aggccgagcc agaccccagc tccagggatg    5340
tcttggcgtg ggagaaaagg accctttaga aaaagtgtgc cgtcaactga tgtttgggag    5400
caatggaaaa ccccgcacct caaaattcat ctttatgctt ttaaggggtc tgatgctgga    5460
gagataaagt gagcgtcgag ttgctgtgct agagccctaa tggctcaaaa cgatgaagtt    5520
agttacctgg agaagttact cagagcctgg tgcttggacc agatatggta tatcgaggtc    5580
ctggaacttt tataactgtt ttaaattcat tttaattgta caagtaatac attaagacag    5640
tcttttaaaa atggaaacag cacagaaata ttttgcacaa aaagcagatc tatttttcag    5700 tcttttcta ttcacgtaca tatgtcttca ttcggcaaat atttattgag aactttctat    5760
gtttcaggca cacagtgttg agttgataca gtggttaaca agacatgtat ctatatgtaa    5820
tatgcacaca ttcagagaaa tctttaggtt tcatttgtat gaggtgttaa aattttgtt    5880 ttacctaaat gagatcactg tatgtgcatt ctctttttc agtttaacga tatatcttag    5940
agattgtttc actaactgtc taattcagtg caacctctgc acagtttgga cgcatcatag    6000
tttattcatg gtttcctagt ggtggacgtt ctgtttgcta ctttttttct ctctctcttg    6060
caagtgaaca tctttgtaca tgattttaa tgctgacact atttctttag gatagatact    6120
taggcctgga ttgctggaca gaacagtagg ctgtttcttt tccacagatt tctgaaacta    6180
attcactgac gttgctgggt gccctttagt agtgaattca tctaggctcc ggtgatacag    6240
aaatgaaaac taacggatta gtggacagac agagagaggc tggttagtag gtggtttgta    6300
gggtatgatg actatgcatt tgataggagt atgaagaaat gttgggaggg gtggcttgta    6360
cagaggagat ttcaacttcc tacagtgtcc ccacctagag aaagaaatca ttatccttcc    6420
aaatcaagct caagacctgc cacctccttg aaacgttctg taactgctcc tgcccatgtt    6480
```

```
gacctgtctt ctggaatcct ctgataatag cgttgaccag cgttattgag cttactgtgt    6540
gctgggcatt gtgttaggca ctcatatccc tctatgtgca ctctcgcgtt taatcctcac    6600
aaaaacccct tgatgtaggt attatatctt gttatcaaca tttattcaac aaattttttt    6660
gtgtgtacta tgtgctcaaa cacatagtac tcaaagtttt agacactggg gatttaggta    6720
ggaccgagac cttgccctca tgaatttaca tcctagttgg agataggaaa aaaaaaggga    6780
taaacaaatg tatagcgtag gagttaaggg aaaactttg tgccccgtga agcgtcactg     6840
aaaaatcaac tgacaaatgg cagattaata ggagagaagg catacacatt tactaacgtg    6900
ccgtgagagt cttacaacat aagatctcaa aggaaggcaa ggtggttgcc acaattatac    6960
tatcctgagg ttacagaaag tgtgggggct ctaagcttgg ccaaaaacag gttatggttg    7020
taaatcaggt tataggaggg agagaagagg agacctggct agcaaaggtg gtcttatgta    7080
gatgaaacct cacaggtagc agccctcagg gagaagaaat gtttcagacc ttgaaggtgc    7140
caaattcagc taatctcacc cagatccaga caaggaaggg ccctctgaga aaaactggct    7200
gcgtcaatgg aggttctcaa cagatgctca tctccctcac agtaggacta cttttgtctg    7260
taggccctct gaacggccat ctcaaaatat ttccaataag tctgttttga ggtgaaatgt    7320
tttagtttcc ttcaatagct ttatttcagg tactagtaag tactatgaag aaaataaagc    7380
agtttgggtc caggagttca agaccagcct ggcagcatat caagacatcg tttatacaaa    7440
aaaaaaagaa aaattagctg gcataatgg tgtgtgcctg tcgaaccagc tactcgggag     7500
gctgaggcag gaggatggct tgagcccagg agtttgaggc tacagtgagt tgtgatccca    7560
ccactgcact tcagcctgag tgataaagca agatcctgtc tcaaaaaaaa agaaaagaaa    7620
agaaagcaga ataagggaat aagataggga ttgacatggg tggagaggaa gatgctgttt    7680
taagtaggtg gtcagggaat gatttctctt ggaaggtagg atttgagtag agacctgaat    7740
gattcagatt tcagagaagt agcctaggtt gagaaaccat aaagtgtgag agtcctacgg    7800
cagtcatgtg ataagaagaa atatatactt ggtcttgtcc caagttcctg acatagagct    7860
tcttaaaccg ttgtaatttc ctgagagatg gtgataagag catcttttgt tattcataac    7920
aagtctcttt caccccctacc tgagtttctg ttaatgagag ggctcttgat aggcccctag    7980
atagcttcag gatggagact gattgccaga agaaccaacc atgtgattag gggattcgaa    8040
tgttcagccc cgtgctccaa cctctggaga ttgtgccaat caccagtgga caatgatcta    8100
atcagtgatg ccggcagaat agagcttct ttaaattttt atttattag ttttttgaga      8160 ggtagtctca ctctgttgct aggctggagt gcagtggcgg gatctcggtt cactgcaacc    8220
tgtgcctccc gggctcaagt gattctccgg cctcagcctc ctgagtagct gggattacag    8280
gcgcacgcca ccacacccag ctaattttg tatttttagt ggagacgggg tttcaccatg     8340
ttggtcaggg tcatctctat ctcttgatct cgtgatccgc ccacctcggc ctcccaaagt    8400
gttggaatta caggcgtgag ccactgtgc ctggcctttt tttttttaac caatgcagtg     8460
gatcacaaat agagctttct taaaaccct aaatgatggg ttttggagag cttcctgtta     8520
gtgaacacat caaggtgctg ggaaggtggt tcctggaaag gatatggaag ctcctggaaa    8580
cctccattcc catattttgc cctatctttt ccatgtggtg gtttcttagc tgtatttgt     8640 ataataaact ggtgatatta ataaagtgc tttcctaagt tctgcgagct gttctagcaa     8700
attacccaac ctgaggaggt aattgtagga acctcctgac tttacagttg gtcaggagta    8760
cagatggccc agacccagcg actggcatgt gaagtgtggg cattcttgtg gtcttgtggg    8820
```

-continued

```
cctgagccct tacctgtggg gtccgtgcta actccagatg gttggtgtcg gaattgaatt    8880
gaattgtagg gcacccagtt agtgtctgga gagagagcat tggttggtgt gaagaaaaac    8940
cccacacatt tggtgtcaga agtgtcgtga gtggaaacag tacagaagac atgatgttag    9000
agtttgggga acaataggaa agccagagtg gctgtggcag agggaaggag tgggagtgat    9060
agaacaggag atcagagttc atcattgctt tacagatggg gaaactgagc cagacacaag    9120
ttaagtaact tgcccgatgt accttgctta aagaggcag atctaggatt gagtcctagc    9180
caggcctgcc tgactttctc agcgattttt tattgtcaaa acttacttga cacttggtca    9240
taccacctgg tatgattatt taatgaatat agcttttatt tgcaactctg tgcttcttga    9300
aatgggaacc gggtttttac cgtttaaaaa actatttccc acatgtaggt gcaccacagt    9360
tgttcttgaa tgaatggatt ctcgacatga tttctccaca ttgttttctc ttcagaggcc    9420
tctctgtggg gcagcagtga cctggtcatt cagccttcag tccacaaaca ttatggagca    9480
ctttctgttt gcctggtact gggccaagca gggggatgca tagatgaaga gaggtcagcc    9540
cctgtgctgg atgcatgctg ggacagagct gtctacatgg tacagcaccc acagaagggg    9600
cagaaaaatt ccttcagtgg gaggtggtgc tcgagtgggt ctttcaggaa gagcaggcat    9660
tgattgggca cacaggagca tggagagaag ggcattgaag gcagagacca gcatgtataa    9720
aggtccagag gactggaaat ggaaagaggc atttagggga ctgtgagggg cgtggcaagg    9780
ctggaagagt ggaaggctgg aaggtctgtg gaagaccctg tttatcaggc taggagtttg    9840
gactttaccc tacaggaaaa cagcgtaagt cactcctgca aggcagaggg tgaactgggc    9900
agggagctgc gggagaccag ctagagactg ttggaaatga tcgtcccat ccagaccaaa    9960 ggtggctgaa aagcctgaaa aagaactgta agttgggtct tctaccctta ttctttatgg    10020
aattgtcttc tcagtagaga aactaggcta tccaaactca actgtcctga gtattagagg    10080
ccagtggtcg ttttagcagc aacagagtgc agttggtacc tacggagcag ggtaataaac    10140
taagcaagtg acagagatgg atttaagtgc ttctttacgt gacacacatt ttcttctcaa    10200
tgggagggat ggagatggcc cagtaacatg aacactgctc actgatgcca tagcatagat    10260
atcgaggaag tatccgtgtt cagtgctgag agccccgaac aaagatttac ccacgaattt    10320
attaacagca agccagtcat tagcattgtt tctatagata ttcattaact aaaagtatcc    10380
cttatgggaa aggaagggat gggccgaaat aaagggtgg gtctggctag ttatctgcag    10440
caggaacatg cccttaaggc acagatcgct catgctgttt gtggtttaag gacaccttta    10500
agcagttttc tgccctgggc gggccaggtg ttccttgcct tcattccagt aaacccacaa    10560
ccttccagcg tgggcgttac ggccatcatg aacatttcac agtgctgcag agattttgtt    10620
tatggtcagt tttggggcca gtttatggct agattttggg gggcctgttc ccaacagagg    10680
cacaaaggga ctaagataga aattggtacc aagaagtgga gtgttggtat aacagatccc    10740
tgaaaatgca gagttggctt tggaactggg taaagggtag aggctggaag agtttggagg    10800
tacatgctgg aaaaagccta gatagtgata aactaagcat taaggattat tttggtgagg    10860
gcttagaaga acagagctgt agacagaacc tgaatcttct tagagattac ttaagtggtc    10920
atgatcagaa tgttggtgga agtatggaca gcaaggtca ttttgatgag gtcttagaca    10980
gaaatgagga atattttatt gggaactaga gaaaagccca ttctgttttt atttataaaa    11040 tgcagagaa cgtgggtcag ttgtgtctgt gccctaatgc tttgtggagg atagatgatg    11100
aactagatga agagtgatga actaggatat ttggtggaaa aaatatctaa gcagagtgtg    11160
cagggtgctg catggcttct cttgattgct tataagaaaa tgcaagaaga aaacaaatta    11220
```

```
aagacagaaa ttataatcaa aagggaagca gaacttagaa agatttggaa aattttcagc   11280
ctggctagat cataaagaat aaaaaggctg ctgggaagaa tgaccttaaa gggatttggg   11340
aggtctttgg gactgctcct cctgtcacag gcccagagtg cctggaccat gagggcagga   11400
gggagaggac catacccgc cagcaggtct atgggtctag ttgcccaggg ccacctcgag    11460
cctctgcttc ctgcattctg cggtgctcct tggccacccc aggtgcggct caggtgtggc   11520
ttgggctgct gctctggaag gtgcaggcta taaaccttgg tgtccatgtg gtgctaactg   11580
cagctgagca gagttcaaga gctgtggagt gtggctactt tcatctagat ttccgaggat   11640
gtcttggaga acccggggcc caggcagaaa acgtctatgg ggaagagcca ccacagagtg   11700
cccccactag ggcagtacca tcagtcatga attgggcagt gccagactac atagttcagg   11760
gctccatcta gggggaatga gggaaagact ttgtaagtgt tcagggaagc aaaacaaaga   11820
gaataattga ttggttaaag tagaaaggcc tagttataag ctgtcatgag attggagaaa   11880
aaaataaaaa taaggaataa aaaagaccct agttagagtt tagttggtgg ttcctgattg   11940
atgaagtctc tagttagaga tagttaatgg attgtgattg gttaagctaa gctttgtttt   12000
actgtttata ttgagtttggg tttggtttgc ttacatagga acctgaaatg ttggagtcat   12060
ctcagcctaa ttgcttcctg attaatgatt tgttaacaca agttaggatg caactccatc   12120
ttcctgatac tcatggcct aaaacagttg ttggtgctgc agccgtgtat ttcaagttgc    12180
acatagctga ataagggaa aggcaaggat aatcctgctc tctctttttt tttgagacag    12240
agtcttgctc tgtcagccag gctggagtgc agtggcacga ttttggctca ctgcaacctc   12300
cctctgccgg gctaaggaaa ctcttctgcc tcagcctccc gagtagctgg gtttacaggc   12360
atgtgccacc atgcccggct aattttttgta atttttttta gtagagacgg ggtttcacca   12420
tgttggccag gctggtcttg aactcctgac ctcaggtaat ccgcccccct cggcctccca   12480
aagtgctgga ttacaggtgt gagccaccgc gcccggccag tcctgctgtc ttttagggag   12540
cctgcttagg agccctgaca aacaactttg ccttatattc cattggctag aactttggcc   12600
agttttcaac atcttaaaat gggaagattt tactatgtaa aactccagct atccaccttc   12660
tctcggaagc tctggtgaca ccaggccttt tgacaacagt tggctggagc tgaggaacag   12720
ctgcctgctc caggtggggc atgagctcct cctgtggccg caagcccgc atggcctgtt    12780 ctgctcattt aagtcactgc ctacttgtga cagtacaggc aaacctttgc tttattgccc   12840
ttttgcagat gctgtatttt ttttttttac cagttgaagg tttgtggcaa ccctgcactg   12900
agcaagtcta ctgacgccat ttgtgtaaca gcatatactc acttcatgcc acattttggt   12960
aattctcaca atatttcaga ttttttcatta ttattatatc tgttacggtg atctgtgatc   13020
agtgctcttt gatgctactg ttataatcat cttggggccc gtgtaagatg gcaaagttaa   13080
tctataaatg tgtacattct gactgctcca ctgactccag cagttcatgt ctctgtctct   13140
ccctccctct caggtctccc tatttcctaa gacacaacaa tattaaaatt aggccaatta   13200
ataaccctac aatggattct aagtgttcaa gtgaaagagt ccactccctt taaatcaaaa   13260
gctagaaatg attaagctta gtgaggaagg cttgtcaaaa gctgagatag ctgaaacct    13320 aggcctctgg tgccaaacag ttagcaaagt ttttaatgca aaggtaaagt ccttgaagga   13380
aagtaagtac tactctagtg aacagataaa tgataagaaa gcaaaacagc cttactgctg   13440
atatggagaa agttttagtg atttgaacat aagatcaaac cagacacaac attctcttaa   13500
gccaaagcct agtccagagc aaggtcctca gcattgaagc aaggccttcc actagcagaa   13560
```

```
agaccatgac ttactgacag ctcagatgat tgttagcatt tttttgccat aacatatttt   13620
aaaattaaag tatatgtatt tttttaggca taatgctatt gcacacttga tagactatag   13680
tgtaaacata acttttatat gcacaaggaa accaaaacct ttgtgtcact cacgttatta   13740
ggatatttgc tttattgtga tgatctagaa ccaaacccat ggatatctct gagagatgcc   13800
tgtatttgag cttagatccc tggcttgaag ggataaatga atgagtaagt gagggaggag   13860
ggagccagct tttgcatgag gcttgctccc ttcccctccc ctcccctccc ctctcccctc   13920
gcctccctgc ccctcttgtt tcacaggttc tctgttgctc aggttggaat gcagtggcag   13980
gctcactgca gcctggatct cctcgggctc aggtgatcct atcacctcag cttctcgagt   14040
agttgggact gcaggcatgt gccaccatgc ccagataatt aaaaacattt ttttttttag   14100
agacacggtt tcaccatgtt gcccaagctg gttttaaact cctgggctca agtgatcctc   14160
ccatttcagc ctctcaaagt gctaggatta caggtgttag cccccacgcc tggccctgaa   14220
tgttgagtat tgtcggaaag tttagcagtc cttttacagc aagcacattt gtaagttgtt   14280
tttgcttggc attctttgtc attcatttaa caaatgctta ttgagaaatt ctttaagtgt   14340
caagcactgt tttagacctt ggaataaagc agtgactgaa caaaatagat gtgaagaggc   14400
tgtgtgtggt ggttcagacc tctaatccca gcactttggg aggccaaagt aggcggattg   14460
cttgagctca ggagttcgag gccagcctgg ataacatagt gaaacccctg tctctactaa   14520
ataaataaat aaataagcaa gctgggcatc gtggcacgca cctgtagccc caggtacttg   14580
ggaggctgag atgggaggat cacttgagcc agggaggcgg aggctgcagt gagccaagat   14640
catgccactg cactccagct tgggtgacag agtgaaaccc tgtccttaaa aaaaaaaatg   14700
tgaaggattc ctgcacttgt gaaacttata tcctaactgg ggagatagtt gttaaaaaga   14760
gtaagtaaaa gatgtattat tgcatttggt ggtgattgag aattctcaag aaaaataaga   14820
cagggaagga tgatagggaa ttgggagtgt atgaaattta gatgggatca tttgggggaa   14880
atcattgaga agttgacgtt tgagcaaaga tttcatggag gtgaggaagt gagccctttg   14940
gatatgggat gttggaggga ggtatttcta agctagtaga cagttccgga ggcaggtgta   15000
tgctttgctt acctaaggaa cagcaagatc agaatgactg tttcagaatg agtaaggggc   15060
caggagtgtg aggataagtt ggaaggtaat gggagggctg caactgtata gtcttacagg   15120
tcatcattgt aaggatttta ggttttatta agcacatggg aacccctag aggcatttta    15180
gaggaatgac atcttgtgac ttcctcttat aggtattctg acttttgtgt tgagaataga   15240
ctttaggggc taagagcaga agccaggagg tcgcttagga gattctaagc aatagtgcag   15300
gtgagatgag ctggtggctt ggaccagggt tcttgtggat gtgttgaagt cattagatgc   15360
tggatgcatt ttgttggtgg aactaacagg atttgctaaa catttacatg tgggtttgaa   15420
agaagatgat tcttttttac ttttaatttt taaattcatt ttaattatta ttttgagac    15480
agaatctcac actgtcaccc agggtagagt gcagtggtcc aatcacagat cgctgcaacc   15540
tccacctcct gggctcaagt gatcctccca cctcagcctt ctgagtagct gggactacaa   15600
gtgtgcacca ccatgcccag ctaatttttt atttttttgaa gagatggtgt ctcactatgt   15660
tgcccaagct gttctgaaac atctgggctc aagtggtcct cctgccttgg ccttccaaag   15720
tgctgggatt acaggcatga gcccctgcac ctggatgaga ttattcttat caaagaggga   15780
tccaggattt tttcctgggc aagtggaggg aaggagttgt atttactaag gtggggaaga   15840
ctgtgggagc agcaggggaa gggcagaatg ttgagagctc tgtttagac aagttaagtt     15900
tgcgatgcat atgaaacacc gaggagatgg tgatgaggca tttgggtctg taagtataga   15960
```

```
gttgggaatt gtaggctata ggtggtgata tagtctgaat gttaatgtcc ctgccaaatt   16020
catatgttgg aacctaaccc ccaaggtggt ggtattagga ggtgaggact ttaggaggtg   16080
atttggccat gagggctctg ccttctcgaa tgggattagt gcccttataa aagaggcttg   16140
agggagccac tttgctcttc tgccatttga ggatgcagca gcaaggcacc atctgtgaag   16200
caaagaacag ccttcaccgg atactgaatc tgctggctcc ttgatctggg acttcccagg   16260
ttcctgaact gtgagcaata aattttgtt gcttataaat tacccagtct aaggtatttt   16320
gtgatagcag cctgagtgag ctaagaaagg tatacttctc ctggcctgga tgagtgtaca   16380
aggaatgagt agagatggaa gaggtccaag ggctgagctg ggggccactg cagcacttgg   16440
aggtttgggg acttggaggc tctggtgaaa gactctgagt aggagctgtt ggtgggaagg   16500
ataggaggaa aatcaggagg tggggcaact tggaggctga gcttggagac aaggactggt   16560
caccttgggc agtgtgtcac tggctgagag taagtatggg ggtgggcact ggggacctga   16620
ggagccagag aggggatagg accactgtct cggagagcga agggtgagcg gactaggggg   16680
tagttggact gccaggtggc agcacgggtc ctcccgcagt tcgtggtgct gaatcagagt   16740
gtgggcagcc agcctggatg tgcgttctgt cacattcttg ttgagctgct agaggacagg   16800
cgtgaagcca gtggaactg agagtaaagc cgtgttggag ttttgcagga aggtgccaga   16860
tgatgagggc agccagcgaa gtcgaaggtg catggaatga actgtgaaat ggaaacattg   16920
gcttttactt ttcgataatc ccattgtttc tctttttggc catcccatct cttcgtaatt   16980
tagaactatc ataatcgttt ttcactcaag actgttcagc caagtgcagt ttatttaaga   17040
gcactccttc agtgagctta cttaggtatg tgtgtgtttg tgcctgtctc ctgttaataa   17100
gctgatatga aagtcctgct gagctagttg tttcagtctt ggagatcagc agcgatatgg   17160
ggaggagaag ccaagcctct gttaaagccc accagtcctt ccctcccccg ctcccagcac   17220
ctagtgtttg aggaattcag actttgaata ctgctctttg ctactgttct tctctcctaa   17280
cttgccagta aacttccaag ggcagtatgt gtcttgtgct cctctcctgg tcttctgttg   17340
tgcatacact taaatacggc tctcaggctg tgaataatct gctttggtta acactcccct   17400
ctgttctgaa ggctgggctg ctagagccct gactgttggg ggctgtgctg tttgcagtgc   17460
tcatgttctc ttcttgggaa cccaacatat gcagctttaa tgtcaggctc tgccctcctg   17520
tcctgtcaca ggatccggga ctcctctccc catcttggga gggatggcct ggggatttcg   17580
tctgggaagc cctgcccagt gtgagcctct agctggactg agcaggtaat gtttgtgagt   17640
gctgaaatat tttaaccaga tgtccctcct ccaaagagcc ctttgtcctg gaggttcatg   17700
gaaacatgag ctgcccatct gcctttgggc ccaggcttct caggttgcaa caagattgtt   17760
taggacacca aagagatatt tattttata caggaaaaat ccacagactg ggaaggcgaa   17820
taggaggtaa agaagatgaa ttttcttctg gaaaatggct cgtgaaattt gtacatatgg   17880
aagacagaat aatctagtgc aaggaaatcc ttgaagacct agaagaaata tgtgagggac   17940
tgatagagtt tgcccttgtg ttgtggtaag ggggacaaaa agtaccatga aattctaggt   18000
agaaagcaca ttctgagcag tatataattg aactcattta tttaaatatg gttaaatata   18060
cttattcaaa tgtaaatatg taaatattta actgcttaaa tatacttatt taatgtctga   18120
tattgttcat caccatgtta ggtctgtggg cagctaagat atgagatcct tgtgttccag   18180
gatctgacca cgtttcccaa agtgagcaca tgcccatagg catcagtaac aagtgtggac   18240
tgagctgact gcagcctcgg tggacagaga agacttgtcc tccagcagtg ttacaggctg   18300
```

```
accacctgct ggcaccctga tgttgacatt agtgatgctg gaattcagat aagggagaga    18360
gctgctagca ggattccaca gagaggcagg acttaaagga taagaaggat tagatggtgc    18420
cgggaagggg aggagcaggg aagccagggt caggtgtgag gaaagggaa ggtgctagaa     18480 agaggagttt ggacttaata ctgtagccta ggaaggtggc ccatgccttg gctgttccac    18540
acgtctctta gattctatgg gagcaaagga gaagccactg tgtttacccc agacttgcct    18600
tcttcccacc ctccccgctc atcttggtgt actcatcacc atgtgctcaa tctgcgaaac    18660
tggaaatggc attgtcatcc tcaggccccc acttttgtc acctgctgtg atccagcagt     18720
cactgagttg ggaggcctcc tcgtttgttt aatcgtattc tactattaaa ttttctgccc    18780
cttgtaatcc ctcctctcct gggtcttcat tcttgtttct gcccaaactg tttccagatc    18840
acaaatatga ttctgtgagt tctctcctca gaaactcctg gtgattctac accacccaca    18900
ggacaaagtc tagactctgc cctttctaac ctggccccag cccccttttc tggctgtctt    18960
ctgggtctga gccaccatct agaaatggtt tgaatggtga agtatttcaa tttcatggag    19020
ctaacagaat agattattta aaagcatgtg ggacatatga tcccaacata ttttccttat    19080
tagctattca taggcacagc acagaagaag catttatatt tataatgatc tcatgtcacc    19140
aaggaaaagt taaaatatgt tcaataactc actttaaaag gcagcggaaa aatagatgtc    19200
acttatgggg aatattttca cccagaatga caaaattttt aaaaaatcta atgctcaaag    19260
cgatgagctt cagttacctg gaaaatctac ttctgatgcc ccataaatga aatgtcaggt    19320
ggtcagcagg gcatgtgagg ctcctgatag atcctttcag gaagggagag acatagataa    19380
gcaagacctg aagaatcact agaaagcaat cacagatgca cctgatgtat ttacatgggc    19440
tcccatagag gcagctgcac agccccacag tgctggcctc tggcagggag gctagggttg    19500
gggctcaagg cctttagcat caaatatacc tttccttga tgaaaatggg tttgaatgac      19560
atttcttgga aattgaggca ggttctttgt ttttggctg agcacttagg agataagaaa      19620
caaacccaga cacattttgg aggagttggt tgctcagcgt gtgctttaga agtgatagca    19680
accgccacaa gtgtggtaag aagcagcagg ataaagcagg cacgaagggg ctttggtgca    19740
tggaccagcc ttggtgttgc cttccctcaa agagaacaga tctctcagtc aggagttctt    19800
ggggcaggga tgacagtgtt aatgggggag gaagcgtcac tgtgggcaac ctatgaggag    19860
gcagccttca gtgaccttgg gcatgtgttc tgagtgccct cactgggtgc acacttagt     19920 gaccccctgc tggtacattc tgctgtgaag aataacacgg agagacagag tgatcatttt    19980
accctgaatt caattccaca ctcacttgca gcaggaggta tggctggaat tagtggctgt    20040
ggtggagctg ttcctgccat gggggatgtg gtctctcctt ctggtccccg agtggtgggg    20100
tgggaatgga ggcagcgctg cccgacagag caggctgctg ctggaattac cacagtgtcg    20160
tgtgtctcct cctattaatc cccatgtgga acagcaggta gcctgagaag cctgaattgt    20220
gccttagttc ctggccgtgg tgctgcttaa acagatgagc cttgttagcc agtttgtgca    20280
gtcagttctt actgaagtca agccttggt ccaagggaaa acaaagctac aggaaacatg      20340
gaactttctt acaccttctt gaaaatacaa gtcatgttgc ctaggaaata cttctctcac    20400
caagtattct gcacgctgcc aacattggag ctgtggaaga ggcagctgaa gcaattccaa    20460
gaaagtgcta gcagtttggt aataaaagga agtggcatat ctctcctgcc tctagactgg    20520
gtttctagga gtgcacatgg ccaaaaggaa actgctgcac tctggcaagt gattacatgt    20580
tgtgctcatg gacaccttgg ccgggtgtcc agtgtgcact gggtgagggt gtgcatgggc    20640
tgtgtgcaaa gatctgcagt gctgcacaca gtgtgttgag tgagagggtg ccaagtgctg    20700
```

```
ggacggttgt agataaacaa aagcaaatag gtgcagtact gtgcagcctg cccaagttcc    20760
caaagcttgc tgccaggctg aagactgctg gcagcctctc ctgggctggg tcaggagtag    20820
aagggtgtct tccccttgct aattaggagg acacttctaa agcatttctc tctaacacaa    20880
ccaaatagtc tgctgaaggt gaactgcttt agtgaggagg gaagccgtgg ccgtgaactc    20940
agcgatagag aaagccaggg gtgatgtgcc ccagagcccc gagcagtcct tcctggcaac    21000
tctgagtgac caacatgtga ccctgctgtc tgtccacaag cagtggtcct ttaggaagag    21060
ccctggggtt aggcattcag ccaggccagt gtctactgtg gaggaaggca ctccaccgtc    21120
agaggaagga gaatttccac agagagtttt gaatggaacc tgggaaatga gttccagtca    21180
ggtcagtgca attgcagatg ggctaaaaag cctggaaggg cctggaccca ttttaaagat    21240
ggaggtttct ctccatgtct cttgtgtggg atattgggga gaggtctggg gagcggaatg    21300
agagtgtgaa tgtagcacct ggcaggagtc aagctgatta attacaccat ggcttggaag    21360
tttgggtttt gttgcttttt attttcagaa tattttgtaa gactctatga agcaaaagtt    21420
ttccacaatg caagtcaaac aaaaatgaat ccttccttct ttttactaat atgttttata    21480
gtgtatacct tattttgtta atctgtacat tttaactaaa cattttgaaa atgctgcaaa    21540
atgaagttcc ttttcttaag caagttgaag ttttgttact ccaaaggtta ggtcatgtcc    21600
aaaagtaaga cagtataacg ttttgtaaaa atggtgcctt ttagcagcat ttctgagcag    21660
actggtggtg tgtacagggt cttcttcatt gacctagtca gacgaaaata aaaacaact    21720 tttgaaggca tttactagtt agatacaaag gaaggtttca taagtacttt gcttcctcta    21780
agacttattt ttgtgctgtt cattggttaa agtcccaaag actaaggaa attttgtgaa    21840 aagaactttc aaatgtgcta tgcaagagat ttacatacgt tgaaatcaca gggtacttgg    21900
atattgaaga cagaaactcc ttttgagtat ttaaagattc tgcattttgc tatcaggttt    21960
ttaaccaagg atataactat gctcggaggt atttatttta aaatattaaa agtgttttt    22020 ggtgttctga atttgtggaa atttccaaga gactccttta aagttttttc ctaggcaaat    22080
ttaaaaatat gaaatgtaga attattcagt ggctgcccgt ttgggtagct tctacacaga    22140
ggttcgagtg gttttagggg agggaagtga ggtgatagat acaattttaa ttactttgtt    22200
ttctaaagta gttttataaa tttcattta tgtctcttta aactgtatta agccagtagc    22260
taaactaatg tgttaaatca cttagaattt taaagagtga cagagcgttt aatcttttaa    22320 tcagccttt catatgttgc cggtttatac aatatacggt gaacatttat acttttagcc    22380
atgtgtttaa aatagtgaaa tactaaatat gttggggtga aaatgcttga ggcatttta    22440 aaaaatgtcc aaactgttac tttacaattt ccagcctata tctgaagttt tgagatatga    22500
cgtgtgctgg tgattttaa ggccagcacc aatctgtgac tagtggggcg acctgaagct    22560
gactagggga gcctcttcag aaaggagggc tggggaagag gccttggtgg agggggatctg    22620 agtgcagacc caacacaagt tgtgggacct gggcaggtga gtcttggaca ctctccttta    22680
gattcttcat tgcaaagtgg atgataaatc ctgcctcata tgattgtgaa agcactttgt    22740
agattatcat gcaaatgcaa aatagtgtta cttctgccaa aattatgctt tttcagaaga    22800
atttccaact ctgagatatg tttgatgtgt tgtctgaagg tctggacagg actgtgataa    22860
cccagtaatc tatctgagca cagttgcaac tctattttc ctttgtttgt tttttctaa    22920 gttttttatt ttgggacatg gtctcttgct gatgccgagg ctggagtgca gtggcatgat    22980
catggctcat agcaccctcg accttccggg ttcaaatgat tttcctgcct cagccccctg    23040
```

```
agtagctgcc accacaggtg catgccacca tttccagttt ctctttattt gtagagatgt    23100
ggtctcccta tgttgcccag gctggtctca aactcctggg ctcaaatgat cctcctgcct    23160 cccctccca aagtgctggg attatagatg tgagccaccg tgcctggcag ctctattttt    23220
tctaaagctc tgattataaa agtaacatat actctatata aaaacaaat ttacgatgga    23280 acgaggagaa tacaaaaaag tataaagaaa aagcagtcgt tttcccaaca aatatgaatg    23340
tgtatacgtg tatgtatgtt tatgtttaca taatgtatat ttttaaaata aatatgggat    23400
caaattatac atactatctt atactttgca tttcttactg aatattttgt ggacatttct    23460
gtatgtcaat atatatgtaa atctgtatta tcttttttt tttttttttt ttttgagac    23520 agagtcttgc tctgtcatcc aggctataga gtgcagtggc gtaatcttgg ctcactgcaa    23580
cctccatctc ctgggttcaa gtgattctcc tgcctcagcc tccagagtag ctgggactac    23640
aggcacctga caccataccr agctaattt tgtgttttta gtagagatga ggtttcccca    23700
tgttgcccag gctggtctca aactcctgag ctcaagtgat ccactcacct cagccatcca    23760
aagtgctggg attacaggcg tgaaccaccc tgcctggcct atataatcat tttttattgc    23820
agttccactt ttaaatttag gattaatttt tagaaagaat ttagttatcc ttaaatagaa    23880
gaaatttgca gtagctggtt tatgattata aaaaccaacc caaagttaa tttcaattgt    23940 gactcaaagt ctgttataaa tcagctttgc accttgagaa ctaacattta gcacttggta    24000
tatggtagga accttactct tgtcacttaa tcattttaac aacttagta ggtatcatca    24060 gtccaccttt aacagacgag aaagctgagt gagagcttag gtttcctgaa aaatttaatc    24120
ccaggtccgt ctgatgacaa gtccttgctt ttccattgga acactgaagt attatttaat    24180
acactgggca aaatagagtt ttgaaagtat tggaaaactg ctaattcata gtgaatggaa    24240
agttagcttt taggtggcac gttgttcaga aaggccgctg ctatgaataa aacatttaaa    24300
aattgctgtt tatgcctagc agatttgttt gcttatattt tacatttctt ttttttttt    24360 tttacatttc ttacacaatg cagagtacat tctgtacaat gtagaatgaa atcatgactt    24420
tggaaaacct gtttctttga ttcttctatg tttcagacag gcagagaggg gaaaaagatc    24480
tgttttaaaa ggcataactg gtaaaagctc agagtctgga gggcacattt ccgcccgctc    24540
ctctcccaca ttagaaagtt tctgtttgct gatgtgagca gggctaagcc tggtgaggtt    24600
cctaggaatt aattatgaaa aggggggaaat agggaggagg gccttccccg caaatcccct    24660
ccataagagc acgctaacca gagtagaagt caggggctcc gtgctttggc ccaggtgttc    24720
ctatcaaagg ttccacagac aacctttcag gcccagaatg gtgagctgga gaggaatggg    24780
tgcctgccac tgaggctctc ccttctctag ccctccttt actctctcct ctacttgtct    24840
tggcaggtgg gaaatggttg gaggttacta gaaagttgtt ccagctgtat acagaattac    24900
cctttgtttc cagaaacaac tgcttaagcc tccttactca tgactctgtt gacttctttg    24960
gccaagcttg gctgctgttt ttttttgttt gttttttcc cgacagggtc tcaccgtgtc    25020
acccaggttg gagtgcagtt gccgcagatc ttggctcact gcaacctcca cctcccgagc    25080
tcaagggatc ctcccatcag tgatcctccc accctagcct cctgagtagc tgggactaca    25140
ggtgcacact ggctgctgtt ttaatttgtc atcgtatcct gtatctgaca gagttcagtc    25200
catggtatca agctattgac tgagtgaaca aatgaatgaa ctagaagtag atttatactg    25260
cagcagggag gattgatgtt agacacattg aactgatggt gactataagg ttgttacgtg    25320
gtggacttag catttttaga gaccagaata tggaattttg ttcttaggta agtggtggtt    25380
aggttctttt ttttttttct ttaaatatga gacagagtct cgctccgtcg ccaggctgga    25440
```

```
gtgcagtggc gcgatcttgg ctcagtgaaa gctccgcctc ccaggctcaa gcgattcttc    25500
tgcctcaggc tcctgaatat ctgggactac aggtgcatgc caccacgccc aactaatatt    25560
tgtattttta gtagagatga ggtttcaccg tgttgtccag gatcgtctca atctcttgac    25620
cccgtgatcc acctgcctcg gcctcccgaa gtgctgggat tacaggtatg agccattgtg    25680
ccagggtggg ttcggtttta ttttgcccta gttgaaatca ggatgacttg gctggcacag    25740
atatatccct tctaaaataa aggaaaaaca ataaatgaag tggtgtgatc tagtcattta    25800
aagaagttat ctgtcattat ggaatcatca gcattcgcta ttattttatt tgcttttgta    25860
gagaccattt gaagtggatt cttgaattta gttttttccta aaagtagtat ctgctggata    25920
caaacattag tagcaaagta tagaagtgta gttcttttcc tctcttagat aaagaggact    25980
gtcttaatac agttctgcaa cttttttttc ttttaacat catggaagtc tttccacgtc    26040
aatacatgta aattcaccta tttttaaaaa accatgacat agatttctgt tcgatggact    26100 atatttatg tagacagttc tctatagaag aatattgaga tggtttccag ttttttcacta    26160 tttgaatgta gcaatgaaca ttaatatgta attgtatatc tatatggtaa aattcccaga    26220
agtggaattt ctaggacaaa agcagtaata cttttttgaag agcaattagg caaaatttag    26280
ctttctacaa acagtggtta agaactgttt ttccttatac tcttgtttac tgtatcatca    26340 gacttttttaa attaataaaa taacatttat tttattaatg ttataataaa tgttatttta    26400
attttaaaaa agatttatta gatacttaat atttcttttt ctaaggatta ttttaagtag    26460
catttcccat catgcattta tagagtagtg ctaatttata aacattaggt ttgtacatgt    26520
cttaaaggaa tacatttgtt ttatgtgtca tacctataat tctaggcaga aaccaatact    26580
ccttggagta cagagtaaaa aaaataaata aataaaacct ctttgttggg aaaggcttga    26640
aatacagagt gttattagag aagattctga agcaggaaaa tgctgttaat tgataaaagt    26700
tagatggaat aattgttaca atagacataa attaaaagca gcacattctc tgaaacggtt    26760
gattataaag ctgtgtagca cgagattgtg aatgggtttt ctaagataat attgtgaagt    26820
gctccttgga gacgataccc tgtcttatag tttgtgaatt tctaaatttc attttgttgt    26880
atattgaaaa taacatatt gtatgtacat atgtggtgag gttgttaat ttgttttta    26940 atttactca cttttttttt tttaggcaag tgtcagatat gctacatttt gtttctcagt    27000
aagggttaat attttccctt gctgtggttg agagaagcaa ataggcaatg aatagtcatt    27060
tgcacagaat tacccagaaa gtttacagtc tgtcctcaga agggcagaga ttgggttaat    27120
gcacacatag ccctggcaca tagtaggccc tcctatgtgt ttgaatgaat gccttcattt    27180
ttaaagtaga taaaatttaa ataattgtca gtggaaagtc tttttggacc attgtgaaac    27240
aggattcaag gccagagtga agggcttggg ggaatatgta cactactttt aataattagt    27300
ttgccttatc agtaaaatgg agaaaactat gtagagtact cgaaccttcc tgggtcatgt    27360
ttgaagatca aatgaggtga tgtttgtctt catagtcatt tgttttcaaa catgtatgat    27420 gttaatctttt ttttaaaaaa ttatacttta agttctgggg tacatgtgca gaacgtgcag    27480
gtttgttaca tagatataca cgtgtcatgg tggtttgctg cacccatcaa accgtcatct    27540
acattaggta tttctcctaa tggtatccct cccctagccc ccccacccccc gacaggcccc    27600 agtgtgtgat gttcccctcc ctgtgtccat gtgttctcat tgtttagctc ccacttatga    27660
gtgagaacat gcactgtttg gttttctgtt cttgtgttag tttgctgaga atggtggttt    27720
ccagcttcat ccatgtccct gcaaagaaca tgaactcatc ctttttatg gctccatagt    27780
```

```
attccatggt gtatatgtgc cacattttct ttatccagtc tatcattaat gggcatttgg   27840
gttggttcca agtctttgct attgtgagta gtgccacaat aaacatatgt gtgcgtgtgt   27900
ctttatcgta gaatgattta caatcctctg ggtatatacc cagtaatggg attgctgggt   27960
caaatggtat ttctggttct agatccttga ggaatcgcca cactgtcttc cacaatggtt   28020
gaactaattt acactcccac caatagtgta aaagtgttcc tatttctcta catcctctcc   28080
agcatctatt gtttcctgac ttttttaatga ttgccatcct aactggcatg agatggtatc   28140
tcattgtggt tttgatttgc atgtctgtaa taaccagtga tgatgagctt ttttttcatgt   28200
ttgttggctg cataaatgtc ttcttttgag aagtgtctgt tcataatctt cacccacttt   28260
ttgatggggt tgtttttttt ttcttgtaaa tttgtttaag ttccttgtag atcctggata   28320
ttagcccttt gtcagatgga tagattgcaa aaattttctc ccattctgta ggttgcctgt   28380
tcactctgat gatagtttct tttgctgtgc agaagctctt tagtttaatt agatcccatt   28440
tgtcaatttt ggcttttgtt gccattgctt ttggtgtttt agtcattaag ttgttgccca   28500
tttctgtgtc ctgaatggta ctgcctatgt ttttcttctag gttttttatg gttttaggtc   28560
ttacgtttaa gttttaatcc atcttgagtt aattttttgtg taaggtgtaa ggaaggggtc   28620
cagtttcagt tttctgcata tggctagcca gttttcccaa gaccatttat taaataggga   28680
atcctttccc cattgctttt gtcaggtttg tcaaagatcg gatggttgta gatgtgtggt   28740
gttatttctg aggcccatgt tctgttccat tggtctatat ctctgttttg gtaccagtac   28800
catgctgttt tggttactat agccttgtag tatagtttga agttaggtag tgtgatgcct   28860
ccggcttttgt tcttttttgct taggattgtc ttggctatct gggctctttt ttggttccgt   28920
atgaaattta aagtagttttt ttctaattct gtgaagaaag tcagtggtag tttgatgggg   28980
atagcattga atctataaat tactttgggc agtatggcca ttttcacgat attgattgtt   29040
cctatgcatg agcatggaat gttttttccat ttgtttgtgt cctctcttat ttccttgagc   29100
agtggtttgt agttctcctt gaagaggtcc ttcacatcct ttgccaaatt gtattcctgg   29160
gtatttatt ctctttgtag caattgtgaa tgggagttca ctcatgattt ggcttttctgt   29220
tattggtgta tagaaatgct tgtgattttt gcacattgat tttgtatcct gagactttgc   29280
tgaaattgct tatcagctta aggagatttt gggctgagat gatggggttt tctaaatata   29340
caatcatgtc atctgcaaac agagacaatt tgacttcctc tcttcctatt tgaatatcct   29400
ttatttctttt ctcttgcctg attgccctgg ccagaacttc caatactgtg ttgaatagga   29460
gtggtgagag agggcatcct tgtcttgtgc cagttttcaa aaggagtgct tccagttttt   29520
gcccattcac tgtgatattg gctctgggtt tgtcataaat agctgttatt attttgagat   29580
acatcccatc agtacctagt ttattgagag ttttttagcat gaagggggtgt tgaattttttt   29640
cgaaggtctt ctctgcgtct attgagataa tcatgtggtt tttgtcattg ttctgtttta   29700
tgtgatggat ttcgtttatt gatatgcatg tgttgaacca gccttgctgc atcctaggga   29760
tgaagccgac ttgatcatgg tggataagct ttttgatgtg ctgctggatt cggtttgcca   29820
gtatttatt gagaattttt gcatcgatgt tcatcaggga tattggcctg aaattttctt   29880
ttttgttct atctctgcaa ggttttggtg tcaggatgat gctggcctca taaaatgagt   29940
tagggaggag tccctctttt tctattgttt ggaatagttt cagaaggaat ggtaccagct   30000
cctctttata cctctggtag aatttgactg tgtatccacc tgatcctaga cttttttga   30060
ttggtaggct attaattact ccctcaattt cagaacttgt tatttgtcta ttcagggatt   30120
cgacttcttc ctagtttaga ctttggaggg tgtatgtgtc caggaattta tccatttctt   30180
```

```
ctagattttc tagttcattt gcttagaggt gtttgtagta ttctctgatg gtagtttgta    30240
tttctgtggg atcggtggtg atatctcctt tatcattttt tattgcatcg atttgattcc    30300 tctctcttt cttctttatt agtctggcta gcggtctatc tattttgttg atcttttcaa    30360
aaaaccagct cctggattca ttgatttttt tgaaaggttt ttcatgtgtc tatctccttc    30420
agttctgttt tgatcttagt tatttcttgt cttctgctag cgtttgaatt tctttgcgct    30480
tgctgctcta gttcttttaa ttgtggtgtt agggtgttga ttttagagct ttccagcttt    30540
cttttgtggg catttagtcc tagaaatttc ccactaacca gtgctttggc tgtgtcccag    30600
agattctggg atgttgtgtc tttgttctca ttggcttcaa agaacttatt tctgccttaa    30660
tttcattatt tacccagtag tcattcagga gcaggttgtt cagtttccat gtagttttac    30720
agttttgagt gagtttctta atcctgagtt ctaatttgat tgcactgtga tctgagagac    30780
tgtttgttat tatttctgtt cttttgcatt tgctgaggag tgtttcactt ccaattatgt    30840
ggtcaatttt aggataactg caatgtggtg ctgagaagaa tgtatattct gttgatttgg    30900
ggtggagagt tctgtagatg tctattaagt ctgtttggtc cagagctgat ttcaagccct    30960
gaatatcgtt gttaattttc tgcctcattg atctgtctaa tattgacagt ggggtgttaa    31020
agtctcccac tattactgtg tggaagtcta agtctttttg taggtctcta agaacttgct    31080
ttatgaatct gggtgttcct gtattgggtg catatatatt taggatagtt agctcttctt    31140
gttgcattga tccctttacc attatgtaag gcccttcttt gtctcttttg atctttttgg    31200
tttaaagtct gttttatcag agactaggat tccaacccg actttttttt gctttccatt    31260
tgcttggtaa atcttcctcc atccctgtat ttcgagccta tgtgtgtgtt tgcacatgag    31320
gtgggtctcc tgaatacagc acatcaatga gtcttgactc tttatccaat tcgccagtct    31380
gtgtctttta attggggcat ttagcctgtt tacgtttaag gttagtattg ttatgtgtga    31440
atttgatcct gtcattatga tgctagctgg ttattttggc tattagttga tgcagttttct    31500 tcatagtgtc tatggtcttt acaatttggt atgtttttgc agtgactggt accagttgtt    31560
cctttccatg tttagtgctt cccttcagga actcttgtaa ggcaggccta gtggtgacaa    31620
aatctctcag catttgcttg tctgtaaaga attttatttc tccttcactt atgaagctta    31680
gtttggctgg atatgaaatt ctgggttgaa aattattttc tttaagaatg tcgaatattg    31740 gccctattc tcttctggct tgtagggttt ctgcagagag atctgctgtt aagtctgatg    31800
agcttccctt tgtgggtaac ctgacctttc tctctggctg ccctcaacat tttttccttc    31860
atttcaagct tggtgaatct gacgattatg tgtcttgggg ttgctcttct tgaggagtat    31920
ctttgttgtg ttctctgtat ttcctgaatt tgaatgttgg cctgtcttgc taggttgggg    31980
aagttctcct ggataatatc ctgaagagtg ttttccaact tggttccatt ctccccgtca    32040
ttttcaggta caccagtcaa acttatgttt ggtcttttca catagtctta tatttcttgg    32100
aggctttgtt tgttcctttt cattctttt tctctatctt gtcttcacgc tttatttcat    32160
taagttgatc ttcagtcgct gatattcttt cttctgcttg atcgatttgg ctattgatac    32220
ttgtgtatgc ttcacgaagt tcttgtgctg tgttttcag ctccatcagg tcatttatgt    32280
tcctctctaa actgattatt ctagttagca atttctctaa cctttttca gggttcttag    32340 cttccttgcc ttgggttaga acatgctact ttagctcggt ggagtttttt tattacccac    32400
cttctaaaac ctacttctgt caatttgtta aacgcattct ccatccagtt tgttcccttt    32460
gctggcgagg gagttgtgat cctttgaagg agaagaggca ttctggtttt tggaattttc    32520
```

```
aggcttgttg cgctggtttc tccccatctt catggattta tctacctttg cttttgatg    32580 ttggtgacct tcggatggcg tttctgagtg gacgtccttt ttgttgatat tgatgctata    32640
cctttctgtt tgttagtttt ccttctaaca gtcaggtccc tctgctgcag gtctgctaga    32700
gtttgctgga ggtccactcc agaccctgtt tgcctgagta tcaccagcag aggctacaga    32760
acagcaaaga ttgctgcctg ttccttcctg gaagcattgt ccctgagggg cacctgccag    32820
atgccagcca gactctcttg tatggggtat cttttggccc ctgctggggg gtgtctcctg    32880
gtcaggagac acagggtca cggacccact tgaggaggca gtctgaccct tagcagagct    32940
cgagcactgt gctaggagat ccactgctct cttcagagct ggcaggcagg gacctttgag    33000
actgctgaag ctgcacccac agccaccatt tgccccaggt gatctgtccc agggagatgg    33060
cttcatctat aagcccctga ctgggctgc tgccttttt tcagagatgc cctgcccaga    33120
gaagaggaat ctagagaggc agtctagcta cagtagcttt gctgagctgc ggagggctcc    33180
agccagttgc catttccctg tggctttgtt tacactatga ggggaaaacc acctgctcaa    33240
gcctcagtaa tggtggatgc ccctcccccg accaagcttg agcatcccag gtcgatttca    33300
gactgttgtg ctggcagtga gaatttcaaa ccagtggatc ttaacttgct gggctctgta    33360
ggggtgggat ccgctgagct agaccacttg gctccctggc ttcagccacc tttccaggcg    33420
agtgaacggt tctgtcttgc tggcattcca ggcaccactg gggtatgaaa aaaaaactcc    33480
tgcagctagc ttggtgtctg cccaaacggc tgtccagttt tgtgcttgaa acccagggcc    33540
ctggtggtgt aggcacccga gggaatctcc tggtctgtgg gttgtgaaga ccgtgggaaa    33600
agtgtagtgc ctggaccaga gtgcaccatt cctcatggca cagtccctcg cggcttccct    33660
tggctagtgg aggaggttca ctaaccactt gtgcttcctg catgaggcaa cacccacc    33720 tgctttggct tgccctccat gggctgtacc cgctgtttaa ccagatgagc tgggtacctc    33780
agctggaaat gcagaaatca ccctccttct gcgttgatct cgctgggagc tgcagactgg    33840
agctgttcct attcggccat cttgccacaa gctgatgtta gtcttttagg gcccattagc    33900
tctcaagcct tcctgtacaa ctgtaagatg gccattatta ttactcccgc cagatgccag    33960
ccggagcttt cttgtatcta aacctgtgtt tgttttttaa aactcatcag gagagttttt    34020
tcctccaaag atcatcttaa ttgaagaact gaattaaaag catacatgtg ccctgtgtct    34080
acacttaaaa ctatccaaaa cacaaacctt tatacctaaa ggaaactgag gcctggattt    34140
gctcagataa tgctggaatt catacttaaa actctcagac ataccctcaa gaaattcaga    34200
agtaggaaag acagatattt aaacaaatat atgtgaaaat gctctttgaa ctataaagca    34260
atttacaaaa gtgtcatcaa ttcatcattg ttgttatctt tatcacagtc aataatattg    34320
ttgcccaaat tagaatggtt taacaaaaca ttttcttcct tgccttagag caggggtgtc    34380 caaactttg actttcctgg gccacattag aagaagaatg tgtcttcggc cacacataaa    34440
atacgctaac actaataata gatgatgagc taaaaaaaa aaaaaaaaat tcacacccaa    34500
aaaaatctca ttatgtttta agaaagtttta caaatttgtg ttgggccgta ttcaaagcca    34560
tcctgggctg catgtggctt gcaggccatg ggttggacag gcttgcctta gacaaacggg    34620
aaaatcacat ttatttctg cttgtgaaag taacacttgt ttttttaatt taagtttgaa    34680
aaattggaac tatgtacaga tattttttaaa aatcagtatt tcataactca ccaaaagata    34740
acctgaattt tctctactga tatttacgtt tatcccctg tatacttaat gttcatagag    34800
gttaatatgg gacattgatt cttcctcagt gggggtttta gagaccaacc cccactggcc    34860
tggatgcctg ggatggtttg ggtgagatcc tttcttgagt caggcatcat ttttgacctg    34920
```

```
tgccctcccc tgtgaatttg tggcatccag agaattctta gataaggccg agcaaggcag    34980
tactcattcc agatattcag gatgtacgtg gtccagagct gttgtcttct ctgacttgtg    35040
tcttgtgtgc cttctcctgt aagtgtggtt gccttgatta gggatattga ggaaagtgga    35100
gcgagtgtgg atattttgct gtagttttcc tgaggtgaca gatactagtg ggtgaagcca    35160
gggctcaggc agctcagctc tcttgtgtgt tagcctggct tgctgcttgc aggtatggct    35220
gtttattttc atttcacttt tctgcattgt agtctcttcc tataattaac atggctgaaa    35280
agaaaaggtt actctaaaag ttgtttttaa aaaatacaga gcctctcgga tttctcagca    35340
gcgtttaaat cccagctctg ttacttaatg ttgatttgtg ctcttggata agcttctgag    35400
tcagtttcaa cagtgaaatg gtgataatat ctccttctag aattgcccta agcatgaggg    35460
atataaaatg ccatcctcat aaaataacac tcagaatcat taattatttg ttattattgg    35520
atctgcgtgc atatgaaaga atccggactt ttttgtattt tgaatcccat gaaagttcag    35580
atgtgttaag ttgtatgggg ggaggtgata tattggaaaa gttgccttca tgtataacat    35640
gtttgcctca taagttgtta tgggtgttat acatccttca aagtgaaaga attcttgagg    35700
ataggcagca ggggactgac tggtatccta tttaaggttg atgggaatcc aagagtgatc    35760
aagagacctc caaagtggcc agtggtcctt cacttgtaca tgagttagta tttttttgatt    35820 tgtgatcaca gccactttct aacaaagcat gttgttctg cttttcact atcagattgg    35880 ctttgaaagc cttcatgaaa acatgccacc cagtttctga tttcttcata tcagaatggc    35940
ttatccagag attttgtttt cctttctggc ttcatcttgg tgaatcagta gttattttt    36000 taacctatat tttattttaa aagccctggc actctcagca aatttcgtgt gacttgggta    36060
cctagagagg tagcagagaa ttgaaattca cttttggact ccccttctgtg gcctcctctg    36120 cttccagtcc tttctcatcc tgacgtctac catcatttat caaaaattca aaagctagaa    36180
aaagtcattc taaagcctgg tgtgggtct gcagaaaatg tcccaaatgt ctgtccgtaa    36240
ggagtgcaga atcagtgggg aattagataa actagggctt tcacaaggct ttctgggata    36300
tccatgtgga accttggcct gctctccatt tctgtgactc tttgatgggc ccttaaatct    36360
aaacctgtgt ttgttttta aaactcatca ggagagtttt tccccccaag gatcatctta    36420
attgaagaac tgaattaaaa gcatgcatat gccctgtgtc tacacttaaa actatccaaa    36480
cactaccagt tgtttaatga ggttgttcct agaccaacag atactttagt gttttgtaga    36540
gatatgttat ttgcaaggct ttgtcttctg taactgcttg gccttaaaaa cctgcctgtc    36600
tagaaagggg ggcctctgag tagtgtttga taataagaaa ttgctttcag tactactgca    36660
aacccttttg gcagaaacat agaatcaaca ttctagaaat taagggctgc tgttatggtt    36720
tggggtttgt aaagttgtag ttggagcgag gaccaaaaaa tgtaaactgg gttatcatga    36780
gggatttgtt tttccaacaa actagatggt tgagggttat gtctttctta ttatgaggaa    36840
gaggtttttg cctaataagg tactatatga aaatgaatgt ctttgaatat cttcttagtt    36900 tttctttat ccttggttct ttttttaatta aagaagtatt taattaacac caactacaat    36960
caagtcactg ttctgagtct tcttttgtgct catgttattt taattttaaa ttaattttta    37020
gattttggta atgtgtgtat tgtacagtta aattatatag tgaaagtaat tctctgtatc    37080
ccagccacct ggtccccttc agctgcctaa tcttcctcaa attctgtact agcttttgca    37140
ctgtcccaga gataatccat gcctatacaa gcatccattt gtatgatatt ctcttgtttc    37200
acacaggtag tcctagcacc atgacagaat tgtagccctc tcagtgaact acacaccctt    37260
```

```
gtattcaagc tccgtgtaat tcctgcccat attgactgtg cttggccgtg tgactggttt    37320
tggccaatgg gtgttagcaa gtgtgatgca agcagaggtt tgataagagc ttgcactttg    37380
aaatgtgttc tagaggagtg cttgctattg tgacactccc tctcagtacc cagaagcccc    37440
cagctgtgag gtccccacct agtcataaag agaagccaca tggaagagaa ccgggtccct    37500
gccaacagcc tcatctgagc ccctagccgg cagcaagcat ccacttggca gccatgtgat    37560
gaatgaacta tcttcttgga agtggaactg ccagccccat tcaggccacc cccagtggtg    37620
ctatgtggag aagagacaag cttccctgc caagccctgt ccgaattgaa aaattgtgag    37680
ctgttgctag taatgtacta aagttggttt gtcatgtagc aacagataac aaacacatgc    37740
tatatatatg atattttctg tgccttgctt ttgttgctga gcagtatatt agatatcagc    37800
ttatttcatt acatacagag tcacatcatt cattttaaga gctgaataat attccattta    37860
tggctgtaca gtaattaact agcctcttat tgatggacat tgatgtttct aatctttctc    37920
agcatttaat atctccatgg catgctttgt tttgcacatg aacaaatata tttattgggt    37980
aaattcttag aagtagagtt gctgagtaaa agagtacgta aatttgtaat tttaataggt    38040
attgcaaatt gccctccaga gaggttacac tcccactagc aatgtaggaa gactgtgcca    38100
gtgtggttgg aatgttacat ttctttttaa tattttccca tgtattttaa aaaccatatg    38160
catttctttt ttgatgaact gtcttctttt ttgtttggat tgttggcctt tttctttttt    38220
ggaggaactc tctgtattta aagaaattaa ctcttaatgt atgctatgtg aagcaaatct    38280
ttttcccccc agtttttat cttttgactt catttgaata attttttgtc cttattgtgt    38340
ttagttatgt caaatctttt atagcttttg gattttcttg gttttgttct ggtttgttgg    38400
tcatatttag gcttttctca ctttaagatt attgtagata ttctcctgtg ttttcttcta    38460 gtgttttgt tatttctttt ttacatgtta atctttgatc tgcctgaaat gtcttttgac    38520
gtagacgttt ccaggtaggt gtccgaggtg gctagtcatt tgtctgttaa tattgttata    38580
ccatgtcatc cttactatac agtcatgatg ctttagtcaa tgatggactg cacatatgac    38640
actggtccca tgatattaca atgaaactga aaaattccta ttgcctagtg atctcgcagc    38700
tgttgtaatg tcatagtaat gcattactca tgtattttg gtgagctggt gtaaaccaac    38760
ttactgtact gccagtcata taaaaataga gcacatacaa ttctgtacag tacataatac    38820
tcgataataa atgactatgt tactggttta tgtatttact atactctatt gttatttag    38880 agtgtactcc ttctacttat aaaagaaaa agttaactgt aaagtagcct caggcaggtc    38940
ctaggaggta tccagaagaa ggcattgtta ttataggaga tgcagctcc atgcctgtta    39000 tcgcacctga agaccttcca gtgggagaag atgtagagat ggaagacagt tatactgatg    39060
atcctgacca tgtgtaggcc gaggctaatg tatgtgtttg tgtcttagtt tttaacaaaa    39120
atgcttaaac agtttaaaaa taaaaaaatt ttaaaagctt ataggataag tatataaaga    39180
aaatatttga taaagctgtc cagtgtgttt gtgctttaag ctaagtgtta ttacaaaaga    39240
gtcgaaagta aaaaaaaaaa aaattaaacg tttatgaagt aaaaaagtta cagcaagctg    39300
aggttaatta ataaattatt attattgttt cagagacagg gtcttgtttt gtctcccagg    39360
ctagagtaca gtggtgcaat catagctcac tgtaaccttg aactcctggg ctcaagcagt    39420
cctcctgcct cggcctccca agcattgag attacaatga gccactgtct ggctatgttg    39480
atttattgtt gaagaaataa aactatttt tataaattta gtgtagccta agtttacagt    39540
gtttataaaa tcgacagtag tgcagtgtcc taagtcttca catctactca acactcattc    39600
accgactcac ccagagcaac ttccagtcct gcaagctcca ttcatgataa gtgccccata    39660
```

```
caggtgcacc attttttaat cttttatatt gtgtttttac tgtacctttt ctatgttcag   39720
atatgtttag atacacaagt acttaccatt gtgttacaat tgcctacagt attcagtaca   39780
gtaacatgct gtacaggtgt gtggcctagg agcaacaggc tacaccatac agctcaggtg   39840
tttggtaggc tacatcagct aggtgtgtgt aagtgactct atgatggtca cacaacgatg   39900
aagtcacaat gatgactcat ttctcagaat gtatcaccat ccttaacatc attaaacatt   39960
catgtattta ctggattcag caatatcttt tgaactgctg tcccccaaat tacttaatta   40020
ttccctttt  tctcttagga aatgctacag tgaatattta aaattctatg taattattaa   40080
tcccaaacct ttgtggatat agaaatcaac atttatatag tctgcatttt acaagttatt   40140
taaacatttg tgttgttaag ctgctcaaaa gccggttggc aaggtctgca ttttatgcac   40200
aggaaaaagg agaagatcat tccatgtaaa ggagattcat ctgaagcaaa gcaggattgt   40260
gtacaagtag agagaaatgt gcttttttat gatgtatcat gtataaaggc ctgttcccaa   40320
atttctgaag cacatggaag ttctggtgta aaaagtatat ctagttaaga cagctgtagg   40380
ctgggagcct gtgaaaggaa gattttgctt gttaatagaa tgactgagac tacatcatcc   40440
tgtgtagaaa ccagggaata acacttgtac tgtgttgtgt taagaaaaca ggttctttaa   40500
ttaagtgatg tacctgaaat ttcaggtaat gactacagct ctcctgaaca cccaggaggg   40560
cggtgacact gagtcacagg cagaactatg aaattccttg tgaaactcaa ctttctgttc   40620
ttccagcctt tcccctcccg ccctcggct  cagccacagg tgctcattaa acctcgccca   40680
gggagcatac ctccaaagct ttttcacagg catgtggccc acctttggat tccgaccta   40740
tggtcctggg aagtctgcat ttggagcgtg tacctgaagg gtgttaagca catttaacct   40800
ctgctaagat aatcagacag acaccctag  aaagagatat agaagtaagg tgttgactat   40860
tctggggttt gtatttcagc aggaccccca aagtttgagc tgaaaggact aagttctgtg   40920
gggaggtatc agccagaggt ggggaccctct tttgggatac ctgtgccttc ccaccgtgag   40980
ccgctgtgcc ctctgcctct gctgcaggcc agccgtgctg cattccatat gtaaagctgt   41040
gtcgtgcttt ccttctttcc ctcagaatcc tccacgtctg ttgtgtgaga acgacatttc   41100
actaaggagg acagacagtt agcttctgtc agagaagaat gtcagagctc tttcattttg   41160
tagatgctgc ctttagcttg ctttctgtgt atgttatgtt cttctaccct tgggatattt   41220
tgacaccagt ggcattgttt tccatttct  cagtgccaga gaagctggga tgttgtagaa   41280
aatatttggt ttcaaggtta aaaaatgtta tttctttct  ttttagatct tatctaagct   41340
ttctttgcct acccgtgcct gggaaccagc aatgaagaag agttttgctt ttgacaatgt   41400
tggctatgaa ggtggtctgg atggcctggg cccttcttct caggtggcca ccagcacagt   41460
caggatcttg gcatgactt  gccagtcatg tgtgaagtcc attgaggaca ggatttccaa   41520
tttgaaaggc atcatcagca tgaaggtttc cctggaacaa ggcagtgcca ctgtgaaata   41580
tgtgccatcg gttgtgtgcc tgcaacaggt ttgccatcaa attggggaca tgggcttcga   41640
ggccagcatt gcagaaggaa aggcagcctc ctggccctca aggtccttgc ctgcccagga   41700
ggctgtggtc aagctccggg tggagggcat gacctgccag tcctgtgtca gctccattga   41760
aggcaaggtc cggaaactgc aaggagtagt gagagtcaaa gtctcactca gcaaccaaga   41820
ggccgtcatc acttatcagc cttatctcat tcagcccgaa gacctcaggg accatgtaaa   41880
tgacatggga tttgaagctg ccatcaagag caaagtggct cccttaagcc tgggaccaat   41940
tgatattgag cggttacaaa gcactaaccc aaagagacct ttatcttctg ctaaccagaa   42000
```

```
ttttaataat tctgagacct tggggcacca aggaagccat gtggtcaccc tccaactgag    42060
aatagatgga atgcattgta agtcttgcgt cttgaatatt gaagaaaata ttggccagct    42120
cctaggggtt caaagtattc aagtgtcctt ggagaacaaa actgcccaag taaagtatga    42180
cccttcttgt accagcccag tggctctgca gagggctatc gaggcacttc cacctgggaa    42240
ttttaaagtt tctcttcctg atggagccga agggagtggg acagatcaca ggtcttccag    42300
ttctcattcc cctggctccc caccgagaaa ccaggtccag gcacatgca gtaccactct    42360 gattgccatt gccggcatga cctgtgcatc ctgtgtccat tccattgaag gcatgatctc    42420
ccaactggaa ggggtgcagc aaatatcggt gtctttggcc gaagggactg caacagttct    42480
ttataatccc tctgtaatta gcccagaaga actcagagct gctatagaag acatgggatt    42540
tgaggcttca gtcgtttctg gtacgtagtg tgtttgaggc atgtcctgag cttgtctcct    42600
tttctctttg tgtcttatag ctcctggatg gtggtatagg tgagccctgc tccctgcctc    42660
ccatgtcaac agtggaacaa aatcctgcaa actttccttg catgttaaat ttgttaagat    42720
agaggaaata taatctccaa gtgtctagat tttgcttttc atgtagttgg gattttgtat    42780
tagtctgttt tgtgttgctt ataacagaat ggctgaattt gggtaattta taagatatg    42840 gaatttgttt cttatagtta ctgagaagtc taaggttgag ggccacatct ggtgagagcc    42900
ttctgccagt ggggactccg gtgccacagg gcatcacatg gcaggggtgc tgagcatgct    42960
cacgtggttg cttaggtggc tcttcctctt tttagaaagc ctcgatgcca cacctgtgat    43020
aacccattaa tccatgagtg gattccattc atgagggtag aaccctcatg atccagtcac    43080
ttcttaaagc cctcacctt taacactgcc acattgggga ttatgtttcc aacacatgaa    43140 atttgggga cacagtcaaa ccatggctga cttgaatgcg aacctccttg gatttgggct    43200
tcttttctgg agagaattct gattctgtat cctgaaatag agcactgtgg gaccatccag    43260
gcccttttct taccaagaga actattatca ccttctcaaa agattttact gctaaacaac    43320
agaaccttag tctcatcacc tagagaccat gctggtaaaa atgagagtta aggaaaggat    43380
ttataaatga tttttttctc cctgtttgat gaatataaga gaagaggtaa aggtgaggga    43440
gccaccaggc ttttatattt tttaattaaa aaatttttta attttttttag ggacacggtc    43500 ttgccctgtt gtccaagatg gaggatagtg acatgatcat aggtcactgc atccttgaac    43560
ctttgggctc aggtgatcct cgcacctcag cctcctgagt agctgggact acaggtgtgc    43620
accaccacac cgggctcatt ttttattttt atttttttgt agagacggag tgttgctgtg    43680
tttcccaggc tggtcttgaa ctcttggcct ctagcaatcc tcccgcctca gcctcccaaa    43740
gtgctgggat tgcaggcgtg agccactatg ctcagccacc atcatgggtt ttaatcagag    43800
gaagcacgaa gtcagattat attttagaag actggtgtgg tgtcacagta cagtgtccat    43860
ggaggcaatg agaccacgta ggaggccggg tgagaaagag gtgggtttga aagacattca    43920
ggagggcagc tccaccaagc ttggggtcac caagaggggt gtgtgatggg gagggccatg    43980
gaggaaaggg gtaactggga tgagcccttta gctgagatgc tggaggacag tgggatagaa    44040
gggccttgaa ttttgaggga gagtgtgggg ccggaaatgc agagtgtggg aagatgacag    44100
agacctagaa agagtgattg tgagatggga aagaattaga gggaggagga ggggtctcct    44160
agtcaccctg gacataatgc gagccgcaga ggccaaggtc tgaatcgtat cttcgcgggt    44220
taactagggg aggccattgg aggcctcggc agctgcttca ggaccctggg aaggtgggag    44280
cccagcttgg ctgctggtaa gggtggagac cactagtagc ttagattagg gataaagagg    44340
atgataggtg agtggagatg gttgagagaa atgctgaaga taaggaggga aggggcacat    44400
```

```
gttgtgaggg gcagctgtgt gggtggtgtg ttgtaaccga ttaggtccca gacatgggcc    44460
ctgcccgtgc gtgtctctgt ggactggacc aggacatggc tggcttcctc agccttttgg    44520
ctggagctcg gtactgtagg gagcagcggg cccaacacta agaagagctg ctttcagtgg    44580
cgtgggcaag cccactggca gctcagtgct cagggatggc tgaactttgg tttcccacat    44640
catttcctgt ggtcactgag ataaagtttg tgtccttgaa aagttcactc agctgtgagt    44700
ctttgctgcc tcccctctgt gcccacagca cacacctact gctgaaggga gtgggcattc    44760
atgtggagtg gcctggcccc attttgtgct ttgtcttttg tatcaagttt caggaaggag    44820
tttctttaaa acaaaaatca ataaggaaaa cacaatagaa cagtaaatcc tgtacgcaat    44880
aggtaagaaa tatagtataa ggtaaacatc tgcctgtttt tgtgtgatgt ttaaagtctt    44940
tcaaccgtgc aatcaggtta ttagtggtaa aaagaaatta gcactgaact tacatattac    45000
agaataattg gatttgatta aataaaccta gaaagaaaag aatagtgatt ttttaattg     45060 ggcaggatta tgagaatttt atttagccga agaggtattt agggtatcag acttagcaaa    45120
taaaaatata ggacatctac ttaaatttta attttcata aacaatgaat ggttttttag     45180
tataaacatg tccagctcaa tattcatgac atatgtatag taaaaattat tgttgtttg     45240 tctgagaatc aaatttaact ggatgtcctg tattttacct ggcaacttta atttggaata    45300
aaccattagt gtgccagttt gtatttgaag agcccttctt gattgattag gagctccttg    45360
aggacagcct tgcggccagc gtgatttgtt tctccttgga ctcaatagca ccccgcatgc    45420
agtaagtatt cctgaaggaa atgaaagata aggtgaagtt acggggtagc tcagtggaag    45480
gatttaatat agagaactat ttacaaaggt attagagagc tggaaatcca aataggcaat    45540
gggaagaacc ccagagatta acaacagcag ggagctctgt cctccaggat ggctgaggga    45600
caaggtagtt actggagccc aggggctgag gctgctcggt gggagccggg acaatgaacc    45660
ctcaccaaga gccctgaaac ctcttgttct gaaaaacata ttatttgctc ttctaatttg    45720
aatattttct gacattttat cctagaaagc tgttctacta accctcttgg aaaccacagt    45780
gctgggaatt ccatggtgca aactacagat ggtacaccta catctgtgca ggaagtggct    45840
ccccacactg ggaggctccc tgcaaaccat gccccggaca tcttggcaaa gtccccacaa    45900
tcaaccagag cagtggcacc gcagaagtgc ttcttacaga tcaaaggcat gacctgtgca    45960
tcctgtgtgt ctaacataga aaggaatctg cagaaagaag ctggtaagag atgaacgccc    46020
atgttgaact taggaatgct gcgtatagac ctcgtattct cccttcagaa tacccagcaa    46080
ctgtgtttat cagtagccct gataaccagg tagcaagttc attatatagc ataaatgttt    46140
gtctaatgtc cttgtataac tggcattgtg ttctttaaga agtatttagt ttgagataaa    46200
atatatctct gagtaagtta gccattgaaa atccagttta aaggtcatag tacccttttgt   46260 ggatagactt ctcagttagg ttgtactagt attattccat attttgttcc ctcccatccc    46320
atcaacccct tactataaaa tgaataaata acctgcattt tgtatagaag ttccaatttc    46380
aaatattctt tcttgttgtt cctgtaaacc agagagtgtt tgtaggaaca acaggacaga    46440
aatatgtgga aatgtcaaag ttttgtcctc cagaatgcat ttccaatact tttaaacctg    46500
aaagtacaat aaaattcgga tccatttatt tgtttggaaa atctcttaac catgactcta    46560
ccttgccacc agaatcactt tctcttttct taccccagtg atgtgtcttt ttacttgaac    46620
tccctggccc ttagaatcag ccctgaattc agatgacatg ttttttccagc ctcttgttca    46680 ctatgcatta tagcttcctg cagctctaga gtgactgtta gcagatggag gtgttaatag    46740
```

```
gagatccctt gttatccatg gtctgactgc tcataaaatt agcctataat ctcctatagc   46800
ctatgtttct gttcctgact tgaatcctca tttttatcct atgtggcatc ctttctgaag   46860
cacttccttc ctttcattta tttgaacgag gctttttttc ccatgtaaaa ctaacacaat   46920
agtgttagca agattgtggg atttcttttt catacctgaa agtcattaga aactataaaa   46980
gagtaaggaa aaccactttt gaaaattctt tatttttttcc ttgtatgaaa gtatctggag   47040
aaaaggagaa aaaaaaaaaa ggatatcctt ccggtaacag cagtcaataa ctgcagacca   47100
cattccttat ttcattggtg tcttctaaag cctgagtgag aatgtgtcca tgggcaggca   47160
gcatgagcat cacctgggag ctggatggac ctgcagactc tcaaacctca tcctagaccg   47220
actagtcaga agctctattt taacaaggtc ctcgggtgat tcatatgtcc attaaagttt   47280
gagaagcatt gttcttctag aatagtggtt gtcagacttc cctgtacatt aggatcacct   47340
ggggagcttt ttttttttaa aaaaaatga tgccttggga ggccaaggcg agcggatcac   47400
aaggtcagga gttcaagacc agcttgacca acatggtgaa accccatctc tactaaaaat   47460
acaaaaatta gctgggcatg gtggcacgca cctgtaaccc cagctactca ggaggctgag   47520
gcaggagaat cacttgaacc ctggaggcag aggttgcagt gagccgagat catgctactg   47580
tacccagcct gggcaacaga gtgagattcc atctcaaaaa aaaaaaaaaa agaaaaaaga   47640
aaaaaagatg cctgccacct accctgggat actctgattt ggttggtctg ggtaagagac   47700
cagacatcgt gattgtcgaa ggcttttccaa gcaagcctca tgtgcagcct cattttcaaa   47760
cagtgtttga aaactgctgt tctagaggat tctgggaaga tgtgtttctt tgttcggtta   47820
tattgactgt gtcaacctag aggccctgcc cacccagagt gttacagcca tgacctgatg   47880
gttccaggtg ttctctccgt gttggttgcc ttgatggcag gaaaggcaga gatcaagtat   47940
gacccagagg tcatccagcc cctcgagata gctcagttca tccaggacct gggttttgag   48000
gcagcagtca tggaggacta cgcaggctcc gatggcaaca ttgagctgac agtaagtact   48060
gtgggtgcgt tacggggtta caggcttctg acagtttgca ttttggacac atccatcttt   48120
gtgattagta aatttcccca tcttggacgt gtctggtttg ttgttgttgg gtattttgtt   48180
tgtttcactt tccttttgaag ccgacaacaa tgacttgttc attttaagaa aggtcagtta   48240
cgttaaacag tcatggggag gatcccactg agagtattca gggtgttagg aggaagagat   48300
ggtgagctgc aggagtatag aagaaacagg aattaaagac ggtggactgc cctgagctgg   48360
gtggttaggg ggagttgaac atgaacacag tccttcaagc ctaaaagaa gctagcatgc   48420 ctgcaactat ctcaaggcag aagagggaag tccatgtggt agaaagtgcc attctaagag   48480
aaaagggctt gtgataggtg catgggtgtc tagagggcca aagtgctcca caacactcag   48540
tctgagggga atgctccagg tagtgattgt tgccagtgtt ttgggtgggg aggtattatt   48600
tcccatctgt ctacgtgcca acacattatt gaaaacaatg gatgtgtctg atgcctagaa   48660
catgctatgt ttgaaagcac ttctgtactt tttgtacagc tctttttgtg taagcaaagg   48720
gagacttaga agaactcaca gagaattgaa tgatgctgct ttacccaggc cagagggttt   48780
ctacttcctt tgtgtgtttt gtcagtgcca ttagtggtaa ctggatgttt gaggggaaag   48840
cactgaggac acagaggccc atgagctcct gataagccgt gttctttgtg gagcaaaccc   48900
tttgctgtgg tagggcctcc ctgtgtctgg agggcatagc tgatacttgc tgggacacag   48960
ctttggtcag ccccacaaga ggtgcccaac aagaggggca gggtctctgc tgcaaacctc   49020
tggatctaca tgtggacatc tctgcctgct cagacttcta tgtggaaaat ctaaagcaag   49080
aggattattg gaaaaggtgt acatttcttt taaacaattt ttttattgta gtgttctttt   49140
```

```
ttcttttagc acacatttat taaacaaagg gataatccta attaatccaa cacactttga   49200
aataactgca tgtaaaatgt ttgtgataaa gataattgaa cacagtaatg aaaaaaaaaa   49260
gaaagaaaca gtatggagat ttgctcattg aactgagctt ggtcattctc ttagttaact   49320
cctgtccaaa gtgatgatgg aattttatt ctacttttc atagatccga gtacaggtga    49380
cattgttcat gacacactcc accactaatt tcccatcttt caattttctt gttattgtgc   49440
tttccttccc atcccactcc tgatgctgaa ccaatgcacc atctgtaaag ttgcagacag   49500
tctgtgttt tctgccatca gctgtggttt cttcaaactc atctcccagg gtacaagaaa    49560
actgtgttgt tttcaaagtg ctctcggttt ttgtggtgag gtttctgcca tcacaagtga   49620
tgatacaatc tggcttggcc attgcgccca ttttttgcaa agctattccc actcctagct   49680
ccttcatgta ttcatcaaag cctttgctgt ccagcaggcg ccatcttcct tccagctgct   49740
gaactgtggc catggtgggt gcgggcgggc tggcgtgcag agcagggtct acgtcggcat   49800
ggcagcatgc tgtgtctgta gtgttctttt tttaaaaaaa ccatgctgta tcaatagttg   49860
cattgtcatc acatattcag attttatgtg aatttctgca tttaactagt cttctaggaa   49920
gtgctgacca ctgatactca gaagagtgaa ttgtctgttt gcttcatatt tgcctaatac   49980
atatcccagg aatagcacgt cacacttaag acttcccttt cccatgtcag gatacacaac   50040
atggtacggc acaagcggtg taggctttaa aaaccgggtt tgagttttgg ccctgtcgct   50100
gcagggatac ttctgaacct ggtctgagaa gactcacctc atgctgcaga tggcagtggc   50160
tcagagcaga ttctggagcc agcccatctg gggacgtgct tcagctctac ccgtcactag   50220
ttgcgcgact ttggacaagt tcctaaacct ctcagtactg cggttttgag acttacctct   50280
taggtttggt gtgagtagca caatgcctag gacagcacca gccatgttgc aagtgcaaag   50340
taaatgctac ctgttattgt tgttgttata aaaacaaaag gagagcagag aagtaccatt   50400
gaaatatttg gatacttgat ttttaaaatt ctgttggcag tcacctgcca acagataagc   50460
tcctaagttt tcctggtggt ccttgcagtc ccatttttc cttgggtctt gggccaagtt    50520
gaatgcattc tgattgcaga tgagctcccc tcttcttcct ccctaattcc agatgggacc   50580
cttggctctt tttgtattta ttctgggatc actgatgcga atttcagcat gcagctccag   50640
tcacatcatt ccactgctca ttacccctca gtgacttcgc atcaggtgct agcttagcaa   50700
cactttagct ggctgcttga gagccttcag gctgtggacc catccagccc tgcagccttc   50760
cctcctctcc ctcgagcatc ctgtgtccag agaagcctgg cttttgatgt ttgcctgaat   50820
acatcatgct atcctgcctg tcgtcttttt cgagcttctc cttctggtag tgtccttccc   50880
ttcacttgtc aatagcctat ttgtaccttg ggaccacctt tgattacatc tcctgcatca   50940
gccacttttc tcctgttaat aagaggtatt aacatcatta cccttggagc cagcagagca   51000
ctaaaatagg gaggatgcta gcagcagctg cagaccgcat gccagcaaca ctcaggatta   51060
cggagagtat ttcaggagtg cagcgagttt cacagaagtg cacaaccccg tacaggcatt   51120
agtatcccgg ctttgccagt gaggtaacag acagtggaga ggggcttata aaagcccatc   51180
tgtatcagag ccggaagtca agccttggtc tgttgccatc tgcttcacga ttggctgtct   51240
cttgtacctg ttttggggaa gagctactct ttagtccctg aagccgctgg aggaacgttg   51300
agaatctcac atgcggggtt tggaggtgga gtccagggtc ttgagagcag tgctgaggag   51360
ggaaaggctc ttggctgcct gttacctaga ctccctggac tggctttcac aggctttcct   51420
tgatcctggg tctgtgggat tcttgccatc ctgtgttgca gatcacaggg atgacctgcg   51480
```

```
cgtcctgtgt ccacaacata gagtccaaac tcacgaggac aaatggcatc acttatgcct    51540
ccgttgccct tgccaccagc aaagcccttg ttaagtttga cccggaaatt atcggtccac    51600
gggatattat caaaattatt gaggtaagta attcattaaa aaattgtagt cacctttttta   51660 aaaacagtaa tatataatca gtgaagaaaa atgagaaaat atagctaaga aaaatgaaa    51720 ataaccaaaa ttcttcaact tttcccatgg aaataagctc agtcatttta aaataaactg    51780
caggtaagta aataataaat aatctgaggg aggatatcag tgaatgggta agagaaagat    51840
gaggaaaaga cattattatt gttttaattt tagatattcc ctaagaaaca tcaatattgt    51900
caagataccc tgtacatagg gttaaagtgc ctaattgtaa ttttttaagtg tgatctttgc    51960 ccaaacgaag tatctgtaga gcaaaggaac gttggccttg gaaaaaatga tccacatttt    52020
gccactatgc caggccactc ttgttgtgga gagcttggcc gcttctgctt tggaaaatcc    52080
gtgagaattt tcatgcgtgc cctgcctctt actcccttcc cagtttgtcc acagacatgc    52140
tatttccttt ttacattttta tacaatacta ggctataaga gaatgagcat cagtggtgat    52200
ctgaatgggt taaggcagtc aaaactgaaa aagattaact tgtaacagct agtaaggata    52260
aattaagttt agtgggaact acatgttata aaatcgctta tgaaatgaag cctcttatag    52320
caggcttaat gtagtatcct gaatttcctc ttcattgtgt gtgtgtgtgt gtgtgtgtgt    52380
gtgtgtttaa agagagatgc tgtctgttat gtggcctggg aaagcttttt ttttctttct    52440
ttttttgaca gagtctcatt ctgtcgccca ggctggagtg cagtggcatg attttggctc    52500
actgcaacct ccgcctccca ggtcaagaga ttctcctacc ttagtctccc cagtagctgg    52560
gactacaggc gtgcaccgcc atgcctggct aattttttgta ttttttacttg atggtgtt    52620 tcgccatgtt ggccaggccg gtctcaaact cctgacacct taggtgatcc acctgcctgg    52680
gcttcccaaa gtgctaggat tacagatgtg agccactgtg cccggccttg gagagttttt    52740
tttttttttt ttttttttga cgtggtct cgctcttgtc ccccaggctg gagtgtgatg    52800
gcatgatctc ggctcactgc aacctccgcc tcctgggatc aagcgattct cctgcctcgg    52860
ttccccgagt agttgggatt acaggcacct gccaccatgc ctggctaatt tttgtatttt    52920
tggtagagac agggttcat catgttttcc aggctggtct agaactcctg acgtcaggtg    52980
atccacctgc ctcagcctcc caaagtggtg ggattacagg catgagccac cgtgcctagc    53040
cccgggaaag cttttttgaca tggaaatgat catgctgctg atggtccagg ccccaccct    53100 tggaggcaga cagcatagct ttttttatcag ctgaggaaag atgctcagag aggttaagta    53160
actttactca caatacccag ctcacggaca gcagaactgg tgttcaaacc caggtcttgt    53220
gcttccgagc tcagtggcct ttgtgagtct agtacaccac aaatcttaaa gaacagtagt    53280
gatatggcat tgatgaggct cagacatcag actgatgcag tcaacagcaa ggagagtccc    53340
atgtggtgct tttgaacaca acttagtcac catttctgat ttctttctttt cttttttttt    53400 ttgagttggt gttttgctct tgttgcccag gctggagtgc agtggcatgg tctcagctca    53460
ctgcaagctc tgcctcccgg gttcaagcaa ttcctcctgcc tcagcctccc gagtagctgg    53520
gattacaggt atgcaccacc acgcctggct aattttttgta tttttagtag agatgggtt    53580 tcgccatgtt tgtcaggctg gtctcgaact cctgacctca ggtgatccac ctgcctcggc    53640
ctcccaaagt gctgggatta caggtgtgag ccactgtgcc cagccaaccc ttttgatt    53700 ctgatacctc acttgcttct atgctaccca gcctgctaag tgtggtgtgg catccatgct    53760
gaccttattt ggggactatt gctaatgtct gtcctccatt cttgcatctc tgggccatt    53820 tttgctaata taattaggct ggtattactt gtaaaaggat ttgtctttag acagtctcag    53880
```

```
ctgctcttcc tcccacccca acttttaatt tttgtgtaaa agtcccagca ccagagttct   53940
ggggcccttc tcttaattgt gctaccagac aagagcattc gtggcagttt ttcctgtgtg   54000
tattcataaa gagtatcaga gatatagtgg tcagatgaac gtggtaacaa agcgcttgag   54060
ttaaactgtg agcaaagcac aagattgcgg tgtaggctct gttggggcac agtggaagct   54120
gtgcttccaa atgctgaagg agccgagttc tgccgcagtg caagaagcc tgggctggaa   54180 gctggaggct ggagctctga gtccagctct tctgagaagg gtggggcttt gggcaaggta   54240
tttatcctct ccgaccttct gtttcctcat acatggaatg aagatttctg accattaggt   54300
atctgggatt ccttcactca aaaatgctga gtttaaatta taagtcagca ctgctcagct   54360
ttggagtctg gggaagctgt cttcccagaa gtgctgaact tctgcacagg gtttgtaggg   54420
ctattgggta aagaagttgt aagcagaaaa cccacaaagt ctactgaggc acttttagat   54480
tcactttcta atttccaaag ctgaaaagtg ctttctgcca atgcatattt taaccaagta   54540
ccttcctcct ttttccccac ccctctcttt taatgacaa ggaaattggc tttcatgctt   54600
ccctggccca gagaaacccc aacgctcatc acttggacca caagatggaa ataaagcagt   54660
aggtagaaca caaagataa actccagctc tcatctaagt cccttcctct acctgggccc   54720
aactctgcca gctggtcttg tcttcccatg gtgccttcct cctggattag ctgcctttac   54780
ccttgtaatg tgaaccctct gaaacagtgc tgtccaaaag aagttctgga atgatggcag   54840
tgttctgtat ctgcactgcc cagtgtgata gccgctagtc acatgtagct agtgagcact   54900
tcaaatgcag ctagtgtgac tgtggaaatg aattttaat ttttaaggaa tttcaattta   54960 gctacctta gctaacagat tggacagcac ttaagttggg agggagggag agagtgtaga   55020
ttttttttcc tttgacaatg ttttcagact ttatttgcat gggttctaga actagaattt   55080
gaaggcaggc ataatggctg agtggaaaga aaatggccca ggcgcgggag acctgagatc   55140
attcattatt tcagatggcc agttactcat tcagcaccat aaaggctgct gttgtgtgca   55200
gggcagtgtg ctaggtgctg gggataaata ctttccctgt ctcggagggg cccatagtct   55260
ggctgagaaa gagtgagtga gcaatgaaat caatggctct ggcagattct ggaaggtcta   55320
ggaaaactcc aagcagggga cataagatct gagcctcaaa gaatgagtgg aagtttgctt   55380
ggctgaagga attggtggcg gctacccttg gggactgctg tggcttggtt cagtaggcat   55440 gcctgggca caggaggagc ttacgggaga ggcatctgaa cagccagttg ggggtctggt   55500
tcttgggtag cagtccaaca gcctaagact tcagcctcaa aggccagtgg ttttcatgtc   55560
atgttttagg tgcatttgag gttccacaac cactcggttg gaatttcatg gatgctgcag   55620
ctaacatgag accacagctg tcagccatga ccccgattc caaactatgg tgttcattga   55680
gacagccagt gatcactgtt ctcatggact ctattttaaa taattgttta aagatagaat   55740
gtataagttt atactaataa aatactgctt ttatctattt ttttctttgg gggtctgtat   55800
aagattgcat tttgaaaaga aagctatagg caaccatagg ccgaggatgg taggcacctt   55860
tggggctaga ttctcagctt tggggcctca cttgcctcac ccgtaaattg gaggtaacca   55920
cagtatgtga aggcagggc tgggcctcaa catctttgga acctccttat agtgatgttt   55980
agacctctag atgctccctc agatggccag tgtcagagag agagagttct tactttcatt   56040 ttaaccctg gtggtctgtc ccagacatgt gacaaaggca ggtcttaaac tgtgtcctca   56100
gaaggggagt ggcttgtaat ccaggtgaca agcagcatct gatatatctg tgttgctgca   56160
tttgctttcc aggtggaaga agtctttcct gtgcagcctg gtgtttggca tccctgtcat   56220
```

```
ggccttaatg atctatatgc tgatacccag caacgagccc caccagtcca tggtcctgga    56280
ccacaacatc attccaggac tgtccattct aaatctcatc ttctttatct tgtgtaccct    56340
tgtccaggta tatatgagaa agtgggcaga cctctccctt ccatgctgtg tgtggccctc    56400
agatattctg cccgctaagc gcaaacatag tgctttagct tggtttaaat ggcactttat    56460
tgcagctttc ctgccccacc caggcagttg ctgctttttt tctctcttaa tgaccagtag    56520
gtggggcttg gggcccccc agtgtggggg actactaagg gcctggtttc actgtcagtt    56580
tcagttgatt gcaagtgatc agaactggcc ctggaatagc aacctccttg ctgcaaggtg    56640
tggtgaactc tgtgtctcca atgtgcatat tgtttaggtt aatttacgtt tgttgctgga    56700
agcaacaact ggatcaccct tgagcccatg ccactcttga gtgttctatc ttaaaaggtg    56760
gagatatggt ccttgtcttt caggaagtta aatttaaaa gagaaaggca tgaaacgtct    56820
gctttggtgg tgatattaag gaactagctg tgtgtctggt gggaagtgtg ccctctatgt    56880
gtatattttg gaatataaaa ctaaatccct gtcctaatat tggaatgttt aggggctatt    56940 tggggggcaag cattggtagg ctggattttt tttttttttt tttttgaga cagggtctca    57000 ccctgtcacc caggctggag ttcagtgatg tgatcatagt tcactgtagt cttgaactcc    57060
tgggctcaag cgatcctccc acctcagcct cctgagtagc taggaccaca agcgcctgcc    57120
accatgcctg gctagatagg gtcttgctat gtgcccaggt tggtctcaaa ctcctggcct    57180
tcaacagtcc tccaagctca gtctcccaaa gctctgagat gacaggtgtg agccactgca    57240
cccagcctga atttgtgttt ttctatattt tgtttgatta aagtgtaat gtacacttat    57300 tattaacaat tcaaaccgta ctgaagtata agaagaaaag aggaagatgc cctttcactg    57360
atcacattct gcctcccgcc caatctcatt ccccagtgtt gctatggtga tattaatagt    57420
tgggcattaa tctctccaaa tctttatata gagaaaatgc acacttgcgt gtatgtgtat    57480
gtatatgttc acgtaataca gatacagact ttttaactg aaatgggatc atacaagata    57540
gactgatgtg cagctggctt tttcacttaa ctatgtatta gacatctttt atgccagtgg    57600
gttatagata gagcccattc tctttaggga atggaatgcc ttgtgctgtc tacagtacaa    57660
atgagtcgta attttttcc ccaacttttc accattctct tattagagga catttgtgtt    57720
gtaagcactg ggttttaaag gtctcacatg ctcttggtca tccattcctg tggacagtag    57780
tcctctgaat gggaaagtat atttcataaa cgcccatcac agaggaagaa gtactgtcac    57840
gactgtgcac aaagctagag gctttgccat ccccagggcc cttggccctg tgtcgctcat    57900
tgaactctcc tccctacttg ctggcagcct tcactgtcct tgtctttcag ctcctcggtg    57960
ggtggtactt ctacgttcag gcctacaaat ctctgagaca caggtcagcc aacatggacg    58020
tgctcatcgt cctggccaca agcattgctt atgtttattc tctggtcatc ctggtggttg    58080
ctgtggctga gaaggcggag aggagccctg tgacattctt cgacacgccc ccatgctct    58140 ttgtgttcat tgccctgggc cggtggctgg aacacttggc aaaggtaaca gcagcttcag    58200
gttcagaaaa gagctgctcc ttcagtaaac aaatctcact tcctctgaac accatgttta    58260
gaattactaa ttatacacag catagagaca gacttaaaga aataggaaac ctccatataa    58320
ttaaggtgct ctagtcacta atctccaaat tggtcactac ttctgaaatc ccagctaatc    58380
tggttaatta ttaaaaccat cattcaggtg tattgtgtaa actaaagaaa cctggccttc    58440
agggcagagc ctacattgtc tcttggtgca aaactgaata tgtagttggt ctagacatcc    58500
atacatcctc ctcaaggtca tgccattttt aacacccttc attgtcccca acactgaaat    58560
gtatcttaca agagaatgga actcaggccc taaaagaaat tagattgaac ctaaaagaaa    58620
```

```
atggtcagtg ggaagactga tgtttgtttc cagtctgaaa tgtaattccc ggactttagt    58680
ggcacaggca ctgtgcatca ctgtggaagt gacatgtggc catgtgtggt ggatagcaag    58740
taacgcccac ctgcagagcc ttttatcgtg ccgtgcggct gtttctctcg caccagctgt    58800
ctctaacacc acgcttgtga ctctcaggct gggtttggac aggtctgctt tcgatagctc    58860
tcatttcaca ttctggttat ttcctagagc aaaacctcag aagccctggc taaactcatg    58920
tctctccaag ccacagaagc caccgttgtg acccttggtg aggacaattt aatcatcagg    58980
tgagttatgg ttatcaaatg tctttgtggt tggtatctat caatctgtgt gagctgcatc    59040
agatgcccat gttgtattga cattgcaata gaccttgtga gtgtgggcag agacacagta    59100
agatcaccac tctcaatcca gctacgaaag caaggcattg aactataaaa ctagcaagat    59160
ttgtaggtgg tgtgtgtgtg cgaaatggca catgggaggt gtagatgatt agtattccag    59220
gaattaagaa gaggaaggcc agtgttggtc aagggaaact tcacagagaa catagagtat    59280
gaattaggcc ttcctagtaa gatacacatt cagacaggca gagagataag gacttcaact    59340
tgctaaagaa taaaaattga aggagaaatt tatcttcttc ttaaggttgc ctgatattaa    59400
aaataataat tattattatt cctggaaact cttgttgcat ttattgtttg ctagacacta    59460
ttctaatctc tttgtattta atctaaccaa agatggaaac tttctgaggc agggactatt    59520
attactctta atttacagat gaggaagctg aggttcagag aggctaagca actgcccaa     59580 ggtcacacag gtattcagta atggaattgg gatgtaaccc aggctggtgg atccagagtc    59640 tatttttctta acctttacac acactgactc ttaatgcata tttaataata tggaaatttt    59700
tctaattaag gcttctgtat ttccttgggg ttagcttctt ttttatattc taggcaatgg    59760
ttatttcagc cctccttcat attcctaaaa tctctccctg gtcccaccac attttctatt    59820
agcctgtggt ctcgctttgg actactggaa ggagaagtgt tcagatggaa accctccagt    59880
tccctgtccc tcagcctaca cagctagcct cctccgtggc acctcccgct cctgccccgt    59940
tggtgggaga ggcgtctcct ccaatgcctc tacccgggaa cctttctctg ttggttttct    60000
cagtggtttt tggtgtctct gattcttatc ctccgatgtc atgcagactc taaccactcc    60060
cattttcaga ggcgttgtgc cttgcccctc ccttgtgtgc ccttgtccat gtatcacact    60120
gttgatggag ccagcctgcc ctagctgtgt cctggaggcc tgggcgtgaa ggctgagaca    60180 gacccccttgc ttccccatgg ggtctgcagg gctggtgcag ctggccctgg gcacgcccca    60240
ggtgagtaga ggaactgacc ggggccacac agatgcatga gtgttcatga ggtgcaggct    60300
ggctgctgcg cggtggcact ggttttgttc tggatcctgg cttttaaatg atcatcacaa    60360
ttgtaggact ggcaactgag atttgagtcc ttctggtgtt ccaggctcac tccccagcac    60420
ttgccacaga tcgtctagtt ccactctgta gctgttccgt gaggcagcac tgtcatcatc    60480
ccagctttcc tcaggaaaag ccaagtgcag tgaggtggag taatatcccc agagtccatg    60540
gcaggcagga agcagagctg ggattggaac cctggaggca cagagccccc ctcagccact    60600
gtgctgcgct gccccaaaac aggaccctgt gtgacggcac ctggcatgct gggctctgct    60660
gtgccatggg tctgcagcag tcacatgcct tggcttcttt ttttttttctt ctcttataaa    60720 ttaattgcat gaaagtttct gagaagtgaa aacgttcaga cagggagcca agccgctggc    60780
agctgtgttg gttttgactc atgtttcctc caactcgcct tgctagggtc ttcggtacag    60840
tttgaggcgc ctctgatggc actgactgca gttgcttgga actattccag ggatctgaac    60900
aggaggagaa ggcatctgcc ggccgaagtg cccacggggt gcgtgcagca cctgtcataa    60960
```

```
ctcagttctt ttccaagaat gccgattcat tttttggctg gggacgcacg gcctgactac    61020
taccatgcaa catgacagga cattattaag ctaggggcca gaagaccaga gttcattctg    61080
cctttggctc actgtttggg tgtggtcatt cctacttgcc tcctgacagc acaccccgag    61140
cccaaccctc tgtcccaggc caaggctgca cccactgccg cctggattgc cgcagtctag    61200
gcctcccctg agctcaacca ttctgtgctt tgaggtgcac tggacactgg tttcccagtg    61260
actctgcctc ccacagggcc ctcccgcgtc tgggcctctg cttgtgcctt tggtccatgg    61320
caccatctga aggcccccag aggttctcgc ataactgccc tctttgactg aggcttgggc    61380
ttcttcctct gaccatccct ttgctgggga cacttgtgct ttctctttac tccaagtctt    61440
gggtgctggc agcgtttcta ggtgcgatcc gtctggcaca ctgtagtttc cttgctgctg    61500
ctgctgctta gtctccatgg gctttcttct ctcctttttc cttgtggatg gtccttgggg    61560
ttctggtggt actgcctctg tctttgtgtg ttacacaccg tcactgggac gtctcactct    61620
cccacgtctt tggttaacag ccgtgagaag ctcattctca aacctacgtc tagatcccag    61680
agactacctg ctggttggag tgtttttctt ggttgactgg taaaggctca gactcggcct    61740
gtctgtattc ttcttcacct tcccccactt ttttccccaaa aatattcccc ttccttggtg    61800
cctgtctgtc tcaggcaaag gtaccctcat gccagctccc agtgtgtcct ctacaatgcc    61860
tgtctgccct cattcacaca tctgcagtcc atcctcatgg ttctagcacc tctgtctcta    61920
ggggcgtcat ccactggcac catgctggtc caggccactg tggccttgcc cctaaaacac    61980
cgcagctgtc tcttcatact gcttgcagcc atttatcaat ccagtatttt tccacattca    62040
aaccagtgat cttcctgaaa gcacaaattg atcatattac agtgctttct gaaagcacaa    62100
attgatcata ttggaaaatc cttcaatggc tgcatgctgt ccttaggatc aaaaccacct    62160
tcctaacgtg gcagtgaggc ccggcatccg cctgcatgcc tgttgagccc agcctgtctt    62220
gccatcccct gcgttgtgct ccagctgccc tgcaccactg gcaggtccca ggaagggact    62280
gcctctctct gcagacctct gcacacatcc ttccttccct ctgaactccc ttcttcctta    62340
acctttgcct ggctccttgc cttcagggct cagcatggaa gttgcatcct ccagaagcct    62400
ttcctgattc cccaggcctg gctcagctgt ggctcctcag tgctctcaga acactctgtg    62460
cctcagccac cctgggatgt aaacatggcg ggtgctgaga tactcactgg tggaatgaaa    62520
ctgctgtcag atgttaaaga acatactgc acacatgcat gtgtgtgctt gatattaaaa    62580
ggcttgcaca gccccatccc cagtctccca tgttgaaatt ttctggtttt ttttttttt    62640 tttacaattg atggggaaac aaattacaaa tcatatctag accagtgacc ataatgctat    62700
aagttttttc tttgttttct taacttgtgt ttaatgagga aggggagtag aagagaggag    62760
acaagtgaag taaacagatt cctggcagaa actcttaaag atgaagtgct atgaaacaaa    62820
ccactgtctt ttaattaaga gggttcctat cgctcagcac ttggagagga atagtagctt    62880
ctgaagaata catgctattg agattcacca gtaggagcca cattaaccct cataaaggac    62940
tattccttgt aagctgctta gagttagaaa gatgtggtta atttagatca aaggagaaat    63000
tcaaagttag atttaacaga gattagcatt actaaagatt tcttagaaag acacccaact    63060
gtacattcgt gccaatttta agtctcctta cagaagtgga catttaaaa cttagtgatt    63120 aggttctgct ggaggagggt ctgacccttta gttcttgggg tctttcattt ctaaattgaa    63180
tgcagggagc tcctcctccc gacttgggct tctcaggcca tgtggagacc tctgtgggat    63240
gataaatcct ccaggttgtt cagagggggc ctcaagggca atgttcagcc tggacttctc    63300
catcgctgga ggactttaaa attaagcaga gaatattctt gggttctcga gatccttccg    63360
```

```
ttctcctggc tcactcagcc accaaacaga tttacacagg tatactccca gcactaaaga    63420
cttcagtctt tgaaagtctc cttttcagta ctccatttat tttggttgcc atgattgaac    63480
tttctgtgtg tgtcttaact gtccatctgt gtgtctgctt ttagttatga ggctataaac    63540
ctcctgagag gaaggctcta ctctgtcctg tttgtaaccc cagcctaccc tggtgcctgg    63600
tacacaagag gccaatcaat atgaaaatgt caattaggtg ataataaaaa tcaccagcat    63660
tcattgggca cttactgtgt acaggtgcca tactaagcat ctcacgtaat cacaggaagt    63720
agccacacaa gccttgaatc ctcgtagcac agagactgtt cctgaacaat ttttacaaag    63780
gaaaataatg atgcaaatat ttaacataca tgcctgcata tggtagttac taagttttat    63840
atagttgtac atagcaacat ttaaataagt gggcatgtat gttcaatttt gtgcctttct    63900
aagacatctt caggttttgc tgaaatgggg gtaataagac tcaccttgta tgtgtctggg    63960
aagattcagt gaggtaaaac atgtaaaaat ctagcacagt tcctagcact cagtaaatgt    64020
ctatttctcc ttctcaagta agtaagatgg cttttgtgcc tgtgatagtt taaatgtagt    64080
ctttgtagaa tgaaagcaag gtgtaaaata acctcagagc cctgcttgct ttccatgcat    64140
gctcttctgg cttgttgacc attagctcat gagccagtat tacctataca attaattctg    64200
ttgggcccat gccatgcttt tagtgagctg ctgctgaagc tggccctggg ccgtaggtgc    64260
cctccctctg gctttgtctc tgttcctgcc gtcttctcct ctcccccgc agcatctctg    64320 tctctgcagg acatgtccca ctagcacaca gttcacatgt atgtacaaga cacaatcccc    64380
actttaatcc accctcccct ctactgctct gttttctgt tccttcacaa agccttctt    64440 taaaaacgtg actttcgctg ttgtctttgc cttctcactg cgtgctctct cagcccattc    64500
tagttgagcc tctgccttta ccagtttctg aacttggttt ggccagtgcc atcaagtaat    64560
ttccatatac cccaatccaa cattgcttgt gttaagtcct catttcagtc tctcaccagt    64620 atttcccct tgtctgtttc tttgattttt ttctttttt caatgtgtaa ctcacagtca    64680
ctgcaacaca caaaccctac gtgtagagtg tgatgaattt tacgtatatt tgcccctgtg    64740
gaactacttg tgcagcgttt ggtgtggttg gatgggtgct ccctcctcct cctcctcatc    64800
cccactctca ttttcctcct gtgtcactgg ctggtccttc agcttctgct cagctttcag    64860
atagtggagt gtctcaggga tgagttctag gaccccttct gtgttttctc cgtcactcct    64920
aggggcgctt atatgatctc atggctttaa atgctatcta catgtgacag ctctcaggtt    64980
tgttctctac ctctgacctc ttctttccac ttcagactca tattttcagc tccctagttg    65040
gcatttctac gtgaagtca aataggcatc tcaaacccga catgtcaaaa tgaaccattt    65100
ctctccatcc cctccccttc tcttccctca ccctcccttta gctgcttctc cataatcatc    65160
tccatctcat taaatggttt ctctatccac ccagttgctc aaaatgaaaa tttggagctc    65220
atctttgatt cctttcttta ccctcatatt cagtgcattt tcacatcttg ttaacacatg    65280
atctaagaat atgctgtgta tttcttctcc ctctctctgt agtccaggtt acttccatct    65340
tccgcttggg ctgctgcaac agcctgactc tcccctcac tcctgtgatc atccctacag    65400
cccattctca tgcagcagcc aaagagatca cttaaatgtg aatcagattg tgtcactttc    65460
ctgctaaaag ccttacatcc aaaacccatg ctctgctcca ggagactcgg catgatctgg    65520
actctgcctg cttctctgac ctcaacttgc acgtcactta cttcctgcca gccttgcttg    65580 cttttcttgct gtttctcaga cgcacccttc ctgcctgcct taaaccttg tgtcagttgt    65640 tttctctccg tgaacttcct ttccgtgtgt gttggacctt cttggcatgc aggtctcagc    65700
```

| | |
|---|---|
| ttaaatgtta ccttcccaga gaagcccttc catgtctcct cctccctctg ccactctaag | 65760 |
| aagccctcca gtcacattat ccttgttttt ttcatcacag cacttattaa tatttaatac | 65820 |
| ctgattctat cttgcttgtt gtccatttct accacagaac ttgtcttcat gaggtagtag | 65880 |
| ggcctttgct gtgccattca cagctgtatc accagtgcct agaacagtgc ctggtattca | 65940 |
| gcagctgcac gataaatatc tgtaaatgaa cagatcaaat gaatactgtt gctcagtata | 66000 |
| agcaaataca gtgtaactat tgtaacagct ggcctagaac ctgacccggt gaccgaatga | 66060 |
| gtggccatgt gagtgataag tggcgtttgt tgcagggagg agcaagtccc catggagctg | 66120 |
| gtgcagcggg gcgatatcgt caaggtggtc cctgggggaa agtttccagt ggatgggaaa | 66180 |
| gtcctggaag gcaataccat ggctgatgag tccctcatca caggtgagat ggcttgtttc | 66240 |
| atgttccctc aggaggatat catagcagct gtcaggtcac atgagtgctg gatgggctg | 66300 |
| agcaagtgac agttgtctct ttcctacgtc taggagaagc catgccagtc actaagaaac | 66360 |
| ccggaagcac tgtaattgcg gggtctataa atgcacatgg ctctgtgctc attaaagcta | 66420 |
| cccacgtggg caatgacacc actttggctc agattgtgaa actggtggaa gaggctcaga | 66480 |
| tgtcaaaggt aatgaagaaa ttttttaaaac taacttcatc tttctcgttt tagaaattat | 66540 |
| gtgaagagtt ctgggaaatc agacagtttt attgagtaga gattgattag taaatgtggt | 66600 |
| taaatgaagg agattatccc aatctttatc catgcttgtg gtgttttatt tcttcatagg | 66660 |
| ttgtaattc ccatggtctt ggtgttttat tttcataggc acccattcag cagctggctg | 66720 |
| accggtttag tggatatttt gtcccattta tcatcatcat gtcaactttg acgttggtgg | 66780 |
| tatgattgt aatcggtttt atcgattttg tgttgttca gagatacttt cctgtaagtt | 66840 |
| gaatgccttg ggctatatgg tggttgtgtt ttaaataatc tactgacatt gatcctgttc | 66900 |
| tttcatatct tagattcact gggctttaat tattcattac attttatttg cttgcttctc | 66960 |
| ttattgacag caaaatctaa gccagagtag ataaacagt cactctcctt ctgcaggttt | 67020 |
| ctattaaaga tctcctttac attctactta gataattttc acagacacca attggtgctc | 67080 |
| agttgtaatg cttgaagcat ttacaatatg tattattggt ccttttttgag gttatgaggc | 67140 |
| atacatcata gaaaatagtt cactttaaat ctcaatggca tgataatatt atttaataca | 67200 |
| ttttaagaaa aatatctttt gatgtatata tttaccagta ccatctttga cctcccagct | 67260 |
| tcccaagtaa tgtaaatagc ttttttatgtt tgtttgttta tttatttatt tatttgagat | 67320 |
| ggagtctccc tctgtttccc gggctggagt gcagtggctt gatctcggtt cactgcaacc | 67380 |
| tccacctccc aggttcaacc agttctcccg tctcagcctc ccaagtagct gggactacag | 67440 |
| gcacacgcca ccacacccag ctaattttg tattttagc agagatgggg tttcaccgta | 67500 |
| ttagtcaggc tggcttcgaa ctcctgacct caggtgatct gcctgtctcg gcctcctaaa | 67560 |
| gtgctgggat tcaggtgtg agccactgca cccaggcgtg aatagctttt tataatagtt | 67620 |
| aaatatttac taaacattgt atgtgaggca atgaatata cattttgag tttaaaaaag | 67680 |
| tggttgaaga acactatctt aggaaatatg gttttattaa acctcagaaa aagaaaggaa | 67740 |
| aatacaggcc acccctcaaa aaaacatatc tgcttgagga ataaaagcta tattacatct | 67800 |
| gtgattctca gttggcagct gtgacatttt cggtgtttgt gactgggggg atgctgctaa | 67860 |
| acatcctgca aggcacatca caggccctac aacaaagagt tatctggccc caaatgtcag | 67920 |
| tagcactgag gttgaaacct tgataatgta cttaaaaagc taatggcaca cttagaacag | 67980 |
| tatttggtaa tggcacaatg agcggaacaa tgttttacc ttatcttatt cctagcccag | 68040 |
| tctagtgctt gttataccat agagccatag aatgagaaac catactgggt gtggtgatgc | 68100 |

```
acctgtagac tcagctactt gggaggctaa ggcagaggat catttgagtc caggagtttg    68160
aggctgtagt gtgctatgat cgtgcctgtg aatagccact gcactccaac ctgggcaacg    68220
tagcaaaaag tacaaataca gaatggataa ttttttttctt ttaaaaaaaa tccttcacat    68280
aattaaaagt atatcaaata ttctcaggac acatgtcatt tactaggatg tattttctcc    68340
ctcaaatttc ccatcttaaa ttgaacaatg ttcaagttaa acactttctg acatctaagg    68400
aacctcagtg ctcttaaaag taacttacag atatattggt agaatgtgcc tgtggctatc    68460
catggcacct gactgcctat aatttcggct ttttcgggaa agcagtgcgt tggcatatgg    68520
ccatgggaag actcagtcct aaacaagttg gaatctgtgg cttctgctg ttccatgcct    68580 ttccatctta ctttggcttc ttttgttttt atctgcaata tcagggagga tgctggcaaa    68640
tgaggtactg catgttcctt taagatactg tcatctctct gctgtacaaa agtcattgta    68700
gagaagggct catggtaact tccagaagtc cacccagtcc tatcagaatg ccaggtgtga    68760
ttttgacaag aattagtgta tttttaaaaa agattacata atcttatgt ctaaaaatct    68820 taatatatcc ctctacctaa atataactgt ttctatgaaa attaaaagac cccttaata    68880 atacattatt ttagaatcct gcctttcaga gtgaaataat aaaatgtaga tggaagctaa    68940
agaggctgtg gtccatagcc ttaccttaga caactgtgct ttttactata agtaagtgaa    69000
catagtatct cttgattata ctccatagcc accagccatt tttaaaaata aaccaagata    69060
attcaagctc tcagaatgca aataatacca agtgtctgga aagtaggtca tattttgttt    69120
gttttgggta caaagaaaaa atagtgaaaa atacagagaa gaaataaag atacctccaa    69180 atcatatccc tagaagtaat ttttttgcat attggtggat accttccag tattgttgaa    69240 atgctgtatt cagatacagg cggagatttt tgcacgaata aatcccagca catgcgattt    69300
tgtacttgct ttttaatttt gcagtgctgc tggtaccttt ccatatcagt atgttccatc    69360
atcattccaa tagttgcctc gtatcccatt atatacatca cacctacagt ttaattaacc    69420
aattccgtat tggttgtttc catttttttat cattacaaaa acaaaacaaa acactgtggt    69480
aaatatcctt gcatcttttc ttatttttat gattatcacc ttagaatagc attttaagc    69540 tttcctaatg atgagaaaaa taacgataat agttactgtt tcttaaatgc cgctcctatg    69600
ccaggtgtta tgtactgtgt atatttatat gtttatatgt gtattgcctc attcaatcct    69660
tgccacaatt tatgagctat gcattatcat ctccattttg tgtatgagga aaccaggatc    69720
tggatctgtg tggtccatct ccagagtctg cttttcccta tcaagggctt ttatttgact    69780
ctgctcctgt aatgcctctt tgagggaaac ctgtaggatg aagttggata gctgggatgt    69840
ggagagcagt aacgtgttct ctatgatggc agagcagtgt ggaataccat ctgtttccgg    69900
aacccaagtt cgtcacgttg tgtccagtgc ccccctgaaa tgtccttatg tgattagagt    69960
tctgggagct tccttattga actctcaacc tgcctctgac tctgtcctgt tttcagaacc    70020
ccaacaagca catctcccag acagaggtga tcatccggtt tgctttccag acgtccatca    70080
cggtgctgtg cattgcctgc ccctgctccc tggggctggc cacgcccacg gctgtcatgg    70140
tgggcaccgg ggtggccgcg cagaacggca tcctcatcaa gggaggcaag cccctggaga    70200
tggcgcacaa ggtcagcctg tagcacggct ttccccatcc tgagagatga aagtagtatc    70260
tgtttactat ttcacattga gagaaaagcc tgagagccac tcaagacagc agtgttaatt    70320
acatagaata ggaagtcaag tataactggg aataacaaca gtagcaacag agtagccacc    70380
agtcatataa tggaacgctt tatcaacatt acttgattta attgcattaa caactctgtg    70440
```

```
tggtaggtgc ttatcattcc cattttacag atgaggaaac tgcagcagga ggagattagg    70500
taacttgacc aaacgcctgc agctaaccag aggcagagct gggattcaca cccaggtagc    70560
caggcttcag gacaaaagcc ccaccgtgac atctgtggga ttagtggtgg gtcctgtgac    70620
cctggggagt gaagagtgag tgacggtgtt tgtgaagagt cttccttttg cccaacttac    70680
taacctctgg ccttccacac tttcacctat ttaatcagta tttgctgggc actcactgcg    70740
tgtgagccct gcactgggtt ctggcgatgg tcatggtttc cagccgccaa ggagcccacc    70800 aggggggaaag acagacagtg aaaaagtaaa tagcaaagct gactgagtat tacgagatac    70860
tgagtattga ctggtggtgc ttgacgtcct ggggacactt gaacaggggc caatcctaga    70920
cttggggtgc tcgactcagg gacaagggtg ctgcaggtgg tcagggaagc gaatacgaac    70980
gttcatctga gaccttactg ttgagtgaga gctggacaac ggagctgggg aagagtgttc    71040
caaaatgggg acagaaggtg gaaagcacct gtggaggtgg aacttcccct ccccgcggta    71100
tccccagcat ctaacctgag acatcaagtg cattcagaag ttatctgttg aatgagcaaa    71160
tgaggaactg gaagaaaatc attgagagag aggaaccaga gatgaggccg ttgagggagg    71220
ggccagaatc caaaggctga agatttagta aagtgttctg aacgttagcc tagaagccac    71280
gtaggggatg gcatacccac gtgatgtgac tggatcgtgt gttgggaaga tcattccggc    71340
tgcagtgtta aggttgcgct gaaagctggc aagaatccct ggaggaagat gagttaagtg    71400
tgttgaagga aggaaggcca ccgctcagca tcagaaacaa aaagctgaat tattgtttgc    71460
ttgtaaggga gaaccctgct tgtgggacat ggtctgagaa gagcaacctg ctggccttaa    71520
atgggtaaaa ttatacactt caggaattac tggactttca gaagcagggc tcagggctcg    71580
actggccctg gtcatggaag tgcaggtacc tgaatgtagc tgctgcccat atctgagccc    71640
agaggtgtgg ggactctgca gactgccatt gactaagtgt gaccaactta aaactggctc    71700
tgggggtttg tttgtcatta tggccataga atagtccttt cctttcttga actcagagtg    71760
tgaggactct attcccagta gcttttgcac ttaggcaggc aaaaggaagc tgaggttggg    71820
ctcggcggat ggcagtggac agggaggcag gtgtccctca gggtcctgac tcctgacctg    71880
atgtggggga gtatgtggat ggtgtcactg tctgggggac agtgctgtgc catctcctgt    71940
acagccgact gagggtttct ggctttgcct ggtcaaggtc aagcctcagt gtggctggtt    72000
tgactggaca catagggaaa cagtttcttt gcagtgggag ttgttgaacc ctgagattga    72060
acgacagagg atcacgttag gaagctgtgc aggtgtcttg tttcctgtct gaggcaggtt    72120
gggtgaagtt ctgcctcagg agtgtgacta tggaagcccc tccatctgta ttgtggtcag    72180
tgagttgtgg ttgtttttgg cagataaaga ctgtgatgtt tgacaagact ggcaccatta    72240
cccatggcgt cccagggtc atgcgggtgc tcctgctggg ggatgtggcc acactgcccc     72300
tcaggaaggt tctggctgtg gtggggactg cggaggccag cagtgaacac cccttgggcg    72360
tggcagtcac caaatactgt aaagaggtac gtggacttgg gcgtggccct gcctcccccg    72420
ccaatgctct tttattcctc accatgtcct tctctcctag ctgccctcga ggagccttct    72480
ctgtgtggtc tggaaaacca cttagagggc ccttctgcag caggcggaga tatagggctc    72540
acagtcagcc cttgccacag ttccaggtta tcacaaaggg agttcagtgt cacaggcatt    72600
tgctgaacat caccaggcgc caggctcagg agaacaacag gagtgggata tgaactctac    72660 ccttttgggag ctcacggtct tggggagtac gggcagtctg gaaactcagt gctttgacag    72720
tgcttagtgc aaggggacac aaacatgaaa tgggagtact ggggtggaag ggagaaatct    72780
actcccctgg gagcacctgg gacagagagg aaccagcaga ggtgagccag agtgcccagc    72840
```

```
aggttcctgg cacttcgtgg agaagcattg ccttcttttg gtctctccac aggaaaggtt   72900
ctattttgtt ttctcttaat ttcagtctga atataggggc agcagaacgc gtcacacaga   72960
atattgccct gacaactttt aaacagcctg agcaatactg ttagcagtaa atgtagaaag   73020
gtgacatcat tgccttgaaa aacaattgac aactcttcct gatcagggc tcttccagaa    73080 acctcatttc tagttttgtc cttcatgtag ggtcagacag cccactcttt ctcacctcac   73140
ccttctgaca tttcagggag aatcttgctc accctcagtc atcctttatt tgttgtgtgg   73200
tctggaaaac cgcttagaag ggtcctctgc agcaagtgga gatgaggggc tcacagtcag   73260
cccttgccac agttctaggt tgtcataaag tgaggtcggt gtcacagcca tttgctgaac   73320
atcaccaggc gtcaggctca ggagaacaac agaagtggga tgtgaactct acccttgggg   73380
agctcacagc ctgggggagg acgggcagtc cagaaacccc agccattcct ttaccctgcc   73440
accttgtccc ctcctcctcc agggtctgat atacaggcag ttatctcttg atagtctcaa   73500
agagctttgt taacactact tattccattg tttttaatga aattatttgc aacataaaat   73560
tcacatctcc ctctctttgg catctgcagt cctctttaat ttgaggtgtt tgatatgagt   73620 tgccttttc cttccagtc ggtaacctgt tcactgtcat gaggcaccca cccagggaag    73680
gattttaggc tgtttaaaat agtctcattc aacttacagc tataatatct ttaccaaagg   73740
agggagaaat aattacaagt tactagtcac tatcttaacc tttcctatct gttccacctc   73800
cctcccctcc tttctctcag ttcccgcttt ccgctgctct cttgccacct tcaccctgtg   73860
tccctgtcct gcctgcccct ccctttcact tcacccctct tggcttacag tttcctcttc   73920
ctctctttcc accttcccag gaacttggaa cagagacctt gggatactgc acggacttcc   73980
aggcagtgcc aggctgtgga attgggtgca aagtcagcaa cgtggaaggc atcctggccc   74040
acagtgagcg ccctttgagt gcaccggcca gtcacctgaa tgaggctggc agccttcccg   74100
cagaaaaagg tattgctggc ttttgtctct gcagctggtt aaaagtagag gtgggtcaaa   74160
ccacagagag caccacgccc agcagtgatt gcctctgctg tgcggcagac ggttcatggc   74220
taaggcaccc aagcctgcct ccccacaccc aggaaagttt ctcttatgtt cttgggtgcg   74280
tctaaatttt gttgcttatg gctgccttaa attcatagag cattgtttag ctgacccatg   74340
attttgattc tcctctttct tatcccatat cggtcttgct tctcataagc tacagagtag   74400
acagacggga attccacttt cgttcttcct gtttccattc tgtatggtag aattctggta   74460
tttacaaagc aggcagaaaa agtcagggaa agcagaggga aatgtctgcc caagccagga   74520
agggacactg cttggaggga cagctgcttt tgaagaatgg cctttttat tctcaaggta    74580 gcttgccagc caccagaata aagggtggaa aacactcaaa atctgtgact agtgttttc     74640 ctaagtgttg gtagtgaaat tgtggcttag attgtgtggt tagaagccat ccaccacctt   74700
ccagccttta aaaccccagg atggcctttc catgagagct tccagagcct ggccgttcag   74760
tgacacctca gctagcagca cacgctgtta gaaagtgata ggtgagaggt gcattagcct   74820
cgggagttac agttttaaac atttcatgta gacgtgtctg attatttgtt gattcacctg   74880
gggttgttga taccaagcag taatgaatgt agtcaacact tgctttgtgt gctgggcaaa   74940
tacctgagtg cttctaatcc ctgcagaaaa agaatcagtg gatacttcta agacaaagac   75000
ggacattgcc ttatgtttaa tacgtttata ccatttccac ccatgtagca tgtactatta   75060
atgccccatc ttaattcata cccacatgtc ctacacatta attttacttt ttttttttt    75120 gtcctaaagg atgctgtcac aagaggtgct tacaaggtta cagttttca gaatggttaa    75180
```

```
aaggatattt tgctgttaaa aggattgcat ggttttagt tcacagtgaa attggaccat   75240
ttagaaataa ccacagcctc ttttgaatag atgcagtccc ccagaccttc tctgtgctga   75300
ttggaaaccg tgagtggctg aggcgcaacg gtttaaccat ttctagcgat gtcagtgacg   75360
ctatgacaga ccacgagatg aaaggacaga cagccatcct ggtggctatt gacggtatct   75420
tctgcttctg ccttccttcc gctctctcag aaatacagtt ttctgcagat atcaggcaaa   75480
agagtcctcc tttataaaag aaaagaagac aaacaaaagc cttcctctct taatttcagg   75540
cctgttttcc agaagattgt cttttgtct ttctcttca ttctttccac tggctccatc     75600
ttggccccag agcagctctg gtctggcctc agtctccttg accttggaat tctaaactgt   75660
ctgtgtcatc atcattgctc ttgtccaggt gggcagttca gagtcatcct tctccttcat   75720
ccctgcagac agagcaggaa ttcacttccc agcaggttta actacaggat gcatttaaat   75780
aatgagatcc atgccaccct tctctgtctg ctttatttat ttattattac tttcttttc    75840 ttttttagac tgagttcccc tcttgtcacc caggctgtag tgcagtggag tggtgtgact   75900
tgtctcacta caagctccac cttccgggtt caagcaattc tcctgcctca gactcctgag   75960
tagctgggat tacaggcccc cgccaccacg cccagctaca ttttgtattt ttagtagaga   76020
cggggtttca ccaggctggt ctcgaactcc tgacctcagg tgatctgctt gccttggcct   76080
cccaaagtgc tgggattaca ggcgtgagcc accgcacctg cccttctatc tgctttatac   76140
agactggtgt cgcacagagt acaggtctca agactgtgtg ttggccaggt gcggtggctc   76200
acgcctgtaa tcccagcact tgggaggct gaggtgggtg gatcacctga ggtcgggagt    76260
tcgagaccag tctgaccaac atggagaaac cccgtctcta ctaaaaataa aaaaattagc   76320
ggggtgtggt ggcgcatgcc tctaatccca gctacttggg aggctgaggc aggagaattg   76380
cttgaacccg ggagttggag gttgtggtga gccaagatca caccactgcc ctccagcctg   76440
ggcaacaaga gcgtaactct gtctcaaaaa aaaaaaaaa aaaaaaaaa aaaagactgc     76500 atgtgtttta gtgctcagat tctatcctgg gctttacatc ccagagagat tagagtcttt   76560
actttgttaa tgttagtttc tgctaataga agtaacagta tatgcaagca agaaataaaa   76620
tacatgacac cttttgaatg ctccagccaa atatgtcttt ctctcacatt ctctctcttt   76680
tttccctttt tctaagtctt tgtaaatcca cccgcccctc ggctatcaaa ccagaattgg   76740
cacaactaaa ggagtcgtgc cctctcgtat gtcatccctt actctgttct cattcacacc   76800
tcagccctaa aagccctcct gcttctatag ctaagattca ctcaaagaga aattctgccg   76860
aaatgttttc tgcaggaaaa gacgaaggat tgattttcta gtttggacat ttatcacttt   76920
aagtgatatc tgttatgtct cttgaatttt agtagctaat gtgtattgaa ttcttattac   76980
aagccaggca cttcgcaaag tgtcatacgt gctccttgca gaaagtttgg aaaattcagc   77040
tataaaggag aaaatgaaat cactcgtaat cctattcctt ggggagccac tgcgaagatt   77100
tcaattatat tgcttccaga cttttgtgta catccgtaaa tgcatgtact ttttaaaaag   77160
caaaaaaacc acattgtgtt atataatttg atgttttgtt tttgcacat aatattatat     77220 gatgagaaca ttgcaagtgt ggtatcttgg tgcggggtgc cccaacttgt gtagctgctg   77280
atgctggctg gttcgctcca ggtgtgctct gtgggatgat cgcaatcgca gacgctgtca   77340
agcaggaggc tgccctggct gtgcacacgc tgcagagcat gggtgtggac gtggttctga   77400
tcacggggga caaccggaag acagccagag ctattgccac ccaggtacag ccctttaatg   77460
ttgcaaactg tgtaaagctc ataaaagcag ttagagacaa aagtaagcac cagttggccc   77520
agcactgagc tgtactcctg ctctttctcc cttgctggat gcttttctct ccacgtgttt   77580
```

```
cattctgtgg ccatgtagtg ttgcacgtga gcactgtggt gctgtgcgaa gatctcttcc    77640
ctggagcttg ggcgcatgca tcctggaaaa aaggagttc  cagggttctc taaccgtttc    77700
ccagtctttg caatggaaaa aaaagtatgt gacctaaggg ctgagataga cattttctaa    77760
cctttatgtt aagggaagat tttgccagct cagctcttct cactggggtg ctcagataag    77820
tgactcctgg gcagttctcc agcagcccct gatgctgagt ttggtctgtg aggacagcac    77880
cactggatgg ctgcctgact tctcacacag cagcggctcc agtttggatt cctagaaatt    77940
atgcacctcc aaatgtgtgc agagctctag gcttctgaaa gcttaattgt gttccttgag    78000
ggaagcagca gtaccctgt  tttccatggt cctccttgct aattatggac ctgtttagcg    78060
tccttccccc cttttctggc tagcacttgt tcatctattc agcaggcact tacgaagcac    78120
cacgaatgtg acaggcaggt gtggggccag gctctgtgag gagtgaaggg gggtctgccc    78180
ttgacgggct catggtcttg caggaaggtg gaccagtgac tgtgtagatc tgagaagcgg    78240
gaaagggact aggaaaggaa aactgcacct tcccaggaca gagcaggcag caggagcatt    78300 tcccagggc  acagagtagc acggcggttt ggagatgccg cggggagctg aatggtatgg    78360
tcaagtgtgg caccagctgc cagaccctgg gaccctggga ctctgggacc ctcggaagca    78420
gacccaagag ttgagctgcc ctcctctggg agatgcatgg ggtctactgg atgtgaagca    78480
ggagagtagg gagggacatg gccggacgga tgctttggaa agaccatggg ggcagcacat    78540
ggagaagaca gttggaggac tgagccgtgg acagggagac cagcaagggg gttgtttgca    78600
catccagaaa aggacagggc ctaaaccagt gcagggtgtt ggggcaggag ccagggataa    78660
actggccctg tgacagcaaa cctgcagggt gtggttgacc aacatcactg actgacccca    78720
gaggccgagg gcagaggggg caagggtaac ttgaggtttc tgctgctatc tgataccttt    78780
tgccaacact aggcattgcc ttccttttgt cttaggttgg catcaacaaa gtctttgcag    78840
aggtgctgcc ttcgcacaag gtggccaagg tccaggagct ccagaataaa gggaagaaag    78900
tcgccatggt ggggatggg  gtcaatgact ccccggcctt ggcccaggca gacatgggtg    78960
tggccattgg caccggcacg gatgtggcca tcgaggcagc cgacgtcgtc cttatcagag    79020
tgagcgtggc tgcagccagg ctgtgggtgc tgggagggca atgggcagac cccttcctca    79080
ctgtgtgctc ctctccatca gaatgatttg ctggatgtgg tggctagcat tcaccttttcc   79140 aagaggactg tccgaaggat acgcatcaac ctggtcctgg cactgattta taacctggtt    79200
gggataccca ttgcagcagg taggcagctc ttacccactg tgctccagct gcgcccagaa    79260
aggcttctgt ctcccaggtt cctgctgggg ttagtgagtg gctcactcac tggctggcta    79320
gaggcgtttt agaaaggctg tttttttttt ttttcatgt  ccctgctttt atatgtcttt    79380
aaatgagaaa ctgtggagag gacctgaaac cttcattcac tctggtcctt tctaaaaagc    79440
tagtggagat gcttggctgt attttctgat ccctatttta ttgtggcctt attttctgag    79500
ccatttgtta agtcatatag tctgagaaat aatcattagt aagaattatg ggcatctgc    79560 tacatgctag gcacaattat tggtgtttca gaaccttatc ctgaacatta atcctgccca    79620
agtttcactc tgagttacac aaatgatcat ggaaagaaat ggctctttga ccaggcatgg    79680
tggctcatgc ctgtaattcc agcactttgg gaggctgagg caggagggtc atttgagctc    79740
aggggttcaa gactcacctg gcaacatgg  tgagactcca tctctacaaa aaattttaaa    79800
gttagctggg cgtggtagcg tacaccttag tcccatctgg gagtacagag gctggggcag    79860
aaggatttat tgagcccagg agttggaggt ggcagtgacc catgatcgca ccactgtact    79920
```

| | |
|---|---|
| gtagcctggg caagagtgaa accctatctc agaaaaaaag aaaagaaaa gaaatagatt | 79980 |
| tttctgcttt gtaattcccc ctcattcccc ctccttaaga accatctctc ccccgccccc | 80040 |
| tgctccctgc ccctgcccc caggaacatg gcaatgaaaa gttccagagt gctcctccat | 80100 |
| gggctgagga gagatcaagt ttgtaatcac agcattcctg cctcagtctc ccttgtgtct | 80160 |
| gagtggttag tggtgacttg tgtaacaggg ccttggcttc ctgagcccag tgagtcaggc | 80220 |
| aggtttactt cttgtcccca gagccggctc aggagcttaa ttcccccagt gtatgtgcct | 80280 |
| ctgccacaca aagttgacca tacctgtctc ctgaccctgt cctgggacct ggctctcatt | 80340 |
| cctcttctaa agatgtcatg aagccctgga ggcgagatca tctgctagag aaggactgtg | 80400 |
| gccctcagcc gtgtttgtcc tctgtgggac tgtggctaca ggatgggcaa ctggctccct | 80460 |
| cagctcctgc cgcttttctc ctcccgctcc tcccactcct tgtggtttgt cgctgccctg | 80520 |
| gagctcgccc tgaaatggga tgccacctgt gggtggttct gggaacatca gggcgagtgg | 80580 |
| aagagagcca ggcccactca acagcatccc acacccagct ttctaggaag cctcactttg | 80640 |
| gggggggcct gtgggcaaga tccattggca ggggcttctg agcacgccag gtggagacct | 80700 |
| cactgggggc cgctgagggt ggggcagccc ggtgcctgaa gccctctcct ggctcctctc | 80760 |
| cccagaccta ggtgtgagtg cgagttcttt cttccccagg tgtcttcatg cccatcggca | 80820 |
| ttgtgctgca gccctggatg ggctcagcgg ccatggcagc ctcctctgtg tctgtggtgc | 80880 |
| tctcatccct gcagctcaag tggtgagtcc cctcaggtgg agcatctgtg ggaggctccc | 80940 |
| aggaggcctt gtcattctgc atgcttagca cagtggaact tgcctctcat ttcccattca | 81000 |
| ttcacctggg acaaatgctg cagtggcagc ccacatggag cctggtgtgc atgcatgtaa | 81060 |
| cttatcagca ccatgagcag gcaattcact gctgcccatt cacgtgctgg gctgccctta | 81120 |
| ctctgctcct caagggctgt ttatgtgaac atcaagcaga catgggtccc tgtgtatgat | 81180 |
| ctatcacttt tttatttaaa aaagatgttc acttatttat gagtgcattc atttaacaaa | 81240 |
| agttagtggc agcctacaat gtgcaaggca tttgcttagg aagtttctaa atcaggtgag | 81300 |
| cttttcctgga accatagggga gtttaatgtc cttttccttg gaaactcttg aggttttgat | 81360 |
| actgaatgtt attaaaagat ggatgagagg ccttcaccag gcttagaaaa aaaaaaagcc | 81420 |
| ttgtttctag aatggctcag atgctgttgc gttcctgctt tccagctata agaagcctga | 81480 |
| cctggagagg tatgaggcac aggcgcatgg ccacatgaag cccctgacgg catcccaggt | 81540 |
| cagtgtgcac ataggcatgg atgacaggtg gcgggactcc cccagggcca caccatggga | 81600 |
| ccaggtcagc tatgtcagcc aggtgtcgct gtcctccctg acgtccgaca agccatctcg | 81660 |
| gcacagcgct gcagcagacg atgatgggga caagtggtct ctgctcctga atggcaggga | 81720 |
| tgaggagcag tacatctgat gacttcaggc aggcgggccg gggcagggac ttgcctccac | 81780 |
| tcaccacaag ctgagcagga cagccagcag caggatgggc tgagctagcc tccagctttg | 81840 |
| gggacttccg ctccctggat atgtccagtc atcctgccct gcagcacgcg gccttgtctg | 81900 |
| ggtgcagctg ggcttggcct ggagaggacg gccctgcctg cctcttggcc tcacgggacc | 81960 |
| gtcagcatgg gctttgtctt ggactctagt ccttggctgg actgtagaag gtgagaggcg | 82020 |
| agtcaccctc ctcacagacc tctgcttgga gtatttagga tgactgctgt gaaatggaga | 82080 |
| acagtttcat caggaccaaa aaacctcact gggcctttcc agagaactgc agacctcact | 82140 |
| gtcagggtct ttctgatgac gcctgtctgt gtgcatcatg tttctgagac cacagtttac | 82200 |
| ctcaggtgtg cctgttgctt tcttcctgca tagtctgttc cttttcttcgt acatagtctg | 82260 |
| ttccttttct ctcctgtgtg cttgtcagtg gggaccccctc gcaaccctgc ctgtcacctg | 82320 |

```
ggagggtggg accaatgtcc ttgtggtctt tgctgctgct ctcaggcgct tctccaatgc    82380
tctggagtgt gcatttcagc ttgaacctgc ttcctggctc acacatcccc agccagggag    82440
cttgccacac tcttcttcaa gttgaggaga gttctttttt gcttaaagcc cccttctcca    82500
tggagtgttg gcttctcaat agagtgttgt tgctgaccag ctggagtgag ggcctcagag    82560
cctgacctga gagtccgtac tcggcttcct gtggggtgta ggttctcgcg attcaggacg    82620
tccttccata tccctgccca gcctgtggtg cttgaaacgt tgccccatg ggaaacgtat     82680 gtgtgcagga gcctccctgc acggcccaag gggcttcgtt ttcagtcttc tgactgtcac    82740
ctcgtggggt tcagtagaga attcatgtga ctagcgcctg gccttgtgtg gcttggagga    82800
aatggtactg cccaaatagg aggaaaacac agcctccctg agcctgcatt ctgcacgctg    82860 cccagggct tcagaaaagg agtggccaca gcaccccgaa gggagcatct gtttacctgg     82920
cagtggctct cagagcagca gaacgggttc agttttagac tctgaagttg gttgtgattg    82980
acagaaccct ttgggagcaa actagtagag ttggattaaa ttctgggtga aaccctttc    83040 tcccacacaa aatagtttta gtgatttttt tcattgtcca ttacttgcca ggggcagttt    83100
tagcagcact tttgatagat tacgtctaat cctcccaacc aaccagcagg gtagctatta    83160
ctgtccacat tttacaggca aggaaacagg ctccaagagg ctgaggactt tgcccaggat    83220
gacatagcca atggacaagc agtgtctgtc agctgtgaag gcttcactct tattgtcctt    83280
ctaccttgaa tagaagtttt cctgataaga ataaacgagg aaaaggtcct tgcctcctgg    83340
aagaacaaat ctaccaggtg atctattcat tgtttcaact cagaatgcac ttgattcagg    83400
aggtcatctg accttcacct tggatggtta gtttcacttt ttacatatag tttttgcagg    83460 gtttatttt ataaaatcca agcgcgctgt tgattgtgtt ttccttgttt tcagccccc      83520 cactccagcc cgcagcacat ttccgctgtc cgtcagtaat tgtgtcctct ctttatgctt    83580
gcttggggaa tgttgttttc tgactaggct gatcattatc taaagaatct aattctgttg    83640
atttttaaaa cttttaggac cataaacgtt gtgttcatat atggacatgg aaatatttat    83700
ataattttat agaaaataac cttttagatg gtcaaagtgt aaggagtttt tttgtcagat    83760
aatcatttct acttcaaaaa catttcatgc aatattagaa taaagttcct gtcattcctc    83820
taaaaatctg cctgtgagtg agatgcgtgg tcagaggcca gtgccgtctt gtcttcacga    83880
gggcttctgt gaggcactgg cttggcttca tgtctttta gggggcagag gaggatagga    83940
ttttaacagt aggggaatg agggtgggca gagcccctt gatctgccat ccccagcact     84000
ggtgtgagtc cctttctcta atgcaggcct gcctcagcgg cgtgtgggga gaacgctgaa    84060
aggcagctcc tgtcaaagtc cctgccccgc tggatcggac acaggcttaa attaccgcat    84120
cgtttgcacc cctctgttct agggtgagtg tctgcaaaag gctgttctca aacacatctc    84180
aatcaggagg gatatgtttt gggttccttg gccttgaggg agtgagtcag gaggaggagc    84240
agaaaaatct tgactagtag gctctgctgg gaaagctctg tgggcatctt ggggtggccg    84300 ggggggtgtaa gtgagccaca cctgaaggga gttgacagtg taatcttcac ccacaccagg    84360
acacttcaaa gagtggaagg aggcactatg aatagttatg ccaggacaac tggcctaaac    84420
cgggactatc caggcaaact gggacatata ctccaccttcc ttcaaaggga aatagacatt   84480
gtgacatctc cattgacaca gactacgtac tttagaacct tgcctgatca taggttccag    84540
agacatgctg gtggcatagt ccgttatcat atttcaaggt tctcccccat atccacgtct    84600
tggtacctac acatctctgt agaatcattg aggtgattat ctcatggctc attgtgactg    84660
```

-continued

```
catagctaga tggccagccc cgccctccag catacccctgg aggacttcat gccatgcgtg    84720
cttgactgtt tttccggatg cctgggtaca gaaatttcat gttgtgtgca tgtcccattg    84780
tgaaaagtga gggtgatacc accttaggaa gggatcccat ttctttagaa gatagattct    84840 ttcttttttct ttttttttgtt atactttaag ttctaggtac atgtgcagag catgcaggtt   84900
tgttacgtag gtacacatgt gccattgtgg tttgctgcac ccgtcaacct atcatctaca    84960 ttaggtatttt ctcgtaatgc tttccctccc ctaatccccc accccctcagc aggcccccagt 85020 gtgtgatgtt ccctccctg cgtccatgtg ttctcattgt tcatctccca cttacgagtg    85080
agaatatgtg gtgtttggtt ttctgttctt gtgttagttt gctgagaatg atggtttcta   85140
gcttcatcca tgtccctgca aaggacatca actcatcctt tttttttttt ttttgagac    85200 gaactcatcc tttttttatgg ctacatagca ttccatggtg tacatgtgcc acattttcttt  85260 cagtctatca ttgatgggca tttgcgttgg ttccaagcct ttactattgt gaacagtgct    85320
gcaataaaca tagtgtccat gtgtctttat agtagaatga tttataatcc tttggatact    85380
ttctaaaact tgatcacatt ttcctgatat attcctcagg cagaataaat cacagcattc    85440
caaataactt ttagtctttt aagaccttag tgaagaattg tgatgggatt acctttttaa    85500
taaacaaatg cagtaattct cattttttt caaaatgac atctggaaat tgacatgtta    85560 gaaatagat tctcaaatta ttctgctaga ttaccaagga atcaagatta ataaatataaaa   85620 cctttttat taaagattaa aaataaaaac ttattttta taaatccagc atagaccaaa     85680
atcagccaat caaatagttt aattagaaag agattatttg aattgcaggg gttttttttt   85740
tttgctctaa aaattatga cagtgttta gtaggtaaat ttcctaatgt gtatacaatt    85800
gagttagaca atttttattt gcatac                                          85826
```

<210> SEQ ID NO 2
<211> LENGTH: 77
<212> TYPE: DNA
<213> ORGANISM: Homo sapiens

<400> SEQUENCE: 2

```
gaaattggct ttcatgcttc cctggcccag agaaacccca acgctcatca cttggaccac    60
aagatggaaa taaagca                                                    77
```

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 3

```
gtacttggtt aaaatatgca                                                 20
```

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

```
<400> SEQUENCE: 4
aggaaggtac ttggttaaaa                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 5
aaaaggagga aggtacttgg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 6
tggggaaaaa ggaggaaggt                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 7
aggggtgggg aaaaaggagg                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 8
aaagagaggg gtggggaaaa                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
```

```
<223> OTHER INFORMATION: 2'-methoxyethoxy

<400> SEQUENCE: 9
cattaaaaag agagggtgg                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 10
cttgtcatta aaagagagg                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 11
aatttccttg tcattaaaaa                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 12
aaagccaatt tccttgtcat                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 13
agcatgaaag ccaatttcct                                                   20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

```
<222> LOCATION: (1)..(20)
<223> OTHER INFORMATION: 2'-methoxyethoxy

<400> SEQUENCE: 14
agggaagcat gaaagccaat                                                     20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 15
tgggccaggg aagcatgaaa                                                     20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 16
tttctctggg ccagggaagc                                                     20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 17
tggggtttct ctgggccagg                                                     20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 18
gagcgttggg gtttctctgg                                                     20

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct
<220> FEATURE:
```

<221> NAME/KEY: misc_feature
<222> LOCATION: (1)..(20)
<223> OTHER INFORMATION: 2'-methoxyethoxy

<400> SEQUENCE: 19
agtgatgagc gttggggttt                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 20
ggtccaagtg atgagcgttg                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 21
cttgtggtcc aagtgatgag                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 22
ttccctcttg tggtccaagt                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 23
ctttatttcc ctcttgtggt                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct

```
<220> FEATURE:
<221> NAME/KEY: misc_feature
<222> LOCATION: (1)..(20)
<223> OTHER INFORMATION: 2'-methoxyethoxy

<400> SEQUENCE: 24
tactgcttta tttccctctt                                                     20

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 25
tctacctact gctttatttc                                                     20

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 26
ttgtgttcta cctactgctt                                                     20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 27
tatcttttgt gttctaccta                                                     20

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 28
gagtttatct tttgtgttct                                                     20

<210> SEQ ID NO 29
<211> LENGTH: 20
<212> TYPE: DNA
<213> ORGANISM: Artificial Sequence
<220> FEATURE:
```

```
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 29
gagctggagt ttatcttttg                                           20

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 30
agatgagagc tggagtttat                                           20

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 31
gacttagatg agagctggag                                           20

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 32
ggaagggact tagatgagag                                           20

<210> SEQ ID NO 33
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 33
ggtagaggaa gggacttaga                                           20

<210> SEQ ID NO 34
<211> LENGTH: 20
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 34
gcccaggtag aggaagggac                                                     20

<210> SEQ ID NO 35
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 35
agatgagagc tggagt                                                         16

<210> SEQ ID NO 36
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 36
gatgagagct ggagtt                                                         16

<210> SEQ ID NO 37
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 37
atgagagctg gagttt                                                         16

<210> SEQ ID NO 38
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 38
tgagagctgg agttta                                                         16

<210> SEQ ID NO 39
<211> LENGTH: 16
<212> TYPE: DNA
```

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 39
gagagctgga gtttat                                               16

<210> SEQ ID NO 40
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 40
agagctggag tttatc                                               16

<210> SEQ ID NO 41
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 41
gagctggagt ttatct                                               16

<210> SEQ ID NO 42
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 42
agctggagtt tatctt                                               16

<210> SEQ ID NO 43
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 43
gctggagttt atcttt                                               16

<210> SEQ ID NO 44
<211> LENGTH: 16
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 44
ctggagttta tctttt                                                   16

<210> SEQ ID NO 45
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 45
tggagtttat cttttg                                                   16

<210> SEQ ID NO 46
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 46
ggagtttatc ttttgt                                                   16

<210> SEQ ID NO 47
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 47
gagtttatct tttgtg                                                   16

<210> SEQ ID NO 48
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 48
agtttatctt ttgtgt                                                   16

<210> SEQ ID NO 49
```

```
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 49
gtttatcttt tgtgtt                                                     16

<210> SEQ ID NO 50
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 50
tttatctttt gtgttc                                                     16

<210> SEQ ID NO 51
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: 2'-methoxyethoxy

<400> SEQUENCE: 51
ttatcttttg tgttct                                                     16

<210> SEQ ID NO 52
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 52
agatgagagc tggagtt                                                    17

<210> SEQ ID NO 53
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 53
gatgagagct ggagttt                                                    17
```

```
<210> SEQ ID NO 54
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 54
atgagagctg gagttta                                                17

<210> SEQ ID NO 55
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 55
tgagagctgg agtttat                                                17

<210> SEQ ID NO 56
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 56
gagagctgga gtttatc                                                17

<210> SEQ ID NO 57
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 57
agagctggag tttatct                                                17

<210> SEQ ID NO 58
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 58
gagctggagt ttatctt                                                17
```

```
<210> SEQ ID NO 59
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 59
agctggagtt tatcttt                                                  17

<210> SEQ ID NO 60
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 60
gctggagttt atctttt                                                  17

<210> SEQ ID NO 61
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 61
ctggagttta tcttttg                                                  17

<210> SEQ ID NO 62
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 62
tggagtttat cttttgt                                                  17

<210> SEQ ID NO 63
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 63
ggagtttatc ttttgtg                                                  17
```

<210> SEQ ID NO 64
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 64
gagtttatct tttgtgt                                                  17

<210> SEQ ID NO 65
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 65
agtttatctt ttgtgtt                                                  17

<210> SEQ ID NO 66
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 66
gtttatcttt tgtgttc                                                  17

<210> SEQ ID NO 67
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: 2'-methoxyethoxy

<400> SEQUENCE: 67
tttatctttt gtgttct                                                  17

<210> SEQ ID NO 68
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 68
agatgagagc tggagttt                                                18

<210> SEQ ID NO 69
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 69
gatgagagct ggagttta                                                18

<210> SEQ ID NO 70
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 70
atgagagctg gagtttat                                                18

<210> SEQ ID NO 71
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 71
tgagagctgg agtttatc                                                18

<210> SEQ ID NO 72
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 72
gagagctgga gtttatct                                                18

<210> SEQ ID NO 73
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 73
agagctggag tttatctt                                                18

<210> SEQ ID NO 74
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 74
gagctggagt ttatcttt                                                18

<210> SEQ ID NO 75
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 75
agctggagtt tatctttt                                                18

<210> SEQ ID NO 76
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 76
gctggagttt atcttttg                                                18

<210> SEQ ID NO 77
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 77
ctggagttta tcttttgt                                                18

<210> SEQ ID NO 78
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

```
<400> SEQUENCE: 78
tggagtttat cttttgtg                                                    18

<210> SEQ ID NO 79
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 79
ggagtttatc ttttgtgt                                                    18

<210> SEQ ID NO 80
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 80
gagtttatct tttgtgtt                                                    18

<210> SEQ ID NO 81
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 81
agtttatctt ttgtgttc                                                    18

<210> SEQ ID NO 82
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 82
gtttatcttt tgtgttct                                                    18

<210> SEQ ID NO 83
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-methoxyethoxy
```

<400> SEQUENCE: 83
agatgagagc tggagttta                                              19

<210> SEQ ID NO 84
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-methoxyethoxy

<400> SEQUENCE: 84
gatgagagct ggagtttat                                              19

<210> SEQ ID NO 85
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-methoxyethoxy

<400> SEQUENCE: 85
atgagagctg gagtttatc                                              19

<210> SEQ ID NO 86
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-methoxyethoxy

<400> SEQUENCE: 86
tgagagctgg agtttatct                                              19

<210> SEQ ID NO 87
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-methoxyethoxy

<400> SEQUENCE: 87
gagagctgga gtttatctt                                              19

<210> SEQ ID NO 88
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)

```
<223> OTHER INFORMATION: 2'-methoxyethoxy

<400> SEQUENCE: 88
agagctggag tttatcttt                                                  19

<210> SEQ ID NO 89
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-methoxyethoxy

<400> SEQUENCE: 89
gagctggagt ttatctttt                                                  19

<210> SEQ ID NO 90
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-methoxyethoxy

<400> SEQUENCE: 90
agctggagtt tatcttttg                                                  19

<210> SEQ ID NO 91
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-methoxyethoxy

<400> SEQUENCE: 91
gctggagttt atcttttgt                                                  19

<210> SEQ ID NO 92
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-methoxyethoxy

<400> SEQUENCE: 92
ctggagttta tcttttgtg                                                  19

<210> SEQ ID NO 93
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

```
<222> LOCATION: (1)..(19)
<223> OTHER INFORMATION: 2'-methoxyethoxy

<400> SEQUENCE: 93
tggagtttat cttttgtgt                                                    19

<210> SEQ ID NO 94
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-methoxyethoxy

<400> SEQUENCE: 94
ggagtttatc ttttgtgtt                                                    19

<210> SEQ ID NO 95
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-methoxyethoxy

<400> SEQUENCE: 95
gagtttatct tttgtgttc                                                    19

<210> SEQ ID NO 96
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-methoxyethoxy

<400> SEQUENCE: 96
agtttatctt ttgtgttct                                                    19

<210> SEQ ID NO 97
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 97
gatgagagct ggagtttatc                                                   20

<210> SEQ ID NO 98
<211> LENGTH: 20
<212> TYPE: DNA
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (1)..(20)
<223> OTHER INFORMATION: 2'-methoxyethoxy

<400> SEQUENCE: 98
atgagagctg gagtttatct                                               20

<210> SEQ ID NO 99
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 99
tgagagctgg agtttatctt                                               20

<210> SEQ ID NO 100
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 100
gagagctgga gtttatcttt                                               20

<210> SEQ ID NO 101
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 101
agagctggag tttatctttt                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 102
agctggagtt tatcttttgt                                               20

<210> SEQ ID NO 103
<211> LENGTH: 20
<212> TYPE: DNA
<213> ORGANISM: Artificial Sequence
<220> FEATURE:
<223> OTHER INFORMATION: Synthetic Construct
```

```
<220> FEATURE:
<221> NAME/KEY: misc_feature
<222> LOCATION: (1)..(20)
<223> OTHER INFORMATION: 2'-methoxyethoxy

<400> SEQUENCE: 103
gctggagttt atcttttgtg                                               20

<210> SEQ ID NO 104
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 104
ctggagttta tcttttgtgt                                               20

<210> SEQ ID NO 105
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 105
gttgggccca ggtagaggaa                                               20

<210> SEQ ID NO 106
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 106
gcagagttgg gcccaggtag                                               20

<210> SEQ ID NO 107
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 107
agctggcaga gttgggccca                                               20

<210> SEQ ID NO 108
<211> LENGTH: 20
<212> TYPE: DNA
<213> ORGANISM: Artificial Sequence
<220> FEATURE:
```

<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 108
agaccagctg gcagagttgg                                        20

<210> SEQ ID NO 109
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 109
agacaagacc agctggcaga                                        20

<210> SEQ ID NO 110
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 110
tgggaagaca agaccagctg                                        20

<210> SEQ ID NO 111
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 111
caccatggga agacaagacc                                        20

<210> SEQ ID NO 112
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 112
gaaggcacca tgggaagaca                                        20

<210> SEQ ID NO 113
<211> LENGTH: 20
<212> TYPE: DNA
<213> ORGANISM: Artificial Sequence

```
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 113
aggaggaagg caccatggga                                               20

<210> SEQ ID NO 114
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 114
aatccaggag gaaggcacca                                               20

<210> SEQ ID NO 115
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 115
tggttaaaat atgcattggc                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 116
aaaatatgca ttggcagaaa                                               20

<210> SEQ ID NO 117
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 117
atgcattggc agaaagcact                                               20

<210> SEQ ID NO 118
<211> LENGTH: 20
<212> TYPE: DNA
```

<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 118
ttggcagaaa gcactttca                                              20

<210> SEQ ID NO 119
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 119
agaaagcact tttcagcttt                                             20

<210> SEQ ID NO 120
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 120 gcactttca gctttggaaa                                              20

<210> SEQ ID NO 121
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 121
tttcagcttt ggaaattaga                                             20

<210> SEQ ID NO 122
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 122
gctttggaaa ttagaaagtg                                             20

<210> SEQ ID NO 123
<211> LENGTH: 20

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 123
ggaaattaga aagtgaatct                                              20

<210> SEQ ID NO 124
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 124
ttagaaagtg aatctaaaag                                              20

<210> SEQ ID NO 125
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 125
ggtagaggaa gggactta                                                18

<210> SEQ ID NO 126
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 126
gtagaggaag ggacttag                                                18

<210> SEQ ID NO 127
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 127
tagaggaagg gacttaga                                                18

<210> SEQ ID NO 128
```

```
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 128
agaggaaggg acttagat                                                 18

<210> SEQ ID NO 129
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 129
gaggaaggga cttagatg                                                 18

<210> SEQ ID NO 130
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 130
aggaagggac ttagatga                                                 18

<210> SEQ ID NO 131
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 131
ggaagggact tagatgag                                                 18

<210> SEQ ID NO 132
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 132
gaagggactt agatgaga                                                 18
```

```
<210> SEQ ID NO 133
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 133
aagggactta gatgagag                                                 18

<210> SEQ ID NO 134
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 134
agggacttag atgagagc                                                 18

<210> SEQ ID NO 135
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 135
gggacttaga tgagagct                                                 18

<210> SEQ ID NO 136
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 136
ggacttagat gagagctg                                                 18

<210> SEQ ID NO 137
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 137
gacttagatg agagctgg                                                 18
```

<210> SEQ ID NO 138
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 138
acttagatga gagctgga                                                18

<210> SEQ ID NO 139
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 139
cttagatgag agctggag                                                18

<210> SEQ ID NO 140
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 140
ttagatgaga gctggagt                                                18

<210> SEQ ID NO 141
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: 2'-methoxyethoxy

<400> SEQUENCE: 141
tagatgagag ctggagtt                                                18

<210> SEQ ID NO 142
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 142
gtagaggaag ggacttagat                                              20

```
<210> SEQ ID NO 143
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 143
tagaggaagg gacttagatg                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 144
agaggaaggg acttagatga                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 145
gaggaaggga cttagatgag                                              20

<210> SEQ ID NO 146
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 146
aggaagggac ttagatgaga                                              20

<210> SEQ ID NO 147
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 147
```
gaagggactt agatgagagc                                                     20

<210> SEQ ID NO 148
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 148
aagggactta gatgagagct                                                     20

<210> SEQ ID NO 149
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 149
agggacttag atgagagctg                                                     20

<210> SEQ ID NO 150
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 150
gggacttaga tgagagctgg                                                     20

<210> SEQ ID NO 151
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 151
ggacttagat gagagctgga                                                     20

<210> SEQ ID NO 152
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 152
acttagatga gagctggagt                                              20

<210> SEQ ID NO 153
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 153
cttagatgag agctggagtt                                              20

<210> SEQ ID NO 154
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 154
ttagatgaga gctggagttt                                              20

<210> SEQ ID NO 155
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: 2'-methoxyethoxy

<400> SEQUENCE: 155
tagatgagag ctggagttta                                              20

<210> SEQ ID NO 156
<211> LENGTH: 20
<212> TYPE: DNA
<213> ORGANISM: Artificial Sequence
<220> FEATURE:
<223> OTHER INFORMATION: Synthetic Construct

<400> SEQUENCE: 156
ccagcaaagc ccttgttaag                                              20

<210> SEQ ID NO 157
<211> LENGTH: 19
<212> TYPE: DNA
<213> ORGANISM: Artificial Sequence
<220> FEATURE:
<223> OTHER INFORMATION: Synthetic Construct

<400> SEQUENCE: 157
gctcgttgct gggtatcag                                               19

<210> SEQ ID NO 158
<211> LENGTH: 19
<212> TYPE: DNA

```
<213> ORGANISM: Artificial Sequence
<220> FEATURE:
<223> OTHER INFORMATION: Synthetic Construct

<400> SEQUENCE: 158
gatcacaggg atgacctgc                                              19

<210> SEQ ID NO 159
<211> LENGTH: 18
<212> TYPE: DNA
<213> ORGANISM: Artificial Sequence
<220> FEATURE:
<223> OTHER INFORMATION: Synthetic Construct

<400> SEQUENCE: 159
gtttacgtcg ccgtccag                                               18

<210> SEQ ID NO 160
<211> LENGTH: 9
<212> TYPE: DNA
<213> ORGANISM: Artificial Sequence
<220> FEATURE:
<223> OTHER INFORMATION: Synthetic Construct

<400> SEQUENCE: 160 ttatctttt                                                          9

<210> SEQ ID NO 161
<211> LENGTH: 11
<212> TYPE: DNA
<213> ORGANISM: Artificial Sequence
<220> FEATURE:
<223> OTHER INFORMATION: Synthetic Construct

<400> SEQUENCE: 161
gacttagatg a                                                      11

<210> SEQ ID NO 162
<211> LENGTH: 15
<212> TYPE: DNA
<213> ORGANISM: Artificial Sequence
<220> FEATURE:
<223> OTHER INFORMATION: Synthetic Construct

<400> SEQUENCE: 162
tttcagcttt ggaaa                                                  15

<210> SEQ ID NO 163
<211> LENGTH: 58
<212> TYPE: DNA
<213> ORGANISM: Artificial Sequence
<220> FEATURE:
<223> OTHER INFORMATION: Synthetic Construct

<400> SEQUENCE: 163
ccaggtagag aagggactt agatgagagc tggagtttat cttttgtgtt ctacctac    58

<210> SEQ ID NO 164
<211> LENGTH: 98
<212> TYPE: DNA
<213> ORGANISM: Artificial Sequence
<220> FEATURE:
<223> OTHER INFORMATION: Synthetic Construct

<400> SEQUENCE: 164
cttgtcatta aaagagagg ggtggggaaa aaggaggaag gtacttggtt aaaatatgca  60
```
ttggcagaaa gcactttca gctttggaaa ttagaaag                    98

<210> SEQ ID NO 165
<211> LENGTH: 39
<212> TYPE: DNA
<213> ORGANISM: Artificial Sequence
<220> FEATURE:
<223> OTHER INFORMATION: Synthetic Construct

<400> SEQUENCE: 165
gatccaccgg tcgccaccat gacctgcgcg tcctgtgtc                  39

<210> SEQ ID NO 166
<211> LENGTH: 45
<212> TYPE: DNA
<213> ORGANISM: Artificial Sequence
<220> FEATURE:
<223> OTHER INFORMATION: Synthetic Construct

<400> SEQUENCE: 166
tcctcgccct tgctcaccat ggacagtcct ggaatgatgt tgtgg           45

<210> SEQ ID NO 167
<211> LENGTH: 36
<212> TYPE: DNA
<213> ORGANISM: Artificial Sequence
<220> FEATURE:
<223> OTHER INFORMATION: Synthetic Construct

<400> SEQUENCE: 167
ctgctttatt tccctcttgt ggtccaagtg atgagc                     36

<210> SEQ ID NO 168
<211> LENGTH: 36
<212> TYPE: DNA
<213> ORGANISM: Artificial Sequence
<220> FEATURE:
<223> OTHER INFORMATION: Synthetic Construct

<400> SEQUENCE: 168
gaccacaaga gggaaataaa gcagtaggta gaacac                     36

<210> SEQ ID NO 169
<211> LENGTH: 20
<212> TYPE: DNA
<213> ORGANISM: Artificial Sequence
<220> FEATURE:
<223> OTHER INFORMATION: Synthetic Construct

<400> SEQUENCE: 169
atggtgagca agggcgagga                                       20

<210> SEQ ID NO 170
<211> LENGTH: 20
<212> TYPE: DNA
<213> ORGANISM: Artificial Sequence
<220> FEATURE:
<223> OTHER INFORMATION: Synthetic Construct

<400> SEQUENCE: 170
catggtggcg accggtggat                                       20

OLIGONUCLEOTIDE THERAPY FOR WILSON DISEASE

FIELD OF THE INVENTION

The present invention relates to the field of oligonucleotides and their use for the treatment of disease. In particular, the invention pertains to antisense oligonucleotides that may be used in the treatment of Wilson disease.

BACKGROUND

Wilson disease is a fatal copper homeostasis disorder, typically diagnosed in patients between the ages of 5 and 35, leading to hepatic and neurologic symptoms due to free copper accumulation. The prevalence of Wilson disease is estimated to be 1 in 30,000 individuals. Impaired hepatobiliary excretion of copper may be caused by defects in the trans Golgi copper transporter ATP7B in liver hepatocytes. ATP7B is required for transport of copper from the cytoplasm to the endomembrane compartment, which is followed by the release of copper into the bile via vesicular transport from the Golgi and/or loading of copper onto apoceruloplasmin (CP) for bloodstream transport. Free copper accumulation causes direct oxidative damage to biomolecules (DNA, lipids, mitochondria) and oxidative damage/stress triggering apoptosis.

Present treatment guidelines for Wilson disease recommend an initial treatment with chelating agents, which sequester free copper and lead to its excretion, followed by maintenance treatment with chelating agents or zinc salts, which block intestinal absorption. Initial treatment with chelating agents (2-12 months) is traditionally required to remove excess copper from patients. Worsening liver condition can cause increased copper release from dead hepatocytes, as such, maintenance treatment may only be started when a stable liver condition is achieved. Maintenance treatment with zinc salts, however, is complicated by adherence difficulties and gastrointestinal side effects. Adverse effects due to chelation therapy further causes discontinuation in 20-30% patients. Chelation therapy is associated with immune reactions, reduced wound healing, neutropenia or thrombocytopenia, lymphadenopathy, proteinuria and nephrotoxicity, long-term liver iron accumulation, and spikes in free copper resulting in neurological damage.

An ATP7B mutation associated with Wilson disease is a single base pair change in exon 6 from adenosine to cytosine causing a corresponding change in amino acid 645 from methionine to arginine (M645R): chr13:52535985:A:C [hg19/b37]; NCBI Reference Sequence NG_008806.1 (SEQ ID NO: 1):g.546461>G; NM_0053.3 (ATP7B):c.19341>G (p.Met645Arg). The M645R mutation is presumed to result in partial to complete loss-of-function based on genetic evidence and compound heterozygotes with a truncating variant typically have Wilson disease onset between ages 4-15.

Recent analysis of the M645R mutated ATP7B protein, expressed using a cDNA-encoding plasmid, indicated that the mutant protein has similar capability to uptake copper in microsomal fractions of sf9 insect cells expressing only the mutant protein, whereas all other pathogenic mutations tested showed a decrease in capability. Further research found a similar result, with the M645R mutated ATP7B protein having no biochemical defect in numerous cellular assays.

Previous analysis of the M645R and associated mutations may have failed, however, to consider the effect of such a mutation on splicing. Splicing is a natural biological mechanism that occurs within human cells. Splicing may be used to process the primary messenger ribonucleic acid (mRNA) that is transcribed from deoxyribonucleic acid (DNA), before the mRNA is translated into protein. Splicing may involve removing one or more contiguous segments of mRNA (introns) to conjoin the remaining segments (exons), delimited by pairs of 5' splice sites and 3' splice sites. Alternative splicing, which may be the splicing together of different combinations of exons, may result in multiple mRNA transcripts from a single gene.

Certain human genetic diseases (e.g., caused by genetic aberrations, such as point mutations), may be caused by aberrant splicing. As such, there is a need for a splicing mediator to treat diseases that are caused by aberrant splicing.

SUMMARY OF THE INVENTION

In general, the invention provides an oligonucleotide including a nucleobase sequence complementary to a sequence within ATP7B exon6, a flanking intron, or a combination thereof.

In one aspect, the invention provides an antisense oligonucleotide including a nucleobase sequence at least 70% complementary to an ATP7B target sequence in exon 6, a 5'-flanking intron, a 3'-flanking intron, or a combination of exon 6 and the 5'-flanking or 3'-flanking intron.

In some embodiments, the ATP7B target sequence reduces the binding of a splicing factor to an intronic splicing silencer in the 5'-flanking or 3'-flanking intron.

In some embodiments, the ATP7B target sequence includes at least one nucleotide located among positions 54672-54680 in SEQ ID NO: 1. In some embodiments, the ATP7B target sequence includes at least one nucleotide located among positions 54691-54701 in SEQ ID NO: 1. In some embodiments, the ATP7B target sequence includes at least one nucleotide located among positions 54492-54506 in SEQ ID NO: 1.

In some embodiments, the ATP7B target sequence includes at least one nucleotide located among positions 54472-54516 in SEQ ID NO: 1. In some embodiments, the ATP7B target sequence includes at least one nucleotide located among positions 54522-54593 in SEQ ID NO: 1. In some embodiments, the ATP7B target sequence includes at least one nucleotide located among positions 54665-54718 in SEQ ID NO: 1.

In some embodiments, the nucleobase sequence is complementary to a sequence within the 5'-flanking intron. In some embodiments, the ATP7B target sequence is located within the 5'-flanking intron among positions up to 54517 in SEQ ID NO: 1. In some embodiments, the nucleobase sequence has at least 70% sequence identity to SEQ ID NO: 119, 120, 121, 122, 123, or 124. In some embodiments, the nucleobase sequence has at least 70% sequence identity to SEQ ID NO: 122. In some embodiments, the ATP7B target sequence is located within the 5'-flanking intron among positions 54522 to 54581 in SEQ ID NO: 1. In some embodiments, the nucleobase sequence has at least 70% sequence identity to SEQ ID NO: 3, 4, 5, 6, 7, 8, 9, or 10.

In some embodiments, the ATP7B target sequence is located within the combination of the 5'-flanking intron and exon 6. In some embodiments, the ATP7B target sequence is located within the combination of the 5'-flanking intron and exon 6 among positions 54562 to 54593 in SEQ ID NO: 1. In some embodiments, nucleobase sequence has at least 70% sequence identity to SEQ ID NO: 11.

In some embodiments, the ATP7B target sequence is located within exon 6 or the combination of the 3'-flanking intron and exon 6. In some embodiments, the ATP7B target sequence is located among positions 54631 to 54677 in SEQ ID NO: 1. In some embodiments, the nucleobase sequence has at least 70% sequence identity to SEQ ID NO: 22, 23, 24, or 25.

In some embodiments, the ATP7B target sequence is located within the 3'-flanking intron. In some embodiments, the ATP7B target sequence is located among positions 54655 to 54738 in SEQ ID NO: 1. In some embodiments, the 5'-terminal nucleotide of the oligonucleotide is complementary to neither position 54695 nor position 54696 of SEQ ID NO: 1. In some embodiments, the nucleobase sequence has at least 70% sequence identity to SEQ ID NO: 28, 29, 30, 31, 32, 33, 34, 35, 36, 37, 38, 39, 40, 41, 42, 43, 44, 45, 46, 47, 48, 49, 50, 51, 52, 54, 55, 56, 57, 58, 59, 60, 61, 62, 63, 64, 65, 66, 67, 70, 71, 72, 73, 74, 75, 76, 77, 78, 79, 80, 81, 82, 85, 86, 87, 88, 89, 90, 91, 92, 93, 94, 95, 96, 98, 99, 100, 101, 102, 103, 104, 105, 106, 107, 108, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, or 155. In some embodiments, the nucleobase sequence has at least 70% sequence identity to SEQ ID NOs: 39, 48, 49, 50, 61, 63, 64, 65, 66, 67, 76, 77, 78, 79, 80, 81, 90, 91, 92, 93, 94, 95, 100, 103, 104, 121, and 149.

In some embodiments, the sequence identity of any nucleobase sequence is at least 80%, 85%, 90%, or 95%, e.g., at least 90%. In some embodiments, the sequence identity is 100%.

In some embodiments, the antisense oligonucleotide includes at least one modified nucleobase.

In some embodiments, the antisense oligonucleotide includes at least one modified internucleoside linkage. In some embodiments, the modified internucleoside linkage is a phosphorothioate linkage. In some embodiments, the phosphorothioate linkage is a stereochemically enriched phosphorothioate linkage. In some embodiments, at least 50% of internucleoside linkages in the antisense oligonucleotide are independently the modified internucleoside linkage. In some embodiments, at least 70% of the internucleoside linkages in the antisense oligonucleotide are independently the modified internucleoside linkage. In some embodiments, all internucleoside linkages in the antisense oligonucleotide are independently the modified internucleoside linkage.

In some embodiments, the antisense oligonucleotide includes at least one modified sugar nucleoside. In some embodiments, at least one modified sugar nucleoside is a 2'-modified sugar nucleoside. In some embodiments, at least one 2'-modified sugar nucleoside includes a 2'-modification selected from the group consisting of 2'-fluoro, 2'-methoxy, and 2'-methoxyethoxy. In some embodiments, the 2'-modified sugar nucleoside includes the 2'-methoxyethoxy modification.

In some embodiments, all nucleosides in the antisense oligonucleotide are independently the modified sugar nucleosides.

In certain embodiments of the invention, all internucleoside linkages in the antisense oligonucleotide are phosphorothioate diester linkages, and all nucleosides in the antisense oligonucleotide are 2'-methoxyethoxy modified ribose nucleosides. Such antisense oligonucleotides may also further include a targeting moiety, such as N-acetylgalactosamine or a cluster thereof.

In some embodiments, at least one modified sugar nucleoside is a bridged nucleic acid. In some embodiments, the bridged nucleic acid is a locked nucleic acid (LNA), ethylene-bridged nucleic acid (ENA), or cEt nucleic acid.

In some embodiments, the antisense oligonucleotide is a morpholino oligomer.

In some embodiments, the antisense oligonucleotide further includes a targeting moiety. In some embodiments, the targeting moiety is covalently conjugated at the 5'-terminus of the antisense oligonucleotide. In some embodiments, the targeting moiety is covalently conjugated at the 3'-terminus of the antisense oligonucleotide. In some embodiments, the targeting moiety is covalently conjugated at an internucleoside linkage of the antisense oligonucleotide.

In some embodiments, the targeting moiety is covalently conjugated through a linker. In some embodiments, the linker is a cleavable linker (e.g., a linker including —S—S—, —C(O)O—, —C(O)S—, —OC(O)—, —SC(O)—).

Examples of targeting moieties include N-acetylgalactosamine, glycyrrhetinic acid, glycyrrhizin, lactobionic acid, lactoferrin, IgA, a bile acid (e.g., lithocholyltaurine or taurocholic acid), and clusters thereof. In some embodiments, the targeting moiety includes N-acetylgalactosamine. In some embodiments, the targeting moiety is an N-acetylgalactosamine cluster.

In some embodiments, the antisense oligonucleotide includes at least 12 nucleosides. In some embodiments, the antisense oligonucleotide includes at least 16 nucleosides. In some embodiments, the antisense oligonucleotide includes a total of 50 nucleosides or fewer. In some embodiments, the antisense oligonucleotide includes a total of 30 nucleosides or fewer. In some embodiments, the antisense oligonucleotide includes a total of 20 nucleosides or fewer. In some embodiments, the antisense oligonucleotide includes a total of 16 to 20 nucleosides. In some embodiments, the antisense oligonucleotide includes a total of 16 to 19 nucleosides.

In another aspect, the invention provides a pharmaceutical composition including the antisense oligonucleotide of the invention and a pharmaceutically acceptable excipient.

In yet another aspect, the invention provides a method of increasing the level of exon 6-containing ATP7B mRNA molecules in a cell expressing an aberrant ATP7B gene by contacting the cell with the antisense oligonucleotide of the invention. In some embodiments, the cell is in a subject.

In still another aspect, the invention provides a method of treating Wilson disease in a subject having an aberrant ATP7B gene by administering a therapeutically effective amount of the antisense oligonucleotide of the invention or the pharmaceutical composition of the invention to the subject in need thereof. In some embodiments, the administering step is performed parenterally. In some embodiments, the aberrant ATP7B gene is ATP7B having a g.54646T>G mutation in SEQ ID NO: 1.

Recognized herein is the need for compositions and methods for treating diseases that may be caused by abnormal splicing resulting from an underlying genetic aberration. In some cases, antisense nucleic acid molecules, such as oligonucleotides, may be used to effectively modulate the splicing of targeted genes in genetic diseases, in order to alter the gene products produced. This approach can be applied in therapeutics to selectively modulate the expression and gene product composition for genes involved in genetic diseases.

The present disclosure provides compositions and methods that may advantageously use antisense oligonucleotides targeted to and hybridizable with nucleic acid molecules that encode for ATP7B. Such antisense oligonucleotides may target one or more splicing regulatory elements in one or more exons or introns of ATP7B. These splicing regulatory elements modulate splicing of ATP7B ribonucleic acid (RNA).

In one aspect, the present disclosure provides an ATP7B RNA splice-modulating antisense oligonucleotide having a sequence targeted to one or more splicing regulatory elements adjacent to an exon of ATP7B. In some embodiments, a genetic aberration of ATP7B includes the M645R mutation. In some embodiments, the M645R mutation results from ATP7B chr13:52535985:A:C [hg19/b37] (g.54646>G in SEQ ID NO: 1). In some embodiments, the one or more splicing regulatory elements include an exonic splicing silencer element or an intronic splicing silencer element. In some embodiments, the sequence is targeted to an abnormally spliced exon. In some embodiments, the sequence is targeted to an intron adjacent to an abnormally spliced exon. In some embodiments, the antisense oligonucleotide modulates variant splicing to yield an increase in exon inclusion. In some embodiments, the antisense oligonucleotide has a length of 12 to 20 nucleotides. In some embodiments, the antisense oligonucleotide has a length of 12 to 30 nucleotides. In some embodiments, the antisense oligonucleotide has a length of 12 to 50 nucleotides.

In another aspect, the present disclosure provides a method for modulating splicing of ATP7B RNA in a cell, tissue, or organ of a subject, including bringing the cell, tissue, or organ in contact with an antisense oligonucleotide including one or more sequences targeted to one or more splicing regulatory elements of an abnormally spliced exon or an intron adjacent to the abnormally spliced exon. In some embodiments, the genetic aberration of ATP7B includes M645R. In some embodiments, the M645R results from ATP7B chr13:52535985:A:C [hg19/b37] (g.54646T>G in SEQ ID NO: 1). In some embodiments, the splicing regulatory element is an exonic splicing silencer element or an intronic splicing silencer element. In some embodiments, the sequence is targeted to an abnormally spliced exon. In some embodiments, the sequence is targeted to an intron adjacent to an abnormally spliced exon. In some embodiments, the antisense oligonucleotide modulates variant splicing to yield an increase in exon inclusion (e.g., exon 6 inclusion, e.g., increase by at least 5%, at least 10%, at least 15%, at least 20%, at least 25%, at least 30%, at least 35%, at least 40%, at least 45%, or at least 50%; e.g., up to 100%, up to 90%, up to 80%, up to 70%, up to 60%, up to 50%, as compared to the ratio of exon 6-including ATP7B transcripts to the total number of ATP7B transcript molecules in a cell including ATP7B gene having an exon 6-skipping mutation in the absence of a treatment with an antisense oligonucleotide). In some embodiments, the antisense oligonucleotide has a length of 12 to 20 nucleotides. In some embodiments, the antisense oligonucleotide has a length of 12 to 30 nucleotides. In some embodiments, the antisense oligonucleotide has a length of 12 to 50 nucleotides. In some embodiments, the subject has or is suspected of having a disease, e.g., Wilson disease, and the subject is monitored for a progression or regression of the disease in response to bringing the cell, tissue, or organ in contact with the composition.

In another aspect, the present disclosure provides a method for treating Wilson disease in a subject, including administering to the subject a therapeutically effective amount of an antisense oligonucleotide including a sequence targeted to a splicing regulatory element of an abnormally spliced exon or an intron adjacent to the abnormally spliced exon. The antisense oligonucleotide modulates splicing of ATP7B RNA. In some embodiments, the genetic aberration of ATP7B includes the M645R mutation. In some embodiments, the M645R mutation results from ATP7B chr13:52535985:A:C [hg19/b37] (g.54646T>G mutant of SEQ ID NO: 1). In some embodiments, the splicing regulatory element includes an exonic splicing silencer element or an intronic splicing silencer element. In some embodiments, the sequence is targeted to an abnormally spliced exon of ATP7B. In some embodiments, the sequence is targeted to an intron adjacent to an abnormally spliced exon of the genetic aberration of ATP7B that modulates variant splicing of ATP7B RNA. In some embodiments, the antisense oligonucleotide modulates splicing to yield an increase in exon inclusion (e.g., increase by at least 5%, at least 10%, at least 15%, at least 20%, at least 25%, at least 30%, at least 35%, at least 40%, at least 45%, or at least 50%; e.g., up to 100%, up to 90%, up to 80%, up to 70%, up to 60%, up to 50%, as compared to the ratio of exon 6-including ATP7B transcripts to the total number of ATP7B transcript molecules in a cell including ATP7B gene having an exon 6-skipping mutation in the absence of a treatment with an antisense oligonucleotide). In some embodiments, the antisense oligonucleotide has a length of 12 to 20 nucleotides. In some embodiments, the antisense oligonucleotide has a length of 12 to 30 nucleotides. In some embodiments, the antisense oligonucleotide has a length of 12 to 50 nucleotides. In some embodiments, the subject is monitored for a progression or regression of Wilson disease in response to administering to the subject the therapeutically effective amount of the antisense oligonucleotide. In some embodiments, the antisense oligonucleotide reduces 24-hour urinary copper level in the subject, e.g., by at least 5%, at least 10%, at least 15%, at least 20%, at least 25%, at least 30%, at least 35%, at least 40%, at least 45%, or at least 50%; e.g., up to 90%, up to 80%, up to 70%, up to 60%, up to 50%, as compared to a control subject. In some embodiments, the control subject is the subject prior to therapy with an antisense oligonucleotide of the invention or is a subject suffering from Wilson disease and not receiving an antisense oligonucleotide of the invention. In some embodiments, the antisense oligonucleotide reduces 24-hour urinary copper level in the subject to <100 µg/24 hours (<1.6 µmol/24 hours) (e.g., to 40 µg/24 hours (0.6 µmol/24 hours)).

In another aspect, the present disclosure provides a pharmaceutical composition for treatment of Wilson disease including an antisense oligonucleotide and a pharmaceutically acceptable carrier. The antisense oligonucleotide includes a sequence targeted to a splicing regulatory element of an abnormally spliced exon or an intron adjacent to the abnormally spliced exon. The antisense oligonucleotide modulates splicing of ATP7B RNA. In some embodiments, the genetic aberration of ATP7B includes M645R. In some embodiments, the M645R mutation results from ATP7B chr13:52535985:A:C [hg19/b37] (g.54646T>G mutant of SEQ ID NO: 1).

Definitions

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

The term "acyl," as used herein, represents a chemical substituent of formula —C(O)—R, where R is alkyl, aryl, arylalkyl, cycloalkyl, heterocyclyl, heterocyclyl alkyl, heteroaryl, or heteroaryl alkyl. An optionally substituted acyl is an acyl that is optionally substituted as described herein for each group R.

The term "acyloxy," as used herein, represents a chemical substituent of formula —OR, where R is acyl. An optionally substituted acyloxy is an acyloxy that is optionally substituted as described herein for acyl.

The term "alkane-tetrayl," as used herein, represents a tetravalent, acyclic, straight or branched chain, saturated hydrocarbon group having from 1 to 16 carbons, unless otherwise specified. Alkane-tetrayl may be optionally substituted as described for alkyl.

The term "alkane-triyl," as used herein, represents a trivalent, acyclic, straight or branched chain, saturated hydrocarbon group having from 1 to 16 carbons, unless otherwise specified. Alkane-triyl may be optionally substituted as described for alkyl.

The term "alkanoyl," as used herein, represents a chemical substituent of formula —C(O)—R, where R is alkyl. An optionally substituted alkanoyl is an alkanoyl that is optionally substituted as described herein for alkyl.

The term "alkoxy," as used herein, represents a chemical substituent of formula —OR, where R is a $C_{1-6}$ alkyl group, unless otherwise specified. An optionally substituted alkoxy is an alkoxy group that is optionally substituted as defined herein for alkyl.

The term "alkyl," as used herein, refers to an acyclic straight or branched chain saturated hydrocarbon group, which, when unsubstituted, has from 1 to 12 carbons, unless otherwise specified. In certain preferred embodiments, unsubstituted alkyl has from 1 to 6 carbons. Alkyl groups are exemplified by methyl; ethyl; n- and iso-propyl; n-, sec-, iso- and tert-butyl; neopentyl, and the like, and may be optionally substituted, valency permitting, with one, two, three, or, in the case of alkyl groups of two carbons or more, four or more substituents independently selected from the group consisting of: alkoxy; acyloxy; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thiol; silyl; cyano; =O; =S; and =NR', where R' is H, alkyl, aryl, or heterocyclyl. In some embodiments, a substituted alkyl includes two substituents (oxo and hydroxy, or oxo and alkoxy) to form a group -L-CO—R, where L is a bond or optionally substituted alkylene, and R is hydroxyl or alkoxy. Each of the substituents may itself be unsubstituted or, valency permitting, substituted with unsubstituted substituent(s) defined herein for each respective group.

The term "alkylene," as used herein, represents a divalent substituent that is a monovalent alkyl having one hydrogen atom replaced with a valency. An optionally substituted alkylene is an alkylene that is optionally substituted as described herein for alkyl.

The term "aryl," as used herein, represents a mono-, bicyclic, or multicyclic carbocyclic ring system having one or two aromatic rings. Aryl group may include from 6 to 10 carbon atoms. All atoms within an unsubstituted carbocyclic aryl group are carbon atoms. Non-limiting examples of carbocyclic aryl groups include phenyl, naphthyl, 1,2-dihydronaphthyl, 1,2,3,4-tetrahydronaphthyl, fluorenyl, indanyl, indenyl, etc. The aryl group may be unsubstituted or substituted with one, two, three, four, or five substituents independently selected from the group consisting of: alkyl; alkoxy; acyloxy; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thiol; silyl; and cyano. Each of the substituents may itself be unsubstituted or substituted with unsubstituted substituent(s) defined herein for each respective group.

The term "aryl alkyl," as used herein, represents an alkyl group substituted with an aryl group. The aryl and alkyl portions may be optionally substituted as the individual groups as described herein.

The term "arylene," as used herein, represents a divalent substituent that is an aryl having one hydrogen atom replaced with a valency. An optionally substituted arylene is an arylene that is optionally substituted as described herein for aryl.

The term "aryloxy," as used herein, represents a group —OR, where R is aryl. Aryloxy may be an optionally substituted aryloxy. An optionally substituted aryloxy is aryloxy that is optionally substituted as described herein for aryl.

The term "ATP7B," as used herein, represents a nucleic acid (e.g., genomic DNA, pre-mRNA, or mRNA) that is translated and, if genomic DNA, first transcribed, in vivo to ATPase copper transporting beta protein. An exemplary genomic DNA sequence comprising the human ATP7B gene is given by SEQ ID NO: 1 (NCBI Reference Sequence: NG_008806.1). SEQ ID NO: 1 provides the sequence for the antisense strand of the genomic DNA of ATP7B (positions 5001-83826 in SEQ ID NO: 1) and other nearby genes. One of skill in the art will recognize that an RNA sequence typically includes uridines instead of thymidines. The term "ATP7B," as used herein, represents wild-type and mutant versions. An exemplary mutant nucleic acid (e.g., genomic DNA, pre-mRNA, or mRNA) results in ATPase copper transporting beta protein lacking exon 6.

The term "bicyclic sugar moiety," as used herein, represents a modified sugar moiety including two fused rings. In certain embodiments, the bicyclic sugar moiety includes a furanosyl ring.

The expression "$C_{x-y}$," as used herein, indicates that the group, the name of which immediately follows the expression, when unsubstituted, contains a total of from x to y carbon atoms. If the group is a composite group (e.g., aryl alkyl), $C_{x-y}$ indicates that the portion, the name of which immediately follows the expression, when unsubstituted, contains a total of from x to y carbon atoms. For example, ($C_{6-10}$-aryl)-$C_{1-6}$-alkyl is a group, in which the aryl portion, when unsubstituted, contains a total of from 6 to 10 carbon atoms, and the alkyl portion, when unsubstituted, contains a total of from 1 to 6 carbon atoms.

The term "complementary," as used herein in reference to a nucleobase sequence, refers to the nucleobase sequence having a pattern of contiguous nucleobases that permits an oligonucleotide having the nucleobase sequence to hybridize to another oligonucleotide or nucleic acid to form a duplex structure under physiological conditions. Complementary sequences include Watson-Crick base pairs formed from natural and/or modified nucleobases. Complementary sequences can also include non-Watson-Crick base pairs, such as wobble base pairs (guanosine-uracil, hypoxanthine-uracil, hypoxanthine-adenine, and hypoxanthine-cytosine) and Hoogsteen base pairs.

The term "contiguous," as used herein in the context of an oligonucleotide, refers to nucleosides, nucleobases, sugar moieties, or internucleoside linkages that are immediately adjacent to each other. For example, "contiguous nucleobases" means nucleobases that are immediately adjacent to each other in a sequence.

The term "cycloalkyl," as used herein, refers to a cyclic alkyl group having from three to ten carbons (e.g., a $C_3$-$C_{10}$ cycloalkyl), unless otherwise specified. Cycloalkyl groups may be monocyclic or bicyclic. Bicyclic cycloalkyl groups may be of bicyclo[p.q.0]alkyl type, in which each of p and q is, independently, 1, 2, 3, 4, 5, 6, or 7, provided that the sum of p and q is 2, 3, 4, 5, 6, 7, or 8. Alternatively, bicyclic cycloalkyl groups may include bridged cycloalkyl structures, e.g., bicyclo[p.q.r]alkyl, in which r is 1, 2, or 3, each of p and q is, independently, 1, 2, 3, 4, 5, or 6, provided that the sum of p, q, and r is 3, 4, 5, 6, 7, or 8. The cycloalkyl group may be a spirocyclic group, e.g., spiro[p.q]alkyl, in which each of p and q is, independently, 2, 3, 4, 5, 6, or 7, provided that the sum of p and q is 4, 5, 6, 7, 8, or 9. Non-limiting examples of cycloalkyl include cyclopropyl, cyclobutyl, cyclopentyl, cyclohexyl, cycloheptyl, 1-bicyclo[2.2.1.]heptyl, 2-bicyclo[2.2.1.]heptyl, 5-bicyclo[2.2.1.]heptyl, 7-bicyclo[2.2.1.]heptyl, and decalinyl. The cycloalkyl group may be unsubstituted or substituted (e.g., optionally substituted cycloalkyl) with one, two, three, four, or five substituents independently selected from the group consisting of: alkyl; alkoxy; acyloxy; amino; aryl; aryloxy; azido; cycloalkyl; cycloalkoxy; halo; heterocyclyl; heteroaryl; heterocyclylalkyl; heteroarylalkyl; heterocyclyloxy; heteroaryloxy; hydroxy; nitro; thiol; silyl; cyano; =O; =S; =NR', where R' is H, alkyl, aryl, or heterocyclyl. Each of the substituents may itself be unsubstituted or substituted with unsubstituted substituent(s) defined herein for each respective group.

The term "cycloalkylene," as used herein, represents a divalent substituent that is a cycloalkyl having one hydrogen atom replaced with a valency. An optionally substituted cycloalkylene is a cycloalkylene that is optionally substituted as described herein for cycloalkyl.

The term "cycloalkoxy," as used herein, represents a group —OR, where R is cycloalkyl. Cycloalkoxy may be an optionally substituted cycloalkoxy. An optionally substituted cycloalkoxy is cycloalkoxy that is optionally substituted as described herein for cycloalkyl.

The term "duplex," as used herein, represents two oligonucleotides that are paired through hybridization of complementary nucleobases.

The term "exon 6," as used herein, refers to exon 6 of ATP7B pre-mRNA or genomic DNA, e.g., SEQ ID NO: 2, which corresponds to positions 54582 to 54658 in SEQ ID NO: 1 (hg19/b37 coordinates chr13:52535973-52536049), or a mutant version thereof (e.g., g.54646T>G in SEQ ID NO: 1).

The term "flanking intron," as used herein, refers to an intron that is adjacent to the 5'- or 3'-end of exon 6 or a mutant thereof. The flanking intron is a 5'-flanking intron or a 3'-flanking intron. The 5'-flanking intron corresponds to the flanking intron that is adjacent to the 5'-end of exon 6 (e.g., intron positions between exon 5 and exon 6 in SEQ ID NO: 1). The 3'-flanking intron corresponds to the flanking intron that is adjacent to the 3'-end of exon 6 (e.g., intron positions between exon 6 and exon 7 in SEQ ID NO: 1).

The term "genetic aberration," as used herein, generally refers to a mutation or variant in a gene. Examples of genetic aberration may include, but are not limited to, a point mutation (single nucleotide variant or single base substitution), an insertion or deletion (indel), a transversion, a translocation, an inversion, or a truncation. An aberrant ATP7B gene includes one or more mutations causing the splicing of pre-mRNA to skip exon 6.

The term "halo," as used herein, represents a halogen selected from bromine, chlorine, iodine, and fluorine.

The term "heteroalkane-tetrayl," as used herein refers to an alkane-tetrayl group interrupted once by one heteroatom; twice, each time, independently, by one heteroatom; three times, each time, independently, by one heteroatom; or four times, each time, independently, by one heteroatom. Each heteroatom is, independently, O, N, or S. In some embodiments, the heteroatom is O or N. An unsubstituted $C_{X-Y}$ heteroalkane-tetrayl contains from X to Y carbon atoms as well as the heteroatoms as defined herein. The heteroalkane-tetrayl group may be unsubstituted or substituted (e.g., optionally substituted heteroalkane-tetrayl), as described for heteroalkyl.

The term "heteroalkane-triyl," as used herein refers to an alkane-triyl group interrupted once by one heteroatom; twice, each time, independently, by one heteroatom; three times, each time, independently, by one heteroatom; or four times, each time, independently, by one heteroatom. Each heteroatom is, independently, O, N, or S. In some embodiments, the heteroatom is O or N. An unsubstituted $C_{X-Y}$ heteroalkane-triyl contains from X to Y carbon atoms as well as the heteroatoms as defined herein. The heteroalkane-triyl group may be unsubstituted or substituted (e.g., optionally substituted heteroalkane-triyl), as described for heteroalkyl.

The term "heteroalkyl," as used herein, refers to an alkyl group interrupted one or more times by one or two heteroatoms each time. Each heteroatom is independently O, N, or S. None of the heteroalkyl groups includes two contiguous oxygen atoms. The heteroalkyl group may be unsubstituted or substituted (e.g., optionally substituted heteroalkyl). When heteroalkyl is substituted and the substituent is bonded to the heteroatom, the substituent is selected according to the nature and valency of the heteroatom. Thus, the substituent bonded to the heteroatom, valency permitting, is selected from the group consisting of =O, —N($R^{N2}$)$_2$, —SO$_2$OR$^{N3}$, —SO$_2$R$^{N2}$, —SOR$^{N3}$, —COOR$^{N3}$, an N protecting group, alkyl, aryl, cycloalkyl, heterocyclyl, or cyano, where each $R^{N2}$ is independently H, alkyl, cycloalkyl, aryl, or heterocyclyl, and each $R^{N3}$ is independently alkyl, cycloalkyl, aryl, or heterocyclyl. Each of these substituents may itself be unsubstituted or substituted with unsubstituted substituent(s) defined herein for each respective group. When heteroalkyl is substituted and the substituent is bonded to carbon, the substituent is selected from those described for alkyl, provided that the substituent on the carbon atom bonded to the heteroatom is not Cl, Br, or I. In some embodiments, carbon atoms are found at the termini of a heteroalkyl group. In some embodiments, heteroalkyl is PEG.

The term "heteroalkylene," as used herein, represents a divalent substituent that is a heteroalkyl having one hydrogen atom replaced with a valency. An optionally substituted heteroalkylene is a heteroalkylene that is optionally substituted as described herein for heteroalkyl.

The term "heteroaryl," as used herein, represents a monocyclic 5-, 6-, 7-, or 8-membered ring system, or a fused or bridging bicyclic, tricyclic, or tetracyclic ring system; the ring system contains one, two, three, or four heteroatoms independently selected from the group consisting of nitrogen, oxygen, and sulfur; and at least one of the rings is an aromatic ring. Non-limiting examples of heteroaryl groups include benzimidazolyl, benzofuryl, benzothiazolyl, benzothienyl, benzoxazolyl, furyl, imidazolyl, indolyl, isoindazolyl, isoquinolinyl, isothiazolyl, isothiazolyl, isoxazolyl, oxadiazolyl, oxazolyl, purinyl, pyrrolyl, pyridinyl, pyrazinyl, pyrimidinyl, qunazolinyl, quinolinyl, thiadiazolyl (e.g., 1,3,4-thiadiazole), thiazolyl, thienyl, triazolyl, tetrazolyl, dihydroindolyl, tetrahydroquinolyl, tetrahydroisoquinolyl, etc. The term bicyclic, tricyclic, and tetracyclic heteroaryls include at least one ring having at least one heteroatom as described above and at least one aromatic ring. For example, a ring having at least one heteroatom may be fused to one, two, or three carbocyclic rings, e.g., an aryl ring, a cyclohexane ring, a cyclohexene ring, a cyclopentane ring, a cyclopentene ring, or another monocyclic heterocyclic ring. Examples of fused heteroaryls include 1,2,3,5,8,8a-hexahydroindolizine; 2,3-dihydrobenzofuran; 2,3-dihydroindole; and 2,3-dihydrobenzothiophene. Heteroaryl may be optionally substituted with one, two, three, four, or five substituents independently selected from the group consisting of: alkyl; alkoxy; acyloxy; aryloxy; amino; arylalkoxy; cycloalkyl; cycloalkoxy; halogen; heterocyclyl; heterocyclyl alkyl; heteroaryl; heteroaryl alkyl; heterocyclyloxy; heteroaryloxy; hydroxyl; nitro; thiol; cyano; =O; —NR$_2$, where each R is independently hydrogen, alkyl, acyl, aryl, arylalkyl, cycloalkyl, heterocyclyl, or heteroaryl; —COOR$^A$, where R$^A$ is hydrogen, alkyl, aryl, arylalkyl, cycloalkyl, heterocyclyl, or heteroaryl; and —CON(R$^B$)$_2$, where each R$^B$ is independently hydrogen, alkyl, aryl, arylalkyl, cycloalkyl, heterocyclyl, or heteroaryl. Each of the substituents may itself be unsubstituted or substituted with unsubstituted substituent(s) defined herein for each respective group.

The term "heteroarylene," as used herein, represents a divalent substituent that is a heteroaryl having one hydrogen atom replaced with a valency. An optionally substituted heteroarylene is a heteroarylene that is optionally substituted as described herein for heteroaryl.

The term "heteroaryloxy," as used herein, refers to a structure —OR, in which R is heteroaryl. Heteroaryloxy can be optionally substituted as defined for heteroaryl.

The term "heterocyclyl," as used herein, represents a monocyclic, bicyclic, tricyclic, or tetracyclic ring system having fused or bridging 4-, 5-, 6-, 7-, or 8-membered rings, unless otherwise specified, the ring system containing one, two, three, or four heteroatoms independently selected from the group consisting of nitrogen, oxygen, and sulfur. Heterocyclyl may be aromatic or non-aromatic. An aromatic heterocyclyl is heteroaryl as described herein. Non-aromatic 5-membered heterocyclyl has zero or one double bonds, non-aromatic 6- and 7-membered heterocyclyl groups have zero to two double bonds, and non-aromatic 8-membered heterocyclyl groups have zero to two double bonds and/or zero or one carbon-carbon triple bond. Heterocyclyl groups have a carbon count of 1 to 16 carbon atoms unless otherwise specified. Certain heterocyclyl groups may have a carbon count up to 9 carbon atoms. Non-aromatic heterocyclyl groups include pyrrolinyl, pyrrolidinyl, pyrazolinyl, pyrazolidinyl, imidazolinyl, imidazolidinyl, piperidinyl, homopiperidinyl, piperazinyl, pyridazinyl, oxazolidinyl, isoxazolidiniyl, morpholinyl, thiomorpholinyl, thiazolidinyl, isothiazolidinyl, thiazolidinyl, tetrahydrofuranyl, dihydrofuranyl, tetrahydrothienyl, dihydrothienyl, pyranyl, dihydropyranyl, dithiazolyl, etc. The term "heterocyclyl" also represents a heterocyclic compound having a bridged multicyclic structure in which one or more carbons and/or heteroatoms bridges two non-adjacent members of a monocyclic ring, e.g., quinuclidine, tropanes, or diaza-bicyclo [2.2.2]octane. The term "heterocyclyl" includes bicyclic, tricyclic, and tetracyclic groups in which any of the above heterocyclic rings is fused to one, two, or three carbocyclic rings, e.g., a cyclohexane ring, a cyclohexene ring, a cyclopentane ring, a cyclopentene ring, or another heterocyclic ring. Examples of fused heterocyclyls include 1,2,3,5,8,8a-hexahydroindolizine; 2,3-dihydrobenzofuran; 2,3-dihydroindole; and 2,3-dihydrobenzothiophene. The heterocyclyl group may be unsubstituted or substituted with one, two, three, four or five substituents independently selected from the group consisting of: alkyl; alkoxy; acyloxy; aryloxy; amino; arylalkoxy; cycloalkyl; cycloalkoxy; halogen; heterocyclyl; heterocyclyl alkyl; heteroaryl; heteroaryl alkyl; heterocyclyloxy; heteroaryloxy; hydroxyl; nitro; thiol; cyano; =O; =S; —NR$_2$, where each R is independently hydrogen, alkyl, acyl, aryl, arylalkyl, cycloalkyl, heterocyclyl, or heteroaryl; —COOR$^A$, where R$^A$ is hydrogen, alkyl, aryl, arylalkyl, cycloalkyl, heterocyclyl, or heteroaryl; and —CON(R$^B$)$_2$, where each R$^B$ is independently hydrogen, alkyl, aryl, arylalkyl, cycloalkyl, heterocyclyl, or heteroaryl.

The term "heterocyclyl alkyl," as used herein, represents an alkyl group substituted with a heterocyclyl group. The heterocyclyl and alkyl portions of an optionally substituted heterocyclyl alkyl are optionally substituted as described for heterocyclyl and alkyl, respectively.

The term "heterocyclylene," as used herein, represents a divalent substituent that is a heterocyclyl having one hydrogen atom replaced with a valency. An optionally substituted heterocyclylene is a heterocyclylene that is optionally substituted as described herein for heterocyclyl.

The term "heterocyclyloxy," as used herein, refers to a structure —OR, in which R is heterocyclyl. Heterocyclyloxy can be optionally substituted as described for heterocyclyl.

The term "heteroorganic," as used herein, refers to (i) an acyclic hydrocarbon interrupted one or more times by one or two heteroatoms each time, or (ii) a cyclic hydrocarbon including one or more (e.g., one, two, three, or four) endocyclic heteroatoms. Each heteroatom is independently O, N, or S. None of the heteroorganic groups includes two contiguous oxygen atoms. An optionally substituted heteroorganic group is a heteroorganic group that is optionally substituted as described herein for alkyl.

The term "hydrocarbon," as used herein, refers to an acyclic, branched or acyclic, linear compound or group, or a monocyclic, bicyclic, tricyclic, or tetracyclic compound or group. The hydrocarbon, when unsubstituted, consists of carbon and hydrogen atoms. Unless specified otherwise, an unsubstituted hydrocarbon includes a total of 1 to 60 carbon atoms (e.g., 1 to 16, 1 to 12, or 1 to 6 carbon atoms). An optionally substituted hydrocarbon is an optionally substituted acyclic hydrocarbon or an optionally substituted cyclic hydrocarbon. An optionally substituted acyclic hydrocarbon is optionally substituted as described herein for alkyl. An optionally substituted cyclic hydrocarbon is an optionally substituted aromatic hydrocarbon or an optionally substituted non-aromatic hydrocarbon. An optionally substituted aromatic hydrocarbon is optionally substituted as described herein for aryl. An optionally substituted non-aromatic cyclic hydrocarbon is optionally substituted as described herein for cycloalkyl. In some embodiments, an acyclic hydrocarbon is alkyl, alkylene, alkane-triyl, or alkane-tetrayl. In certain embodiments, a cyclic hydrocarbon is aryl or arylene. In particular embodiments, a cyclic hydrocarbon is cycloalkyl or cycloalkylene.

The terms "hydroxyl" and "hydroxy," as used interchangeably herein, represent —OH.

The term "hydrophobic moiety," as used herein, represents a monovalent group covalently linked to an oligonucleotide backbone, where the monovalent group is a bile acid (e.g., cholic acid, taurocholic acid, deoxycholic acid, oleyl lithocholic acid, or oleoyl cholenic acid), glycolipid, phospholipid, sphingolipid, isoprenoid, vitamin, saturated fatty acid, unsaturated fatty acid, fatty acid ester, triglyceride, pyrene, porphyrine, texaphyrine, adamantine, acridine, biotin, coumarin, fluorescein, rhodamine, Texas-Red, digoxygenin, dimethoxytrityl, t-butydimethylsilyl, t-butyldiphenylsilyl, cyanine dye (e.g., Cy3 or Cy5), Hoechst 33258 dye, psoralen, or ibuprofen. Non-limiting examples of the monovalent group include ergosterol, stigmasterol, β-sitosterol, campesterol, fucosterol, saringosterol, avenasterol, coprostanol, cholesterol, vitamin A, vitamin D, vitamin E, cardiolipin, and carotenoids. The linker connecting the monovalent group to the oligonucleotide may be an optionally substituted $C_{1-60}$ hydrocarbon (e.g., optionally substituted $C_{1-60}$ alkylene) or an optionally substituted $C_{2-60}$ heteroorganic (e.g., optionally substituted $C_{2-60}$ heteroalkylene), where the linker may be optionally interrupted with one, two, or three instances independently selected from the group consisting of an optionally substituted arylene, optionally substituted heterocyclylene, and optionally substituted cycloalkylene. The linker may be bonded to an oligonucleotide through, e.g., an oxygen atom attached to a 5'-terminal carbon atom, a 3'-terminal carbon atom, a 5'-terminal phosphate or phosphorothioate, a 3'-terminal phosphate or phosphorothioate, or an internucleoside linkage.

The term "internucleoside linkage," as used herein, represents a divalent group or covalent bond that forms a covalent linkage between adjacent nucleosides in an oligonucleotide. An internucleoside linkage is an unmodified internucleoside linkage or a modified internucleoside linkage. An "unmodified internucleoside linkage" is a phosphate (—O—P(O)(OH)—O—) internucleoside linkage ("phosphate phosphodiester"). A "modified internucleoside linkage" is an internucleoside linkage other than a phosphate phosphodiester. The two main classes of modified internucleoside linkages are defined by the presence or absence of a phosphorus atom. Non-limiting examples of phosphorus-containing internucleoside linkages include phosphodiester linkages, phosphotriester linkages, phosphorothioate diester linkages, phosphorothioate triester linkages, phosphorodithioate linkages, boranophosphonate linkages, morpholino internucleoside linkages, methylphosphonates, and phosphoramidate. Non-limiting examples of non-phosphorus internucleoside linkages include methylenemethylimino (—CH$_2$—N(CH$_3$)—O—CH$_2$—), thiodiester (—O—C(O)—S—), thionocarbamate (—O—C(O)(NH)—S—), siloxane (—O—Si(H)$_2$—O—), and N,N'-dimethylhydrazine (—CH$_2$—N(CH$_3$)—N(CH$_3$)—). Phosphorothioate linkages are phosphodiester linkages and phosphotriester linkages in which one of the non-bridging oxygen atoms is replaced with a sulfur atom. In some embodiments, an internucleoside linkage is a group of the following structure:

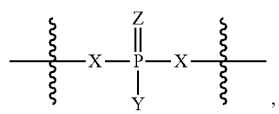

where
Z is O, S, B, or Se;
Y is —X-L-R$^1$;
each X is independently —O—, —S—, —N(-L-R$^1$)—, or L;

each L is independently a covalent bond or a linker (e.g., optionally substituted $C_{1-60}$ hydrocarbon linker or optionally substituted $C_{2-60}$ heteroorganic linker);
each R$^1$ is independently hydrogen, —S—S—R$^2$, —O—CO—R$^2$, —S—CO—R$^2$, optionally substituted $C_{1-9}$ heterocyclyl, a hydrophobic moiety, or a targeting moiety; and
each R$^2$ is independently optionally substituted $C_{1-10}$ alkyl, optionally substituted $C_{2-10}$ heteroalkyl, optionally substituted $C_{6-10}$ aryl, optionally substituted $C_{6-10}$ aryl $C_{1-6}$ alkyl, optionally substituted $C_{1-9}$ heterocyclyl, or optionally substituted $C_{1-9}$ heterocyclyl $C_{1-6}$ alkyl.

When L is a covalent bond, R$^1$ is hydrogen, Z is oxygen, and all X groups are —O—, the internucleoside group is known as a phosphate phosphodiester. When L is a covalent bond, R$^1$ is hydrogen, Z is sulfur, and all X groups are —O—, the internucleoside group is known as a phosphorothioate diester. When Z is oxygen, all X groups are —O—, and either (1) L is a linker or (2) R$^1$ is not a hydrogen, the internucleoside group is known as a phosphotriester. When Z is sulfur, all X groups are —O—, and either (1) L is a linker or (2) R$^1$ is not a hydrogen, the internucleoside group is known as a phosphorothioate triester. Non-limiting examples of phosphorothioate triester linkages and phosphotriester linkages are described in US 2017/0037399, the disclosure of which is incorporated herein by reference.

The term "morpholino," as used herein in reference to a class of oligonucleotides, represents an oligomer of at least 10 morpholino monomer units interconnected by morpholino internucleoside linkages. A morpholino includes a 5' group and a 3' group. For example, a morpholino may be of the following structure:

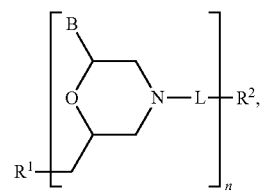

where
n is an integer of at least 10 (e.g., 12 to 50) indicating the number of morpholino units;
each B is independently a nucleobase;
R$^1$ is a 5' group;
R$^2$ is a 3' group; and
L is (i) a morpholino internucleoside linkage or, (ii) if L is attached to R$^2$, a covalent bond.

A 5' group in morpholino may be, e.g., hydroxyl, a hydrophobic moiety, phosphate, diphosphate, triphosphate, phosphorothioate, diphosphorothioate, triphosphorothioate, phosphorodithioate, disphorodithioate, triphosphorodithioate, phosphonate, phosphoramidate, a cell penetrating peptide, an endosomal escape moiety, or a neutral organic polymer. A 3' group in morpholino may be, e.g., hydrogen, a hydrophobic moiety, phosphate, diphosphate, triphosphate, phosphorothioate, diphosphorothioate, triphosphorothioate, phosphorodithioate, disphorodithioate, triphosphorodithioate, phosphonate, phosphoramidate, a cell penetrating peptide, an endosomal escape moiety, or a neutral organic polymer.

The term "morpholino internucleoside linkage," as used herein, represents a divalent group of the following structure:

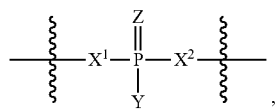

where
Z is O or S;
X$^1$ is a bond, —CH$_2$—, or —O—;
X$^2$ is a bond, —CH$_2$—O—, or —O—; and
Y is —NR$_2$, where each R is independently C$_{1-6}$ alkyl (e.g., methyl), or both R combine together with the nitrogen atom to which they are attached to form a C$_{2-9}$ heterocycly (e.g., N-piperazinyl);
provided that both X$^1$ and X$^2$ are not simultaneously a bond.

The term "nucleobase," as used herein, represents a nitrogen-containing heterocyclic ring found at the 1' position of the ribofuranose/2'-deoxyribofuranose of a nucleoside. Nucleobases are unmodified or modified. As used herein, "unmodified" or "natural" nucleobases include the purine bases adenine (A) and guanine (G), and the pyrimidine bases thymine (T), cytosine (C), and uracil (U). Modified nucleobases include 5-substituted pyrimidines, 6-azapyrimidines, alkyl or alkynyl substituted pyrimidines, alkyl substituted purines, and N-2, N-6 and O-6 substituted purines, as well as synthetic and natural nucleobases, e.g., 5-methylcytosine, 5-hydroxymethyl cytosine, xanthine, hypoxanthine, 2-aminoadenine, 6-alkyl (e.g., 6-methyl) adenine and guanine, 2-alkyl (e.g., 2-propyl) adenine and guanine, 2-thiouracil, 2-thiothymine, 2-thiocytosine, 5-halouracil, 5-halocytosine, 5-propynyl uracil, 5-propynyl cytosine, 5-trifluoromethyl uracil, 5-trifluoromethyl cytosine, 7-methyl guanine, 7-methyl adenine, 8-azaguanine, 8-azaadenine, 7-deazaguanine, 7-deazaadenine, 3-deazaguanine, 3-deazaadenine. Certain nucleobases are particularly useful for increasing the binding affinity of nucleic acids, e g., 5-substituted pyrimidines; 6-azapyrimidines; N2-, N6-, and/or O6-substituted purines. Nucleic acid duplex stability can be enhanced using, e.g., 5-methylcytosine. Non-limiting examples of nucleobases include: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example, 7-deazaadenine, 7-deazaguanine, 2-aminopyridine, or 2-pyridone. Further nucleobases include those disclosed in U.S. Pat. No. 3,687,808; The Concise Encyclopedia of Polymer Science and Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and in Chapters 6 and 15, Antisense Drug Technology, Crooke S. T., Ed., CRC Press, 2008, 163-166 and 442-443.

The term "nucleoside," as used herein, represents sugar-nucleobase compounds and groups known in the art (e.g., modified or unmodified ribofuranose-nucleobase and 2'-deoxyribofuranose-nucleobase compounds and groups known in the art). The sugar may be ribofuranose. The sugar may be modified or unmodified. An unmodified sugar nucleoside is ribofuranose or 2'-deoxyribofuranose having an anomeric carbon bonded to a nucleobase. An unmodified nucleoside is ribofuranose or 2'-deoxyribofuranose having an anomeric carbon bonded to an unmodified nucleobase. Non-limiting examples of unmodified nucleosides include adenosine, cytidine, guanosine, uridine, 2'-deoxyadenosine, 2'-deoxycytidine, 2'-deoxyguanosine, and thymidine. The modified compounds and groups include one or more modifications selected from the group consisting of nucleobase modifications and sugar modifications described herein. A nucleobase modification is a replacement of an unmodified nucleobase with a modified nucleobase. A sugar modification may be, e.g., a 2'-substitution, locking, carbocyclization, or unlocking. A 2'-substitution is a replacement of 2'-hydroxyl in ribofuranose with 2'-fluoro, 2'-methoxy, or 2'-(2-methoxy)ethoxy. A locking modification is an incorporation of a bridge between 4'-carbon atom and 2'-carbon atom of ribofuranose. Nucleosides having a locking modification are known in the art as bridged nucleic acids, e.g., locked nucleic acids (LNA), ethylene-bridged nucleic acids (ENA), and cEt nucleic acids. The bridged nucleic acids are typically used as affinity enhancing nucleosides.

The term "nucleotide," as used herein, represents a nucleoside bonded to an internucleoside linkage or a monovalent group of the following structure —X$^1$—P(X$^2$)(R$^1$)$_2$, where X$^1$ is O, S, or NH, and X$^2$ is absent, =O, or =S, and each R$^1$ is independently —OH, —N(R$^2$)$_2$, or —O—CH$_2$CH$_2$CN, where each R$^2$ is independently an optionally substituted alkyl, or both R$^2$ groups, together with the nitrogen atom to which they are attached, combine to form an optionally substituted heterocyclyl.

The term "oligonucleotide," as used herein, represents a structure containing 10 or more (e.g., 10 to 50) contiguous nucleosides covalently bound together by internucleoside linkages. An oligonucleotide includes a 5' end and a 3' end. The 5' end of an oligonucleotide may be, e.g., hydroxyl, a targeting moiety, a hydrophobic moiety, 5' cap, phosphate, diphosphate, triphosphate, phosphorothioate, diphosphorothioate, triphosphorothioate, phosphorodithioate, diphosphorodithioate, triphosphorodithioate, phosphonate, phosphoramidate, a cell penetrating peptide, an endosomal escape moiety, or a neutral organic polymer. The 3' end of an oligonucleotide may be, e.g., hydroxyl, a targeting moiety, a hydrophobic moiety, phosphate, diphosphate, triphosphate, phosphorothioate, diphosphorothioate, triphosphorothioate, phosphorodithioate, disphorodithioate, triphosphorodithioate, phosphonate, phosphoramidate, a cell penetrating peptide, an endosomal escape moiety, or a neutral organic polymer (e.g., polyethylene glycol). An oligonucleotide having a 5'-hydroxyl or 5'-phosphate has an unmodified 5' terminus. An oligonucleotide having a 5' terminus other than 5'-hydroxyl or 5'-phosphate has a modified 5' terminus. An oligonucleotide having a 3'-hydroxyl or 3'-phosphate has an unmodified 3' terminus. An oligonucleotide having a 3' terminus other than 3'-hydroxyl or 3'-phosphate has a modified 3' terminus.

The term "oxo," as used herein, represents a divalent oxygen atom (e.g., the structure of oxo may be shown as =O).

The term "pharmaceutically acceptable," as used herein, refers to those compounds, materials, compositions, and/or dosage forms, which are suitable for contact with the tissues of an individual (e.g., a human), without excessive toxicity, irritation, allergic response and other problem complications commensurate with a reasonable benefit/risk ratio.

The term "protecting group," as used herein, represents a group intended to protect a functional group (e.g., a hydroxyl, an amino, or a carbonyl) from participating in one or more undesirable reactions during chemical synthesis. The term "O-protecting group," as used herein, represents a group intended to protect an oxygen containing (e.g., phenol, hydroxyl or carbonyl) group from participating in one or more undesirable reactions during chemical synthesis. The term "N-protecting group," as used herein, represents a group intended to protect a nitrogen containing (e.g., an amino or hydrazine) group from participating in one or more undesirable reactions during chemical synthesis. Commonly used O- and N-protecting groups are disclosed in Wuts, "Greene's Protective Groups in Organic Synthesis," 4$^{th}$ Edition (John Wiley & Sons, New York, 2006), which is incorporated herein by reference. Exemplary O- and N-protecting groups include alkanoyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and arylalkyl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl) ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2, 2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydroxy carbonyl, t-butyloxycarbonyl, diisopropylmethoxycarbonyl, isopropoxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like.

The term "pyrid-2-yl hydrazone," as used herein, represents a group of the structure:

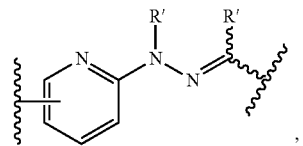

where each R' is independently H or optionally substituted 1-6 alkyl. Pyrid-2-yl hydrazone may be unsubstituted (i.e., each R' is H).

The term "splice site," as used herein, generally refers to a site in a genome corresponding to an end of an intron that may be involved in a splicing procedure. A splice site may be a 5' splice site (e.g., a 5' end of an intron) or a 3' splice site (e.g., a 3' end of an intron). A given 5' splice site may be associated with one or more candidate 3' splice sites, each of which may be coupled to its corresponding 5' splice site in a splicing operation.

The term "splicing enhancer," as used herein, refers to motifs with positive effects (e.g., causing an increase) on exon inclusion.

The term "splicing silencer," as used herein, refers to motifs with negative effects (e.g., causing a decrease) on exon inclusion.

The term "stereochemically enriched," as used herein, refers to a local stereochemical preference for one enantiomer of the recited group over the opposite enantiomer of the same group. Thus, an oligonucleotide containing a stereochemically enriched internucleoside linkage is an oligonucleotide, in which a stereogenic internucleoside linkage (e.g., phosphorothioate) of predetermined stereochemistry is present in preference to a stereogenic internucleoside linkage (e.g., phosphorothioate) of stereochemistry that is opposite of the predetermined stereochemistry. This preference can be expressed numerically using a diastereomeric ratio for the stereogenic internucleoside linkage (e.g., phosphorothioate) of the predetermined stereochemistry. The diastereomeric ratio for the stereogenic internucleoside linkage (e.g., phosphorothioate) of the predetermined stereochemistry is the molar ratio of the diastereomers having the identified stereogenic internucleoside linkage (e.g., phosphorothioate) with the predetermined stereochemistry relative to the diastereomers having the identified stereogenic internucleoside linkage (e.g., phosphorothioate) with the stereochemistry that is opposite of the predetermined stereochemistry. The diastereomeric ratio for the phosphorothioate of the predetermined stereochemistry may be greater than or equal to 1.1 (e.g., greater than or equal to 4, greater than or equal to 9, greater than or equal to 19, or greater than or equal to 39).

The term "subject," as used herein, represents a human or non-human animal (e.g., a mammal) that is suffering from, or is at risk of, disease, disorder, or condition, as determined by a qualified professional (e.g., a doctor or a nurse practitioner) with or without known in the art laboratory test(s) of sample(s) from the subject. A non-limiting example of a disease, disorder, or condition includes Wilson disease (e.g., Wilson disease associated with exon 6 skipping).

A "sugar" or "sugar moiety," includes naturally occurring sugars having a furanose ring or a structure that is capable of replacing the furanose ring of a nucleoside. Sugars included in the nucleosides of the invention may be non-furanose (or 4'-substituted furanose) rings or ring systems or open systems. Such structures include simple changes relative to the natural furanose ring (e.g., a six-membered ring). Alternative sugars may also include sugar surrogates wherein the furanose ring has been replaced with another ring system such as, e.g., a morpholino or hexitol ring system. Non-limiting examples of sugar moieties useful that may be included in the oligonucleotides of the invention include β-D-ribose, β-D-2'-deoxyribose, substituted sugars (e.g., 2',5', and bis substituted sugars), 4'-S-sugars (e.g., 4'-S-ribose, 4'-S-2'-deoxyribose, and 4'-S-2'-substituted ribose), bicyclic sugar moieties (e.g., the 2'-O—CH$_2$-4' or 2'-O—(CH$_2$)$_2$-4' bridged ribose derived bicyclic sugars) and sugar surrogates (when the ribose ring has been replaced with a morpholino or a hexitol ring system).

The term "targeting moiety," as used herein, represents a moiety (e.g., N-acetylgalactosamine or a cluster thereof) that specifically binds or reactively associates or complexes with a receptor or other receptive moiety associated with a given target cell population. An antisense oligonucleotide may contain a targeting moiety. An antisense oligonucleotide including a targeting moiety is also referred to herein as a conjugate. A targeting moiety may include one or more ligands (e.g., 1 to 6 ligands, 1 to 3 ligands, or 1 ligand). The ligand can be an antibody or an antigen-binding fragment or an engineered derivative thereof (e.g., Fcab or a fusion protein (e.g., scFv)). Alternatively, the ligand may be a small molecule (e.g., N-acetylgalactosamine).

The term "therapeutically effective amount," as used herein, represents the quantity of an antisense oligonucleotide of the invention necessary to ameliorate, treat, or at least partially arrest the symptoms of a disease or disorder (e.g., to increase the level of ATP7B mRNA molecules including exon 6). Amounts effective for this use may depend, e.g., on the severity of the disease and the weight and general state of the subject. Typically, dosages used in vitro may provide useful guidance in the amounts useful for in vivo administration of the pharmaceutical composition, and animal models may be used to determine effective dosages for treatment of particular disorders. In some embodiments, a therapeutically effective amount of an antisense oligonucleotide of the invention reduces 24-hour urinary copper level in the subject to <100 μg/24 hours (<1.6 μmol/24 hours) (e.g., to ≤40 μg/24 hours (≤0.6 μmol/24 hours)).

The term "thiocarbonyl," as used herein, represents a C(=S) group.—Non-limiting example of functional groups containing a "thiocarbonyl" includes thioesters, thioketones, thioaldehydes, thioanhydrides, thioacyl chlorides, thioamides, thiocarboxylic acids, and thiocarboxylates.

The term "thioheterocyclylene," as used herein, represents a divalent group —S—R'—, where R' is a heterocyclylene as defined herein.

The term "thiol," as used herein, represents an —SH group.

The term "triazolocycloalkenylene," as used herein, refers to the heterocyclylenes containing a 1,2,3-triazole ring fused to an 8-membered ring, all of the endocyclic atoms of which are carbon atoms, and bridgehead atoms are sp$^2$-hybridized carbon atoms. Triazocycloalkenylenes can be optionally substituted in a manner described for heterocyclyl.

The term "triazoloheterocyclylene," as used herein, refers to the heterocyclylenes containing a 1,2,3-triazole ring fused to an 8-membered ring containing at least one heteroatom. The bridgehead atoms in triazoloheterocyclylene are carbon atoms. Triazoloheterocyclylenes can be optionally substituted in a manner described for heterocyclyl.

Enumeration of positions within oligonucleotides and nucleic acids, as used herein and unless specified otherwise, starts with the 5'-terminal nucleoside as 1 and proceeds in the 3'-direction.

The compounds described herein, unless otherwise noted, encompass isotopically enriched compounds (e.g., deuterated compounds), tautomers, and all stereoisomers and conformers (e.g. enantiomers, diastereomers, E/Zisomers, atropisomers, etc.), as well as racemates thereof and mixtures of different proportions of enantiomers or diastereomers, or mixtures of any of the foregoing forms as well as salts (e.g., pharmaceutically acceptable salts).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

FIG. 1A shows RT-PCR analysis of HEK293T cells transfected with ATP7B minigenes. Exon inclusion (445 bp) and exclusion (368 bp) fragments are indicated by black solid arrowheads for both wildtype minigene (WT) and chr13:52535985:A:C [hg19/b37] (M645R) variant minigene. 100 bp DNA ladder is shown for size reference.

FIG. 2A is a schematic representation of the relative locations of the set of antisense oligonucleotides having the sequences set forth in SEQ ID NOs: 3-34, coarse-tilled across exon 6 and the flanking introns. FIG. 2 shows capillary electrophoresis of RT-PCR products of HEK293T cells transfected with ATP7B wildtype and M645R ATP7B minigenes and antisense oligonucleotides having the sequence set forth in SEQ ID NOs: 3-34. A 100 bp DNA ladder is shown for size reference with the exon 6 inclusion band at 445 bp and exclusion band at 368 bp. FIG. 2C depicts the percentage of exon 6 inclusion in ATP7B wildtype and M645R ATP7B minigenes co-transfected with antisense oligonucleotides having the sequence set forth in SEQ ID NOs: 3-34 calculated by quantification of the RT-PCR fragments observed in FIG. 2B. Inclusion percentages were normalized according to fragment sizes (n=4 for WT, n=5 for M645R).

FIG. 3 is a depiction of the forward strand of the human genome surrounding exon 6 of the ATP7B gene, which is in reverse complement (i.e., antisense) with respect to the ATP7B transcript. (SEQ ID NO: 163 CCAGGTAGAG-GAAGGGACTTAGATGAGAGCTGGAGTT-TATCTTTTGTGTTCTACCTAC and SEQ ID: 164 CTTGT-CATTAAAAAGAGAGGGGTGGGGAAAAAGGAGGAA GGTACTTGGTTAAAATATGCATTGGCAG AAAGCACTTTTCAGCTTTGGAAATTAGAAAG) (underlined). The location and sequence of antisense oligonucleotides according to the invention are also shown SEQ ID NOs: 28-33, 47-51, 60, 61, 63-67, 76-81, 93-95, 120, 121, 130, 132-137, 147, and 150 and their corresponding effect on the percent of exon 6 spliced in (dPSI).

FIG. 4A depicts the results of a copper sensitivity assay using both HepG2 wild-type (Wt) and 2F3 cells as well as corresponding non-transfected (NT) controls. 2F3 cells are compound heterozygous, with one allele including the M645R mutation and the other allele inactivated by the insertion of a plasmid sequence. The M645R variant (2F3) has lower cell viability with increasing copper concentration as compared to wildtype cells. This phenotype is partially rescued by transfection with an oligonucleotide (SEQ ID NO: 29), which increases the inclusion of exon 6 (error bars representing the standard deviation for the experiment done in triplicate). FIG. 4B depicts a western blot against ATP7B using both HepG2 wild-type (Wt) and 2F3 cells as well as corresponding non-transfected (NT) controls. The mutant (2F3) shows a decrease in ATP7B protein levels. This phenotype is partially rescued by transfection with an oligonucleotide (SEQ ID NO: 29), which increases the inclusion of exon 6.

DETAILED DESCRIPTION

Figure 1A:
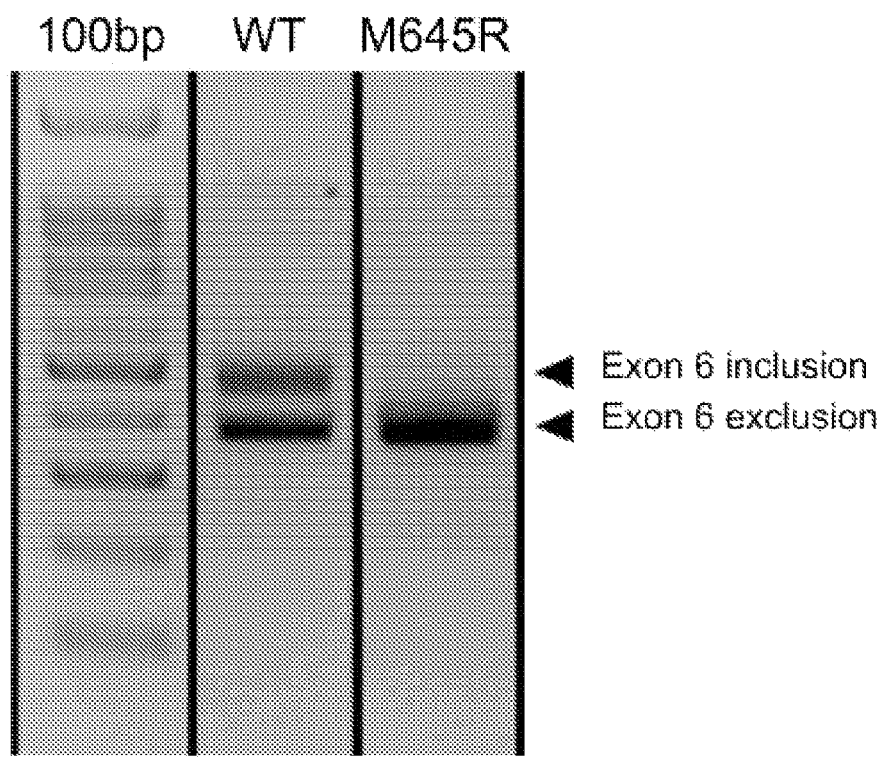
FIGS. 1A and B show the chr13:52535985:A:C [hg19/b37] variant reduces exon 6 inclusion in ATP7B minigenes.

In general, the present invention provides antisense oligonucleotides, compositions, and methods that target ATP7B exon 6 or a flanking intron. Surprisingly, the inventors have found that altering ATP7B gene splicing to include exon 6 in the transcript may be used to treat Wilson disease and antisense oligonucleotides may be used to alter splicing of the ATP7B gene to include exon 6. The antisense oligonucleotides of the invention may modulate splicing of ATP7B pre-mRNA to increase the level of ATP7B mRNA molecules having exon 6. Accordingly, the antisense oligonucleotides may be used to treat Wilson disease in a subject in need of a treatment therefor. Typically, an antisense oligonucleotide includes a nucleobase sequence at least 70% complementary to an ATP7B target sequence in exon 6, a 5'-flanking intron, a 3'-flanking intron, or a combination of exon 6 and the 5'-flanking or 3'-flanking intron.

Genetic variants may correspond to changes or modifications in transcription and/or splicing. RNA is initially transcribed from DNA as pre-mRNA, with protein-coding and 5'UTR/3'UTR exons separated by introns. Splicing generally refers to the molecular process, carried out by the spliceosome complexes that may remove introns and adjoins exons, producing a mature mRNA sequence, which is then scanned and translated to protein by the ribosome. The molecular reaction catalyzed by the spliceosome may comprise (i) nucleophilic attack of the branch site adenosine 2'OH onto the outmost base of the intronic donor dinucleotide, with consequent release of the outmost exonic donor base 3'OH; and (ii) nucleophilic attack of the exonic donor 3'OH onto the outmost exonic acceptor base, with consequent release of the intron lariat and the spliced exons.

Splicing sequence changes can include the following categories: (a) alteration of a splice site (denominated canonical splice site) or exon recognition sequence required for the proper composition of a gene product, and (b) activation and utilization of an incorrect splice site (denominated cryptic splice site), or incorrect recognition of intronic sequence as an exon (denominated pseudo exon); both may result in the improper composition of a gene product. The splice site recognition signal may be required for spliceosome assembly and can comprise the following structures: (i) highly conserved intronic dinucleotide (AG, GT), immediately adjacent to the exon-intron boundary, and (ii) consensus sequence surrounding the intronic dinucleotide (often delimited to 3 exonic and 6 intronic nucleotides for the donor site, 3 exonic and 20 intronic nucleotides for the acceptor site) and branch site (variable position on the intronic acceptor side); both with lower conservation and more sequence variety.

In addition to splice site recognition, the exon recognition signal may comprise a plethora of motifs recognized by splicing factors and other RNA binding proteins, some of which may be ubiquitously expressed and some of which may be tissue specific. These motifs may be distributed over the exon body and in the proximal intronic sequence. The term "splicing enhancer" refers to motifs with positive effects (e.g., causing an increase) on exon inclusion, and the term "splicing silencer" refers to motifs with negative effects (e.g., causing a decrease) on exon inclusion. The exon recognition signal may be particularly important for correct splicing in the presence of weak consensus sequence. When a variant weakens the splice site recognition, the exon can be skipped and/or a nearby cryptic splice site which is already fairly strong can be used; especially in the presence of short introns, full intron retention is also a possible outcome. In particular, alteration of the intronic dinucleotide often results in splicing alteration, whereas consensus sequence alteration may be, on average, less impactful and more context-dependent. When the exon recognition signal is weakened, exon skipping may be a more likely outcome, but cryptic splice site use is also possible, especially in the presence of very weak consensus sequence. Variants can also strengthen a weak cryptic splice site in proximity of the canonical splice site, and significantly increase its usage resulting in improper splicing and incorrect gene product (with effects including amino acid insertion/deletion, frameshift, and stop-gain). Finally, variants that are more distant from canonical splice site can induce recognition of an exonic sequence as an intron, again resulting in improper gene product composition; specifically, these variants can increase the strength of the splice sites or the exon recognition signal.

Antisense oligonucleotides can be used to modulate gene splicing (e.g., by targeting splicing regulatory elements of the gene).

Antisense oligonucleotides may comprise splice-switching oligonucleotides (SSOs), which may modulate splicing by steric blockage (e.g., to enhance the inclusion of exon 6), preventing the spliceosome assembly or the binding of splicing factors and RNA binding proteins. Blocking the spliceosome assembly proteins may be therapeutically used to cause exon skipping. Blocking binding of specific splicing factors or RNA binding proteins that have an inhibitory effect may be used to produce increased exon inclusion. Specific steric blocker antisense oligonucleotide chemistries may include the modified RNA chemistry with phosphorothioate backbone (PS) with a sugar modification (e.g., 2'-modification) and phosphorodiamidate morpholino (PMO). Exemplary PS backbone sugar modifications may include 2'-O-methyl (2'OMe) and 2'-O-methoxyethyl (2'-MOE), which is also known as 2'-methoxyethoxy. Other nucleotide modifications may be used, for example, for the full length of the oligonucleotide or for specific bases. The oligonucleotides can be covalently conjugated to a targeting moiety (e.g., a GalNAc cluster), or to a peptide (e.g., a cell penetrating peptide), or to another molecular or multimolecular group (e.g., a hydrophobic moiety or neutral polymer) different from the rest of the oligonucleotide. Antisense oligonucleotides may be used as a single stereoisomer or a combination of stereoisomers.

The ATP7B gene (ATPase copper transporting beta, OMIM: 606882) may play an important role in pathogenicity of Wilson disease (also known as Wilson's disease). ATP7B is a gene encoding an intracellular trans-Golgi copper transporter. The gene may be expressed in liver hepatocytes and may be required for copper excretion from the bloodstream to the bile and for ceruloplasmin copper loading. Defective copper excretion and/or ceruloplasmin copper loading can lead to toxic effects in the liver and central nervous system. ATP7B homozygous or compound heterozygous loss-of-function may result in the autosomal recessive Wilson Disease (OMIM: 277900).

Recognizing a need for effective splicing modulation therapies for diseases such as Wilson disease, the present disclosure provides ATP7B splice-modulating antisense oligonucleotides comprising sequences targeted to a splicing regulatory element of an abnormally spliced exon or an intron adjacent to an abnormally spliced exon of ATP7B. The present disclosure also provides methods for modulating splicing of ATP7B RNA in a cell, tissue, or organ of a subject by bringing the cell, tissue, or organ in contact with an antisense oligonucleotide of the invention. An ATP7B splice-modulating antisense oligonucleotide may comprise a nucleobase sequence targeted to a splicing regulatory element of an abnormally spliced exon or an intron adjacent to an abnormally spliced exon of ATP7B. In addition, the present disclosure provides a method for treating Wilson disease in a subject by administering to the subject a therapeutically effective amount of an oligonucleotide of the invention. An ATP7B splice-modulating antisense oligonucleotide may comprise a sequence targeted to a splicing regulatory element of an abnormally spliced exon or an intron adjacent to an abnormally spliced exon of ATP7B.

Splicing regulatory elements may include, for example, exonic splicing silencer elements or intronic splicing silencer elements. The antisense oligonucleotides may comprise sequences targeted to an exon or an intron adjacent to the exon of ATP7B which modulates variant splicing of ATP7B RNA. The modulation of splicing may result in an increase in exon inclusion. Antisense oligonucleotides may comprise a total of 8 to 50 nucleotides (e.g., 8 to 16 nucleotides, 8 to 20 nucleotides, 12 to 20 nucleotides, 12 to 30 nucleotides, or 12 to 50 nucleotides).

Genetic aberrations of the ATP7B gene may play an important role in pathogenicity. In particular, an ATP7B M645R genetic aberration, ATP7B chr13:52535985:A:C [hg19/b37] (hg19 coordinates) (g.54646T>G mutant of SEQ ID NO: 1), may result in NM_000053.3 cDNA change 1934T>G and protein sequence Met645Arg (M645R) in exon 6. Genome coordinates may be expressed, for example, with respect to human genome reference hg19/b37. For example, this variant has been reported as pathogenic in patients with Wilson Disease.

Other exemplary genetic aberrations which are predicted in silico to cause a decrease in exon 6 inclusion and which have been observed in the Human Gene Mutation Database (HGMD) include chr13:52535964:T:C (position 54667 in SEQ ID NO: 1; HMGD ID: CS076596) and chr13: 52535994:T:C (position 54637 in SEQ ID NO: 1; HMGD ID: CM164020).

These exemplary genetic aberrations may be targeted with antisense oligonucleotides to increase levels of exon inclusion, and other similar mutations in splicing regulatory elements may be targeted in a similar fashion.

Different antisense oligonucleotides can be combined for increasing the inclusion of exon 6 of ATP7B. A combination of two antisense oligonucleotides may be used in a method of the invention, such as two antisense oligonucleotides, three antisense oligonucleotides, four different antisense oligonucleotides, or five different antisense oligonucleotides targeting the same or different regions or hotspots.

An antisense oligonucleotide according to the invention may be indirectly administered using suitable techniques and methods known in the art. It may for example be provided to an individual or a cell, tissue or organ of the individual in the form of an expression vector wherein the expression vector encodes a transcript comprising said oligonucleotide. The expression vector is preferably introduced into a cell, tissue, organ or individual via a gene delivery vehicle. In an embodiment, there is provided a viral based expression vector comprising an expression cassette or a transcription cassette that drives expression or transcription of an antisense oligonucleotide as identified herein. Accordingly, the present invention provides a viral vector expressing an antisense oligonucleotide according to the invention.

An antisense oligonucleotide according to the invention may be directly administered using suitable techniques and methods known in the art, e.g., using conjugates described herein.

Conjugates

Oligonucleotides of the invention may include an auxiliary moiety, e.g., a targeting moiety, hydrophobic moiety, cell penetrating peptide, or a polymer. An auxiliary moiety may be present as a 5' terminal modification (e.g., covalently bonded to a 5'-terminal nucleoside), a 3' terminal modification (e.g., covalently bonded to a 3'-terminal nucleoside), or an internucleoside linkage (e.g., covalently bonded to phosphate or phosphorothioate in an internucleoside linkage).

Targeting Moieties

An oligonucleotide of the invention may include a targeting moiety.

A targeting moiety is selected based on its ability to target oligonucleotides of the invention to a desired or selected cell population that expresses the corresponding binding partner (e.g., either the corresponding receptor or ligand) for the selected targeting moiety. For example, an oligonucleotide of the invention could be targeted to hepatocytes expressing asialoglycoprotein receptor (ASGP-R) by selecting a targeting moiety containing N-acetylgalactosamine (GalNAc).

A targeting moiety may include one or more ligands (e.g., 1 to 9 ligands, 1 to 6 ligands, 1 to 3 ligands, 3 ligands, or 1 ligand). The ligand may target a cell expressing asialoglycoprotein receptor (ASGP-R), IgA receptor, HDL receptor, LDL receptor, or transferrin receptor. Non-limiting examples of the ligands include N-acetylgalactosamine, glycyrrhetinic acid, glycyrrhizin, lactobionic acid, lactoferrin, IgA, or a bile acid (e.g., lithocholyltaurine or taurocholic acid).

The ligand may be a small molecule, e.g., a small molecules targeting a cell expressing asialoglycoprotein receptor (ASGP-R). A non-limiting example of a small molecule targeting an asialoglycoprotein receptor is N-acetylgalactosamine. Alternatively, the ligand can be an antibody or an antigen-binding fragment or an engineered derivative thereof (e.g., Fcab or a fusion protein (e.g., scFv)).

A targeting moiety may be -LinkA(-T)$_p$, where LinkA is a multivalent linker, each T is a ligand (e.g., asialoglycoprotein receptor-targeting ligand (e.g., N-acetylgalactosamine)), and p is an integer from 1 to 9. When each T is N-acetylgalactosamine, the targeting moiety is referred to as a galactosamine cluster. Galactosamine clusters that may be used in oligonucleotides of the invention are known in the art. Non-limiting examples of the galactosamine clusters that may be included in the oligonucleotides of the invention are provided in U.S. Pat. Nos. 5,994,517; 7,491,805; 9,714,421; 9,867,882; 9,127,276; US 2018/0326070; US 2016/0257961; WO 2017/100461; and in Sliedregt et al., J. Med. Chem., 42:609-618, 1999. Ligands other than GalNAc may also be used in clusters, as described herein for galactosamine clusters.

Targeting moiety-LinkA(-T)$_p$ may be a group of formula (I):

$$-Q^1-Q^2([-Q^3-Q^4-Q^5]_s-Q^6-T)_p, \quad (I)$$

where each s is independently an integer from 0 to 20 (e.g., from 0 to 10), where the repeating units are the same or different;

$Q^1$ is a conjugation linker (e.g., $[-Q^3-Q^4-Q^5]_s-Q^c$-, where $Q^c$ is optionally substituted $C_{2-12}$ heteroalkylene (e.g., a heteroalkylene containing —C(O)—N(H)—, —N(H)—C(O)—, —S(O)$_2$—N(H)—, —N(H)—S(O)$_2$—, or —S—S—), optionally substituted $C_{1-12}$ thioheterocyclylene (e.g.,

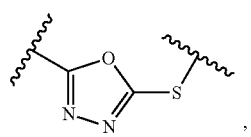

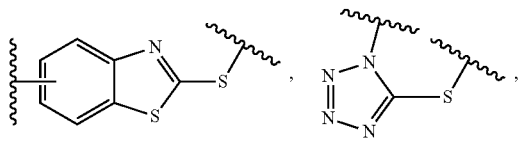

-continued

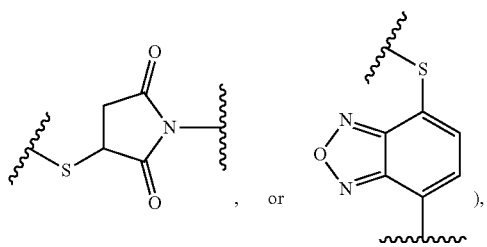

optionally substituted $C_{1-12}$ heterocyclylene (e.g., 1,2,3-triazole-1,4-diyl

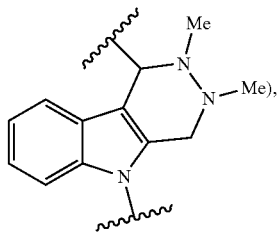

cyclobut-3-ene-1,2-dione-3,4-diyl, pyrid-2-yl hydrazone, optionally substituted $C_{6-16}$ triazoloheterocyclylene (e.g.,

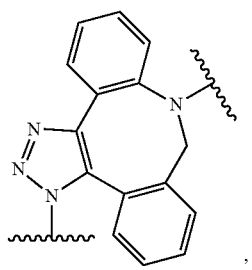

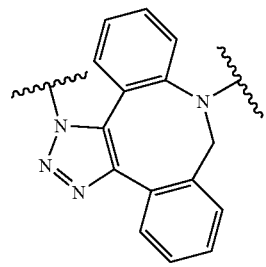

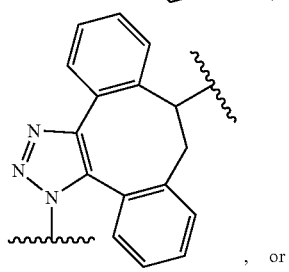

, or optionally substituted $C_{8-16}$ triazolocycloalkenylene (e.g.,

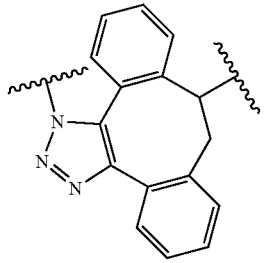

),

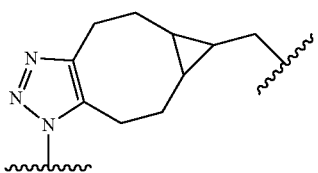

), or a dihydropyridazine group (e.g.,

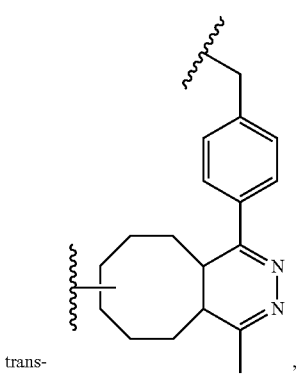

trans-  ,

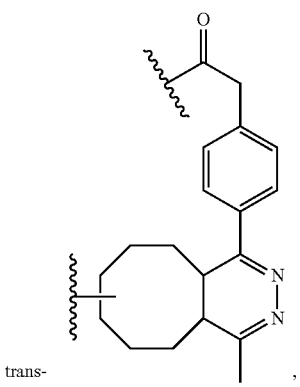

trans-  ,

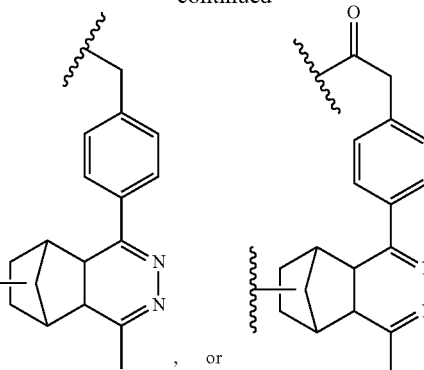

, or

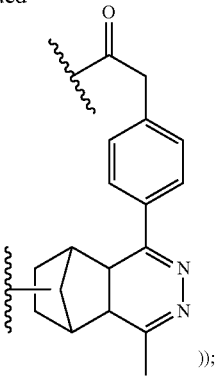

));

$Q^2$ is a linear group (e.g., $[-Q^3-Q^4-Q^5]_s$-), if p is 1, or a branched group (e.g., $[-Q^3-Q^4-Q^5]_s-Q^7([-Q^3-Q^4-Q^5]_s-(Q^7)_{p1})_{p2}$, where p1 is 0, 1, or 2, and p2 is 0, 1, 2, or 3), if p is an integer from 2 to 9; each $Q^3$ and each $Q^6$ is independently absent, —CO—, —NH—, —O—, —S—, —SO$_2$—, —OC(O)—, —C(O)O—, —NHC(O)—, —C(O)NH—, —CH$_2$—, —CH$_2$NH—, —NHCH$_2$—, —CH$_2$O—, or —OCH$_2$—;

each $Q^4$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, optionally substituted $C_{6-10}$ arylene, optionally substituted $C_{1-9}$ heteroarylene, or optionally substituted $C_{1-9}$ heterocyclylene;

each $Q^5$ is independently absent, —CO—, —NH—, —O—, —S—, —SO$_2$—, —CH$_2$—, —C(O)O—, —OC(O)—, —C(O)NH—, —NH—C(O)—, —NH—CH(R$^a$)—C(O)—, —C(O)—CH(R$^a$)—NH—, —OP(O)(OH)O—, or —OP(S)(OH)O—;

each $Q^7$ is independently optionally substituted hydrocarbon or optionally substituted heteroorganic (e.g., $C_{1-6}$ alkane-triyl, optionally substituted $C_{1-6}$ alkane-tetrayl, optionally substituted $C_{2-6}$ heteroalkane-triyl, or optionally substituted $C_{2-6}$ heteroalkane-tetrayl); and each R$^a$ is independently H or an amino acid side chain; provided that at least one of $Q^3$, $Q^4$, and $Q^5$ is present.

In some instances, for each occurrence of $[-Q^3-Q^4-Q^5]_s$-, at least one of $Q^3$, $Q^4$, and $Q^5$ is present.

In some instances, $Q^7$ may be a structure selected from the group consisting of:

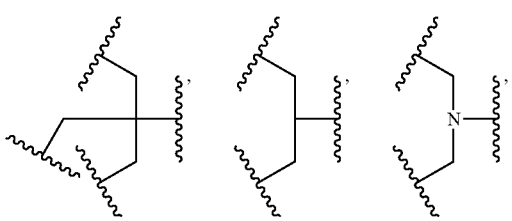

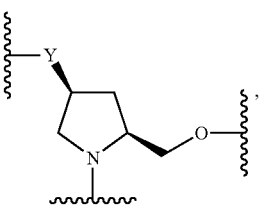

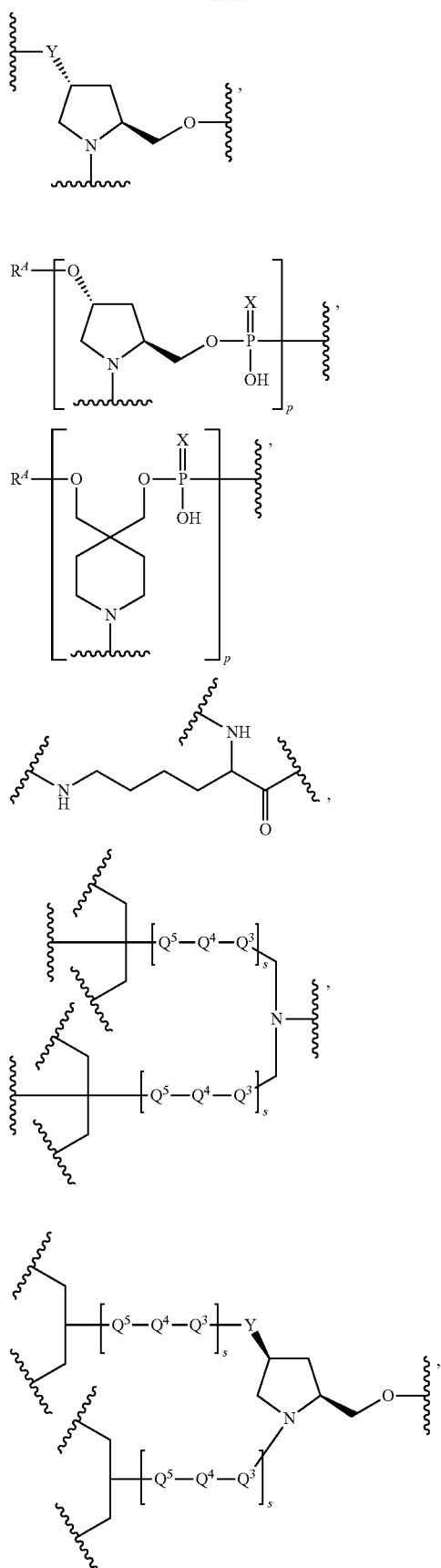

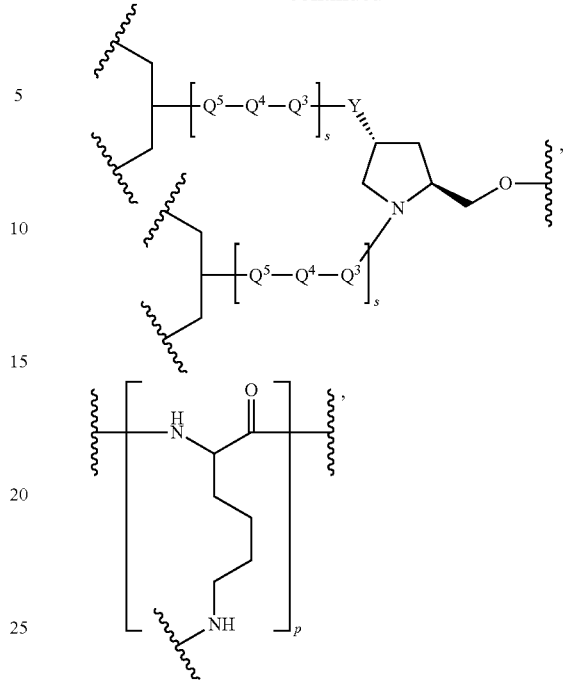

where $R^A$ is H or oligonucleotide, X is O or S, Y is O or NH, and the remaining variables are as described for formula (I).

Group -LinkA- may include a poly(alkylene oxide) (e.g., polyethylene oxide, polypropylene oxide, poly(trimethylene oxide), polybutylene oxide, poly(tetramethylene oxide), and diblock or triblock co-polymers thereof). In some embodiments, -LinkA- includes polyethylene oxide (e.g., poly(ethylene oxide) having a molecular weight of less than 1 kDa).

Hydrophobic Moieties

Advantageously, an oligonucleotide including a hydrophobic moiety may exhibit superior cellular uptake, as compared to an oligonucleotide lacking the hydrophobic moiety. Oligonucleotides including a hydrophobic moiety may therefore be used in compositions that are substantially free of transfecting agents. A hydrophobic moiety is a monovalent group (e.g., a bile acid (e.g., cholic acid, taurocholic acid, deoxycholic acid, oleyl lithocholic acid, or oleoyl cholenic acid), glycolipid, phospholipid, sphingolipid, isoprenoid, vitamin, saturated fatty acid, unsaturated fatty acid, fatty acid ester, triglyceride, pyrene, porphyrine, texaphyrine, adamantine, acridine, biotin, coumarin, fluorescein, rhodamine, Texas-Red, digoxygenin, dimethoxytrityl, t-butydimethylsilyl, t-butyldiphenylsilyl, cyanine dye (e.g., Cy3 or Cy5), Hoechst 33258 dye, psoralen, or ibuprofen) covalently linked to the oligonucleotide backbone (e.g., 5'-terminus). Non-limiting examples of the monovalent group include ergosterol, stigmasterol, β-sitosterol, campesterol, fucosterol, saringosterol, avenasterol, coprostanol, cholesterol, vitamin A, vitamin D, vitamin E, cardiolipin, and carotenoids. The linker connecting the monovalent group to the oligonucleotide may be an optionally substituted $C_{1-60}$ hydrocarbon (e.g., optionally substituted $C_{1-60}$ alkylene) or an optionally substituted $C_{2-60}$ heteroorganic (e.g., optionally substituted $C_{2-60}$ heteroalkylene), where the linker may be optionally interrupted with one, two, or three instances independently selected from the group consisting of an optionally substituted arylene, optionally substituted heterocyclylene, and optionally substituted cycloalkylene. The linker may be bonded to an oligonucleotide through, e.g., an oxygen atom attached to a 5'-terminal carbon atom, a 3'-terminal carbon atom, a 5'-terminal phosphate or phosphorothioate, a 3'-terminal phosphate or phosphorothioate, or an internucleoside linkage.

Cell Penetrating Peptides

One or more cell penetrating peptides (e.g., from 1 to 6 or from 1 to 3) can be attached to an oligonucleotide disclosed herein as an auxiliary moiety. The CPP can be linked to the oligonucleotide through a disulfide linkage, as disclosed herein. Thus, upon delivery to a cell, the CPP can be cleaved intracellularly, e.g., by an intracellular enzyme (e.g., protein disulfide isomerase, thioredoxin, or a thioesterase) and thereby release the polynucleotide.

CPPs are known in the art (e.g., TAT or $Arg_8$) (Snyder and Dowdy, 2005, Expert Opin. Drug Deliv. 2, 43-51). Specific examples of CPPs including moieties suitable for conjugation to the oligonucleotides disclosed herein are provided, e.g., in WO 2015/188197; the disclosure of these CPPs is incorporated by reference herein.

CPPs are positively charged peptides that are capable of facilitating the delivery of biological cargo to a cell. It is believed that the cationic charge of the CPPs is essential for their function. Moreover, the transduction of these proteins does not appear to be affected by cell type, and these proteins can efficiently transduce nearly all cells in culture with no apparent toxicity. In addition to full-length proteins, CPPs have also been used successfully to induce the intracellular uptake of DNA, antisense polynucleotides, small molecules, and even inorganic 40 nm iron particles suggesting that there is considerable flexibility in particle size in this process.

In one embodiment, a CPP useful in the methods and compositions of the invention includes a peptide featuring substantial alpha-helicity. It has been discovered that transfection is optimized when the CPP exhibits significant alpha-helicity. In another embodiment, the CPP includes a sequence containing basic amino acid residues that are substantially aligned along at least one face of the peptide. A CPP useful in the invention may be a naturally occurring peptide or a synthetic peptide.

Polymers

An oligonucleotide of the invention may include covalently attached neutral polymer-based auxiliary moieties. Neutral polymers include poly($C_{1-6}$ alkylene oxide), e.g., poly(ethylene glycol) and poly(propylene glycol) and copolymers thereof, e.g., di- and triblock copolymers. Other examples of polymers include esterified poly(acrylic acid), esterified poly(glutamic acid), esterified poly(aspartic acid), poly(vinyl alcohol), poly(ethylene-co-vinyl alcohol), poly (N-vinyl pyrrolidone), poly(ethyloxazoline), poly(alkylacrylates), poly(acrylamide), poly(N-alkylacrylamides), poly(N-acryloylmorpholine), poly(lactic acid), poly(glycolic acid), poly(dioxanone), poly(caprolactone), styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyurethane, N-isopropylacrylamide polymers, and poly(N,N-dialkylacrylamides). Exemplary polymer auxiliary moieties may have molecular weights of less than 100, 300, 500, 1000, or 5000 Da (e.g., greater than 100 Da). Other polymers are known in the art.

Nucleobase Modifications

Oligonucleotides of the invention may include one or more modified nucleobases.

Unmodified nucleobases include the purine bases adenine (A) and guanine (G), and the pyrimidine bases thymine (T), cytosine (C), and uracil (U). Modified nucleobases include 5-substituted pyrimidines, 6-azapyrimidines, alkyl or alkynyl substituted pyrimidines, alkyl substituted purines, and N-2, N-6 and O-6 substituted purines, as well as synthetic and natural nucleobases, e.g., 5-methylcytosine, 5-hydroxymethyl cytosine, xanthine, hypoxanthine, 2-aminoadenine, 6-alkyl (e.g., 6-methyl) adenine and guanine, 2-alkyl (e.g., 2-propyl) adenine and guanine, 2-thiouracil, 2-thiothymine, 2-thiocytosine, 5-halouracil, 5-halocytosine, 5-propynyl uracil, 5-propynyl cytosine, 5-trifluoromethyl uracil, 5-trifluoromethyl cytosine, 7-methyl guanine, 7-methyl adenine, 8-azaguanine, 8-azaadenine, 7-deazaguanine, 7-deazaadenine, 3-deazaguanine, 3-deazaadenine. Certain nucleobases are particularly useful for increasing the binding affinity of nucleic acids, e g., 5-substituted pyrimidines; 6-azapyrimidines; N2-, N6-, and/or O6-substituted purines. Nucleic acid duplex stability can be enhanced using, e.g., 5-methylcytosine. Non-limiting examples of nucleobases include: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deazaadenine, 7-deazaguanine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

The replacement of cytidine with 5-methylcytidine can reduce immunogenicity of oligonucleotides, e.g., those oligonucleotides having CpG units.

The replacement of one or more guanosines with, e.g., 7-deazaguanosine or 6-thioguanosine, may inhibit the antisense activity reducing G tetraplex formation within antisense oligonucleotides.

Sugar Modifications

Oligonucleotides of the invention may include one or more sugar modifications in nucleosides. Nucleosides having an unmodified sugar include a sugar moiety that is a furanose ring as found in ribonucleosides and 2'-deoxyribonucleosides.

Sugars included in the nucleosides of the invention may be non-furanose (or 4'-substituted furanose) rings or ring systems or open systems. Such structures include simple changes relative to the natural furanose ring (e.g., a six-membered ring). Alternative sugars may also include sugar surrogates wherein the furanose ring has been replaced with another ring system such as, e.g., a morpholino or hexitol ring system. Non-limiting examples of sugar moieties useful that may be included in the oligonucleotides of the invention include β-D-ribose, β-D-2'-deoxyribose, substituted sugars (e.g., 2',5', and bis substituted sugars), 4'-S-sugars (e.g., 4'-S-ribose, 4'-S-2'-deoxyribose, and 4'-S-2'-substituted ribose), bridged sugars (e.g., the 2'-O—CH$_2$-4' or 2'-O—(CH$_2$)$_2$-4' bridged ribose derived bicyclic sugars) and sugar surrogates (when the ribose ring has been replaced with a morpholino or a hexitol ring system).

Typically, a sugar modification may be, e.g., a 2'-substitution, locking, carbocyclization, or unlocking. A 2'-substitution is a replacement of 2'-hydroxyl in ribofuranose with 2'-fluoro, 2'-methoxy, or 2'-(2-methoxy)ethoxy. A locking modification is an incorporation of a bridge between 4'-carbon atom and 2'-carbon atom of ribofuranose. Nucleosides having a sugar with a locking modification are known in the art as bridged nucleic acids, e.g., locked nucleic acids (LNA), ethylene-bridged nucleic acids (ENA), and cEt nucleic acids. The bridged nucleic acids are typically used as affinity enhancing nucleosides.

Internucleoside Linkage Modifications

Oligonucleotides of the invention may include one or more internucleoside linkage modifications. The two main classes of internucleoside linkages are defined by the presence or absence of a phosphorus atom. Non-limiting examples of phosphorus-containing internucleoside linkages include phosphodiester linkages, phosphotriester linkages, phosphorothioate diester linkages, phosphorothioate triester linkages, morpholino internucleoside linkages, methylphosphonates, and phosphoramidate. Non-limiting examples of non-phosphorus internucleoside linkages include methylenemethylimino (—CH$_2$—N(CH$_3$)—O—CH$_2$—), thiodiester (—O—C(O)—S—), thionocarbamate (—O—C(O)(NH)—S—), siloxane (—O—Si(H)$_2$—O—), and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. Methods of preparation of phosphorous-containing and non-phosphorous-containing internucleoside linkages are known in the art.

Internucleoside linkages may be stereochemically enriched. For example, phosphorothioate-based internucleoside linkages (e.g., phosphorothioate diester or phosphorothioate triester) may be stereochemically enriched. The stereochemically enriched internucleoside linkages including a stereogenic phosphorus are typically designated S$_P$ or R$_P$ to identify the absolute stereochemistry of the phosphorus atom. Within an oligonucleotide, S$_P$ phosphorothioate indicates the following structure:

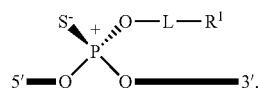

Within an oligonucleotide, R$_P$ phosphorothioate indicates the following structure:

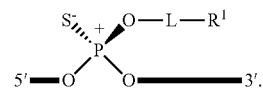

The oligonucleotides of the invention may include one or more neutral internucleoside linkages. Non-limiting examples of neutral internucleoside linkages include phosphotriesters, phosphorothioate triesters, methylphosphonates, methylenemethylimino (5'-CH$_2$—N(CH$_3$)—O-3'), amide-3 (5'-CH$_2$—C(=O)—N(H)-3'), amide-4 (5'-CH$_2$—N(H)—C(=O)-3'), formacetal (5'-O—CH$_2$—O-3'), and thioformacetal (5'-S—CH$_2$—O-3'). Further neutral internucleoside linkages include nonionic linkages including siloxane (dialkylsiloxane), carboxylate ester, carboxamide, sulfide, sulfonate ester, and amides (See for example: Carbohydrate Modifications in Antisense Research; Y. S. Sanghvi and P. D. Cook, Eds., ACS Symposium Series 580; Chapters 3 and 4, 40-65).

Terminal Modifications

Oligonucleotides of the invention may include a terminal modification, e.g., a 5-terminal modification or a 3'-terminal modification.

The 5' end of an oligonucleotide may be, e.g., hydroxyl, a hydrophobic moiety, a targeting moiety, 5' cap, phosphate, diphosphate, triphosphate, phosphorothioate, diphosphorothioate, triphosphorothioate, phosphorodithioate, diphosphorodithioate, triphosphorodithioate, phosphonate, phosphoramidate, a cell penetrating peptide, an endosomal escape moiety, or a neutral organic polymer. An unmodified 5'-terminus is hydroxyl or phosphate. An oligonucleotide having a 5' terminus other than 5'-hydroxyl or 5'-phosphate has a modified 5' terminus.

The 3' end of an oligonucleotide may be, e.g., hydroxyl, a targeting moiety, a hydrophobic moiety, phosphate, diphosphate, triphosphate, phosphorothioate, diphosphorothioate, triphosphorothioate, phosphorodithioate, disphorodithioate, triphosphorodithioate, phosphonate, phosphoramidate, a cell penetrating peptide, an endosomal escape moiety, or a neutral organic polymer (e.g., polyethylene glycol). An unmodified 3'-terminus is hydroxyl or phosphate. An oligonucleotide having a 3' terminus other than 3'-hydroxyl or 3'-phosphate has a modified 3' terminus.

The terminal modification (e.g., 5'-terminal modification) may be, e.g., a targeting moiety as described herein.

The terminal modification (e.g., 5'-terminal modification) may be, e.g., a hydrophobic moiety as described herein.

Complementarity

In some embodiments, oligonucleotides of the invention are complementary to an ATP7B target sequence over the entire length of the oligonucleotide. In other embodiments, oligonucleotides are at least 99%, 95%, 90%, 85%, 80%, or 70% complementary to the ATP7B target sequence. In further embodiments, oligonucleotides are at least 80% (e.g., at least 90% or at least 95%) complementary to the ATP7B target sequence over the entire length of the oligonucleotide and include a nucleobase sequence that is fully complementary to an ATP7B target sequence. The nucleobase sequence that is fully complementary may be, e.g., 6 to 20, 10 to 18, or 18 to 20 contiguous nucleobases in length.

An oligonucleotide of the invention may include one or more (e.g., 1, 2, 3, or 4) mismatched nucleobases relative to the target nucleic acid. In certain embodiments, a splice-switching activity against the target is reduced by such mismatch, but activity against a non-target is reduced by a greater amount. Thus, the off-target selectivity of the oligonucleotides may be improved.

Methods for Preparing Compositions

The present disclosure provides methods for preparing or generating compositions provided herein. A nucleic acid molecule, such as an oligonucleotide, comprising a targeted sequence may be generated, for example, by various nucleic acid synthesis approaches. For example, a nucleic acid molecule comprising a sequence targeted to a splice site may be generated by oligomerization of modified and/or unmodified nucleosides, thereby producing DNA or RNA oligonucleotides. Antisense oligonucleotides can be prepared, for example, by solid phase synthesis. Such solid phase synthesis can be performed, for example, in multi-well plates using equipment available from vendors such as Applied Biosystems (Foster City, Calif.). It is well known to use similar techniques to prepare oligonucleotides such as the phosphorothioates and alkylated derivatives. Oligonucleotides may be subjected to purification and/or analysis using methods known to those skilled in the art. For example, analysis methods may include capillary electrophoresis (CE) and electrospray-mass spectroscopy.

Pharmaceutical Compositions

An oligonucleotide of the invention may be included in a pharmaceutical composition. A pharmaceutical composition typically includes a pharmaceutically acceptable diluent or carrier. A pharmaceutical composition may include (e.g., consist of), e.g., a sterile saline solution and an oligonucleotide of the invention. The sterile saline is typically a pharmaceutical grade saline. A pharmaceutical composition may include (e.g., consist of), e.g., sterile water and an oligonucleotide of the invention. The sterile water is typically a pharmaceutical grade water. A pharmaceutical composition may include (e.g., consist of), e.g., phosphate-buffered saline (PBS) and an oligonucleotide of the invention. The sterile PBS is typically a pharmaceutical grade PBS.

Pharmaceutical compositions may include one or more oligonucleotides and one or more excipients. Excipients may be selected from water, salt solutions, alcohol, polyethylene glycols, gelatin, lactose, amylase, magnesium stearate, talc, silicic acid, viscous paraffin, hydroxymethylcellulose and polyvinylpyrrolidone.

Pharmaceutical compositions including an oligonucleotide encompass any pharmaceutically acceptable salts of the oligonucleotide. Pharmaceutical compositions including an oligonucleotide, upon administration to a subject (e.g., a human), are capable of providing (directly or indirectly) the biologically active metabolite or residue thereof. Accordingly, for example, the disclosure is also drawn to pharmaceutically acceptable salts of oligonucleotides. Suitable pharmaceutically acceptable salts include, but are not limited to, sodium and potassium salts. In certain embodiments, prodrugs include one or more conjugate group attached to an oligonucleotide, wherein the conjugate group is cleaved by endogenous enzymes within the body.

Lipid moieties have been used in nucleic acid therapies in a variety of methods. In certain such methods, the nucleic acid, such as an oligonucleotide, is introduced into preformed liposomes or lipoplexes made of mixtures of cationic lipids and neutral lipids. DNA complexes with mono- or poly-cationic lipids may form, e.g., without the presence of a neutral lipid. A lipid moiety may be, e.g., selected to increase distribution of a pharmaceutical agent to a particular cell or tissue. A lipid moiety may be, e.g., selected to increase distribution of a pharmaceutical agent to fat tissue. A lipid moiety may be, e.g., selected to increase distribution of a pharmaceutical agent to muscle tissue.

Pharmaceutical compositions may include a delivery system. Examples of delivery systems include, but are not limited to, liposomes and emulsions. Certain delivery systems are useful for preparing certain pharmaceutical compositions including those including hydrophobic compounds. Certain organic solvents such as dimethylsulfoxide may be used.

Pharmaceutical compositions may include one or more tissue-specific delivery molecules designed to deliver the one or more pharmaceutical agents of the present invention to specific tissues or cell types. For example, pharmaceutical compositions may include liposomes coated with a targeting moiety as described herein.

Pharmaceutical compositions may include a co-solvent system. Certain co-solvent systems include, e.g., benzyl alcohol, a nonpolar surfactant, a water-miscible organic polymer, and an aqueous phase. Such co-solvent systems may be used, e.g., for hydrophobic compounds. A non-limiting example of a co-solvent system is the VPD co-solvent system, which is a solution of absolute ethanol including 3% w/v benzyl alcohol, 8% w/v of the nonpolar surfactant Polysorbate 80 ™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

Pharmaceutical compositions may be prepared for administration by injection or infusion (e.g., intravenous, subcutaneous, intramuscular, intrathecal, intracerebroventricular, etc.). A pharmaceutical composition may include, e.g., a carrier and may be formulated, e.g., in aqueous solution, e.g., water or physiologically compatible buffers, e.g., Hanks's solution, Ringer's solution, or physiological saline buffer. Other ingredients may also be included (e.g., ingredients that aid in solubility or serve as preservatives). Injectable suspensions may be prepared, e.g., using appropriate liquid carriers, suspending agents and the like. Certain pharmaceutical compositions for injection are presented in unit dosage form, e.g., in ampoules or in multi-dose containers. Certain pharmaceutical compositions for injection may be, e.g., suspensions, solutions, or emulsions in oily or aqueous vehicles, and may contain excipients (e.g., suspending, stabilizing and/or dispersing agents). Certain solvents suitable for use in pharmaceutical compositions for injection include, but are not limited to, lipophilic solvents and fatty oils, e.g., sesame oil, synthetic fatty acid esters (e.g., ethyl oleate or triglycerides), and liposomes.

Methods of the Invention

The invention provides methods of using oligonucleotides of the invention.

A method of the invention may be a method of increasing the level of exon 6-containing ATP7B mRNA molecules in a cell expressing an aberrant ATP7B gene by contacting the cell with the antisense oligonucleotide of the invention.

A method of the invention may be a method of treating Wilson disease in a subject having an aberrant ATP7B gene by administering a therapeutically effective amount of the antisense oligonucleotide of the invention or a pharmaceutical composition of the invention to the subject in need thereof.

The oligonucleotide of the invention or the pharmaceutical composition of the invention may be administered to the subject using methods known in the art. For example, the oligonucleotide of the invention or the pharmaceutical composition of the invention may be administered parenterally (e.g., intravenously, intramuscularly, subcutaneously, transdermally, intranasally, or intrapulmonarily) to the subject.

Dosing is typically dependent on a variety of factors including, e.g., severity and responsiveness of the disease state to be treated. The treatment course may last, e.g., from several days to several months, or until a cure is effected or a diminution of the disease state is achieved. Optimal dosing schedules can be calculated from measurements of drug accumulation in the body of the patient. Thus, optimum dosages, dosing methodologies and repetition rates can be established as needed. Optimum dosages may vary depending on the relative potency of individual oligonucleotides, and can generally be estimated based on $EC_{50}$s found to be effective in in vitro and in vivo animal models. In general, dosage may be from 0.01 μg to 1 g per kg of body weight, and may be given once or more daily, weekly, monthly, bimonthly, trimonthly, every six months, annually, or biannually. Frequency of dosage may vary. Repetition rates for dosing may be established, for example, based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 1 g per kg of body weight, e.g., once daily, twice daily, three times daily, every other day, weekly, biweekly, monthly, bimonthly, trimonthly, every six months, annually or biannually.

Methods of treating Wilson disease in a subject in need thereof may also include administering to the subject a pharmaceutically acceptable chelating agent or a pharmaceutically acceptable salt of zinc. Non-limiting examples of pharmaceutically acceptable salts of zinc include zinc acetate, zinc gluconate, and zinc sulfate. Non-limiting examples of pharmaceutically acceptable chelating agents include D-penicillamine, trientine, sodium mercaptosuccinate, dimercaptosuccinic acid, and tetrathiomolybdate. In some embodiments, the method includes administering to the subject a pharmaceutically acceptable salt of zinc (e.g., zinc acetate, zinc gluconate, or zinc sulfate). In one example, an oligonucleotide of the invention and a pharmaceutically acceptable chelating agent or salt of zinc are administered together in the same pharmaceutical composition. In another example, an oligonucleotide of the invention and a pharmaceutically acceptable chelating agent or salt of zinc are administered separately at about the same time (e.g., one minute apart or less, or five minutes apart or less). In some embodiments, an oligonucleotide of the invention and a pharmaceutically acceptable chelating agent or salt of zinc are administered separately via the same route of administration (e.g., intravenous injection). In some embodiments, an oligonucleotide of the invention and a pharmaceutically acceptable chelating agent or salt of zinc are administered separately via different routes of administration (e.g., intravenous injection of an oligonucleotide of the invention and oral administration of a pharmaceutically acceptable chelating agent or salt of zinc).

In some embodiments, an oligonucleotide of the invention is administered prior to a chelating agent or salt of zinc. In further embodiments, an oligonucleotide of the invention is administered within 1 hour of the chelating agent or salt of zinc administration (e.g., before, e.g., 15 min, 30 min, or 1 hour before). In some embodiments, an oligonucleotide of the invention is administered within 12 hours of the chelating agent or salt of zinc administration (e.g., before, e.g., 1, 2, 3, 4, 5, 6, 7, 8, 9, 10, 11, or 12 hours before). In certain embodiments, an oligonucleotide of the invention is administered within 24 hours of the chelating agent or salt of zinc administration (e.g., before, e.g., 12 or 24 hours before). In particular embodiments, an oligonucleotide of the invention is administered within 1 week of the chelating agent or salt of zinc administration (e.g., before, e.g., 1, 2, 3, 4, 5, or 6 days before). In some embodiments, an oligonucleotide of the invention is administered within 1 month of the chelating agent or salt of zinc administration (e.g., before, e.g., 1, 2, 3, or 4 weeks before).

In some embodiments, an oligonucleotide of the invention is administered after a chelating agent or salt of zinc. In further embodiments, an oligonucleotide of the invention is administered within 1 hour of the chelating agent or salt of zinc administration (e.g., after, e.g., 15 min, 30 min, or 1 hour after). In some embodiments, an oligonucleotide of the invention is administered within 12 hours of the chelating agent or salt of zinc administration (e.g., after, e.g., 1, 2, 3, 4, 5, 6, 7, 8, 9, 10, 11, or 12 hours after). In certain embodiments, an oligonucleotide of the invention is administered within 24 hours of the chelating agent or salt of zinc administration (e.g., after, e.g., 12 or 24 hours after). In particular embodiments, an oligonucleotide of the invention is administered within 1 week of the chelating agent or salt of zinc administration (e.g., after, e.g., 1, 2, 3, 4, 5, or 6 days after). In some embodiments, an oligonucleotide of the invention is administered within 1 month of the chelating agent or salt of zinc administration (e.g., after, e.g., 1, 2, 3, or 4 weeks after).

EXAMPLES

The following materials, methods, and examples are illustrative only and not intended to be limiting.

Materials and Methods

In general, the practice of the present invention employs, unless otherwise indicated, conventional techniques of chemistry, molecular biology, recombinant DNA technology, and standard techniques in electrophoresis. See, e.g., Sambrook, Fritsch and Maniatis, Molecular Cloning: Cold Spring Harbor Laboratory Press (1989) and Current Protocols in Molecular Biology, eds. Ausubel et al., John Wiley & Sons (1992).

Oligonucleotides. All antisense oligonucleotides used were obtained from Integrated DNA Technologies Inc. (USA). All bases in the antisense oligonucleotides were 2'-O-methoxyethyl-modified (MOE) with a full phosphorothioate backbone.

Construction of ATP7B minigenes. Minigene plasmids for ATP7B exon 6 were designed to contain fragments corresponding to exon 5 to 7 of the genomic locus of ATP7B gene, including complete intronic sequences. To minimize aberrant splicing of the transcribed mRNA fragments, consensus splice acceptor sequences of exon 5 were removed by deleting nine nucleotides from the 5' end of exon 5, likewise consensus splice donor sequences of exon 7 were removed by deleting 40 nucleotides from the 3' end of exon 7. Minigenes were constructed by DNA assembly of PCR fragments that were amplified from HEK293T genomic DNA using KOD Hot Start DNA polymerase (Novagen). For the wild-type minigene, the full fragment was amplified with primers P461 (GATCCACCGGTCGCCAC-CATGACCTGCGCGTCCTGTGTC) (SEQ ID: 165) and P463 (TCCTCGCCCTTGCTCACCATGGACAGTCCTG-GAATGATGTTGTGG) (SEQ ID: 166). For the mutant minigene, the NM_000053.3(ATP7B):c.1934T>G (p.Met645Arg) variant was introduced by site-directed mutagenesis of two overlapping fragments which were amplified with primer combination P461 (SEQ ID: 165) and P465 (CTGCTTTATTTCCCTCTTGTGGTCCAAGTGAT-GAGC) (SEQ ID: 167) and primer combination P464 (GACCACAAGAGG-GAAATAAAGCAGTAGGTAGAACAC) (SEQ ID: 168) and P463 (SEQ ID: 166) respectively. PCR fragments were cloned into mClover2 plasmid that was linearized with primers P459 (ATGGTGAGCAAGGGCGAGGA) (SEQ ID: 169) and P460 (CATGGTGGCGACCGGTGGAT) (SEQ ID: 170) using a NEBuilder HiFi DNA Assembly Kit (New England Biolabs) according to manufacturer's instructions. Plasmid DNA was isolated using the Presto Mini Plasmid Kit (Geneaid).

HepG2 mutant line, 2F3. This line was created from HepG2 cells by inserting the M645R variant using a CRISPR/Cas 9 according to commonly used molecular biology techniques. The resulting 2F3 line carries the M645R variant at one allele and a large plasmid insertion at the other. This insertion has been assumed to render that allele unable to produce functional protein, thus creating a situation analogous to a compound heterozygote, consistent with what found in Wilson disease patients (Margarit et al, *Clin Genet.*, 68:61-68, 2005).

Cell culture. HEK293T cells were grown in Iscove's Modified Dulbecco's Medium (Gibco) supplemented with 10% (v/v) Cosmic Calf Serum (HyClone), 2 mM L-Glutamine (Gibco) and 1% antibiotics (100-U/ml penicillin G and 100-ug/ml streptomycin, Gibco) in a humidified incubator at 37° C. with 5% $CO_2$. Upon reaching confluency the cells were passaged by washing with Phosphate-Buffered Saline followed by Trypsin (Gibco) dissociation and plated in 10 to 20-fold dilution. HepG2 wild-type and mutant 2F3 cells were grown in Dulbecco's Modified Eagle's Medium (Gibco) supplemented with 10% heat inactivated fetal bovine serum (Gibco) in a humidified incubator at 37° C. with 5% $CO_2$. Upon reaching confluency the cells were passaged by washing with Phosphate-Buffered Saline followed by TrypLE (Gibco) dissociation and plated in a culture flask in 2 to 4-fold dilution.

Transfection of HEK293T cells with minigene plasmids. For transfection of HEK293T cells with minigene plasmids, 300,000 cells were plated in 1 ml of complete medium with antibiotics in 12-well tissue culture plates and incubated at 37° C. and 5% $CO_2$ for 24 hours. Plasmid transfection mixes were made by combining 1,000 ng of plasmid DNA (~5 μl) diluted in 50 μl Opti-MEM reduced serum medium (Gibco) with 3.0 μl X-tremeGENE HP DNA Transfection Reagent solution (Roche). Plasmid transfection mixes were incubated at room temperature for 20 minutes and then added to the HEK293T cells, which were subsequently incubated at 37° C. and 5% $CO_2$. After 24 hours transfection media was replaced with 2,000 μl complete media. 48 hours after transfection, cells were lysed for RNA isolation and RT-PCR analysis.

Co-transfection of HEK293T cells with antisense oligonucleotides and minigene plasmids. Antisense oligonucleotides and minigene plasmids were co-transfected into HEK293T cells in 96-well format. Antisense oligonucleotide stock solutions (100 μM) were diluted to 5 μM in Opti-MEM reduced serum medium (Gibco). Antisense oligonucleotides were transfected at absolute amounts of 50 pmol of an antisense oligonucleotide per well containing 50,000 HEK293T cells. For this, 10-μl aliquots of 5 μM antisense oligonucleotide solutions were transferred to the wells of a 96-well tissue culture plate and 10 μl lipid transfection reagent solution containing 9.7 μl Opti-MEM and 0.3 μl Lipofectamine RNAiMAX (Invitrogen) was added to the wells. Antisense oligonucleotide-lipid complexes in the mixture were formed by gentle mixing through pipetting twice and subsequent tapping of the plate followed by incubation for 20 minutes at room temperature. Next, 50,000 HEK293T cells in 100 μl complete media solution without antibiotics were added to the antisense oligonucleotide-lipid complexes and incubated for five hours at 37° C. and 5% $CO_2$. After incubation, cells were transfected with minigene plasmids. For this, plasmid transfection mixes were made by combining 5 μl containing 200 ng of plasmid diluted in Opti-MEM with 0.6 μl X-tremeGENE 9 DNA Transfection Reagent solution (Roche). Plasmid transfection mixes were incubated at room temperature for 20 minutes and then added to the HEK293T cells, which were subsequently incubated at 37° C. and 5% $CO_2$. After 24 hours transfection media was replaced with 200 μl complete media. 48 hours after transfection, cells were lysed for RNA isolation and RT-PCR analysis.

Transfection HepG2 wild-type and mutant 2F3 cells. All reagents were used according to manufacturer's recommendations. Cells were suspended by incubation with TrypLE for 15-20 minutes and diluted to 250000-500000 cells per milliliter in Dulbecco's Modified Eagle's Medium with 10% heat inactivated fetal calf serum. 50 pmol of oligonucleotide in transfection medium, containing RNAiMAX (Invitrogen) and Opti-MEM (Gibco), was combined with 25000-50000 cells from the culture suspension above. RNA was collected 48 hours after transfection unless otherwise stated.

RNA preparation. RNA was prepared by using a Single-Shot Cell Lysis kit (Bio-Rad) or RNeasy total RNA kit (QIAGEN) according to manufacturer's recommendations, alternatively Direct-zol TM-96 MagBead RNA (Zymo Research) was used according to manufacturer's recommendations except wherein all washes with volumes of 500 μL only 300 μL was used and for all rpm speeds of 900 rpm, 1050 rpm was used.

RT-PCR analysis. Synthesis of first-strand cDNA was performed with the ImProm-II Reverse Transcription System (Promega) according to manufacturer's recommendations with minor modifications. 50-300 ng of purified RNA were incubated in a 96-well PCR plate with 1 μl Oligo-dT-VN primer (100 μM, TTTTTTTTTTTTTTTTTT VN) for 5 min at 70° C., followed by rapid cooling for 5 min at 4° C. 14.5-μl of reverse tanscriptase mixture, containing 20 Units ImProm-II Reverse Transcriptase, reaction buffer, 4 mM $MgCl_2$, 0.5 mM dNTPs (FroggaBio) and 40 units RNAse Inhibitor (Bioshop) was added to the RNA-Oligo-dT-VN reaction anpd incubated for 5 min at 25° C., 60 min at 42° C. and finally cooled to 12° C. Target-specific splicing fragments were amplified by PCR. PCR primers for HepG2 wild-type and mutant 2F3 cell experiments were CCAGCAAAGCCCTTGTTAAG (SEQ ID NO: 156) and GCTCGTTGCTGGGTATCAG (SEQ ID NO: 157). PCR primers for minigene experiments were GATCACAGG-GATGACCTGC (SEQ ID NO: 158) and GTT-TACGTCGCCGTCCAG (SEQ ID NO: 159). PCR reactions contained 5 μl first-strand cDNA product, 0.4 μM forward primer, 0.4 μM reverse primer, 300 μM of each dNTP, 25 mM Tricine, 7.0% Glycerol (m/v), 1.6% DMSO (m/v), 2 mM $MgCl_2$, 85 mM NH4-acetate (pH8.7), and 1 unit Taq DNA polymerase (FroggaBio) in a total volume of 25 μl. Fragments were amplified by a touchdown PCR program (95° C. for 120 sec; 10 cycles of 95° C. for 20 sec, 68° C. for 30 sec with a decrement of 1° C. per cycle, and 72° C. for 60 sec; followed by 30 cycles of 95'C for 20 sec, 58° C. for 30 sec, and 72° C. for 60 sec; 72° C. for 180 sec).

Capillary electrophoresis. Samples were analyzed using a LabChip GX Touch Nucleic Acid Analyzer (GE) using a DNA 1K Hi Sensitivity LabChip and associated reagents (GE) according to manufacturer's recommendations.

Western blotting. Cells were grown and transfected as above. After 48 hours the media was removed, and cells were rinsed with DPBS. The cells were suspended with TrypLE (Gibco) and pelleted. The TrypLE was removed and 150 µl of ice cold RIPA buffer (SIGMA) with 1×HALT protease inhibitor (Pierce Biotechnology) was added to the well. The solution was placed on ice for 10 minutes and then centrifuged at 15000 rcf at 4° C. The supernatant was put into a fresh tube and the pellet was discarded. Using a protein quantification kit (Pierce) the protein concentrations was determined. Twenty to thirty µg of lysate protein was heated at 70° C. with Nupage buffer (Novex) and loaded onto a 10% Bis-Tris gel (Invitrogen). The gel was run for ~40 minutes at 200V in 1×MOPS buffer (Novex). The gel was removed and transferred to a PVDF membrane (GE) on ice for 90 minutes at 350 mA constant current. After transfer, the membrane was blocked in TBST-5% milk for 60 minutes at room temperature. After blocking, primary antibodies for GAPDH (Abcam) and ATP7B (Abcam) were added in TBSB-1% milk and refrigerated at 4° C. overnight. The membrane was then rinsed with TBST for 5 minutes 5 times. Secondary antibodies conjugated with horseradish peroxidase (Cell Signalling technology) were added to the solution for 60 minutes at room temperature. The membrane was then rinsed with TBST for 5 minutes 5 times. The images were recorded with a GE AI600RGB device.

Copper sensitivity assay. Cells were grown and transfected as stated above. Cells were then transfected with an antisense oligonucleotide or not transfected for control. Forty-eight hours after transfection, CuCl2 (Sigma) was prepared in deionized water at a concentration of 0.5M. This was then diluted in DMEM supplemented with 10% fetal calf serum to final concentrations of 0.2 mM, 0.5 mM, 0.75 mM, 1.0 mM, and 1.25 mM. A media change was then performed on the cells using the media+CuC12. After 48 hours the cell viability was read with a Neo2 instrument (Biotek) using CellTiter-Fluor™ Cell Viability Assay (Promega). Data was normalized to the copper-free treatment within groups.

Figure 1B:
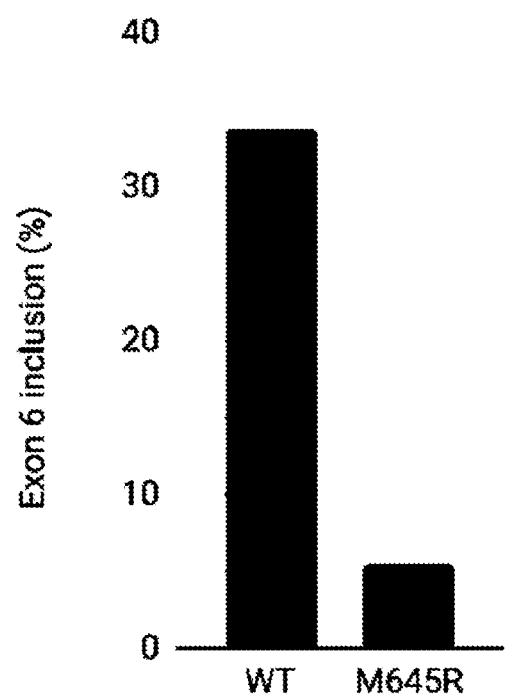
FIG. 1B depicts the percentage of exon 6 inclusion in ATP7B minigenes calculated by quantification of the RT-PCR fragments observed in FIG. 1A.

Example 1 the Splicing of ATP7B Exon 6 is Disrupted in the Chr13:52535985:A:C [Hg19/b37] Variant and can be Partially Rescued Through the Use of Antisense Oligonucleotides To confirm exon 6 skipping in the chr13:52535985:A:C [hg19/b37] (M645R) variant, wild type and variant containing minigenes were constructed containing exons 5-7 and the corresponding introns, 5 and 6. Minigenes were then transfected into HEK293T cells to examine the effect of the M645R variant on splicing. As seen in FIG. 1A, wildtype minigenes showed both exon 6 inclusion, represented by the upper band, and exclusion. M645R mutants, however, showed no exon 6 inclusion indicating the chr13:52535985: A:C [hg19/b37] mutation induces exon 6 skipping. The results of the experiment in FIG. 1A were replicated and quantified. As seen in FIG. 1B. there is a robust (standard deviations of 5.7% and 1.3% for wildtype and M645R minigenes respectively) decrease in exon 6 inclusion due to the chr13:52535985:A:C [hg19/b37] mutation.

Figure 2A:
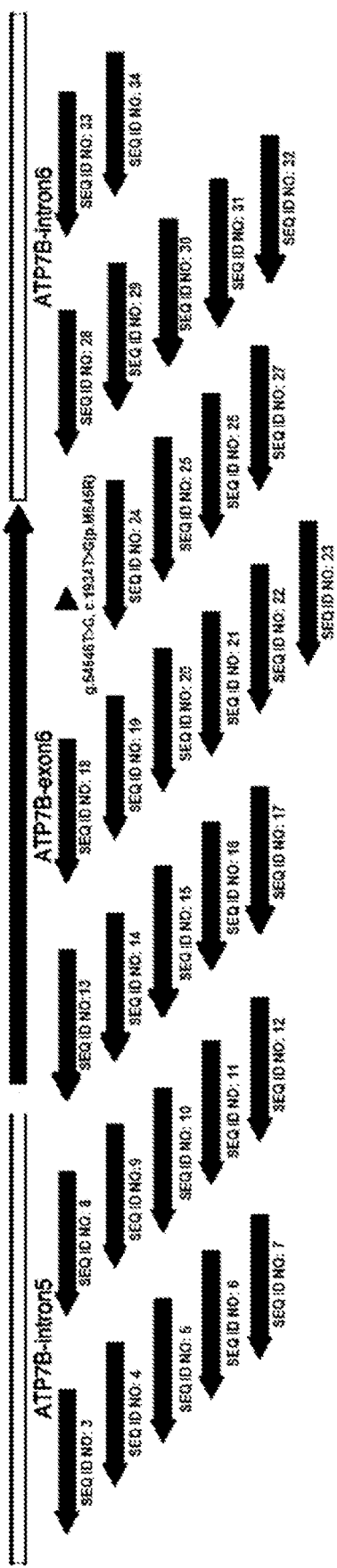
FIGS. 2A, 2B, and 2C show antisense oligonucleotide target ("hotspot") identification by coarse-tilling of ATP7B minigenes.
Figure 2B:
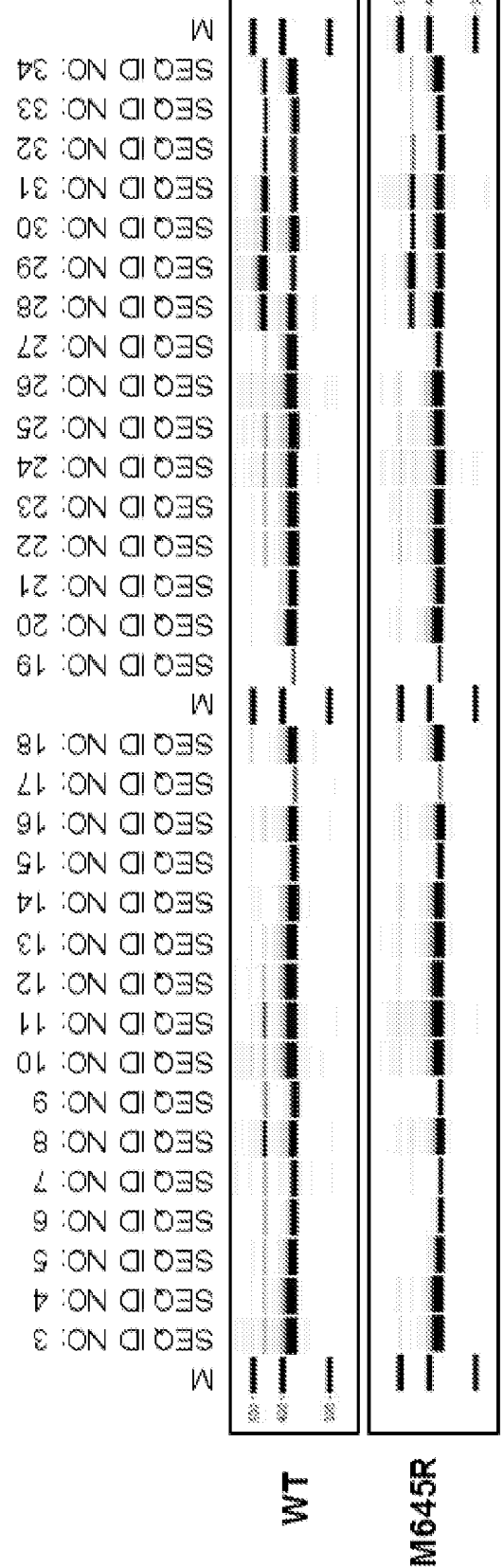
Figure 2C:
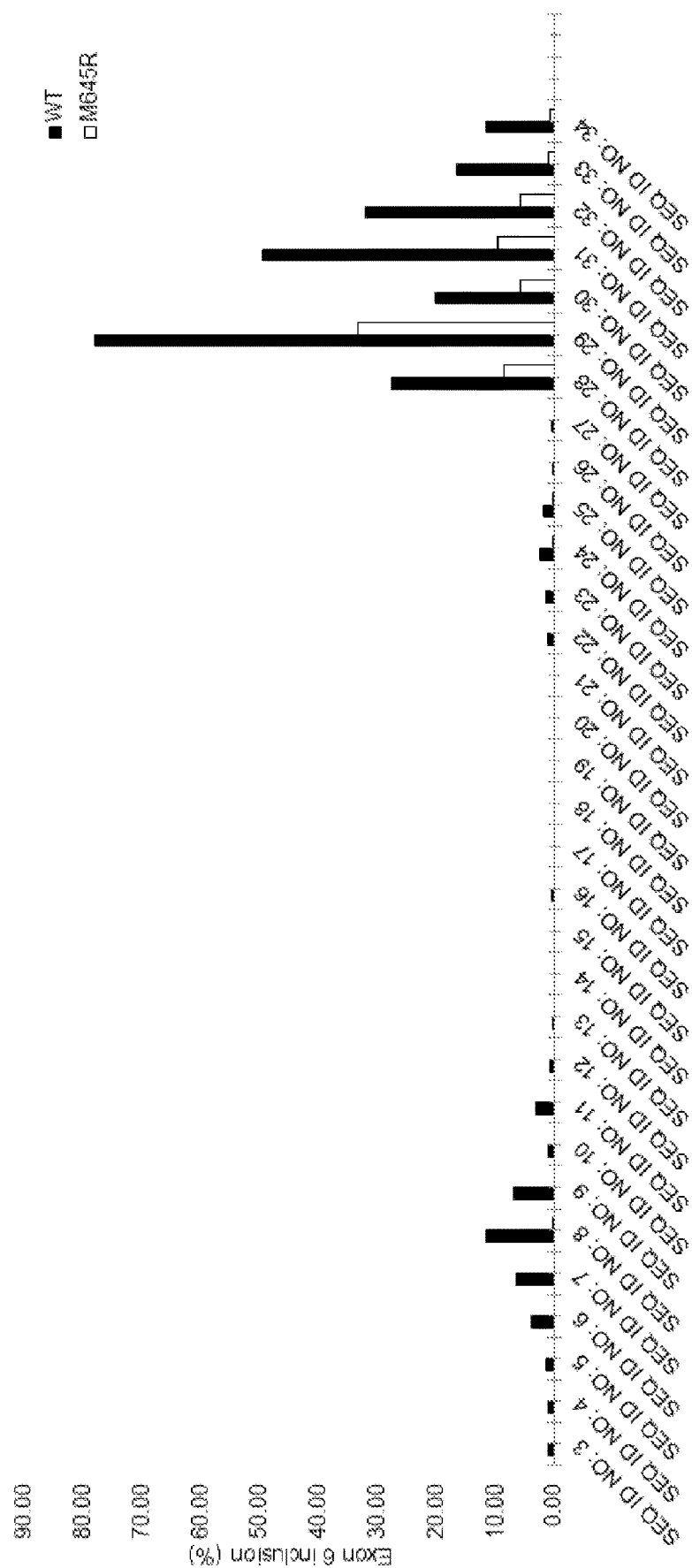

To examine the ability of antisense oligonucleotides to promote exon 6 inclusion in the M645R variant the minigenes above were co-transfected with antisense oligonucleotides having sequences set forth in SEQ ID NOs: 3-34 (see Table 1). Antisense oligonucleotides were tiled along exon 6 and the surrounding introns. FIG. 2A depicts the location of the targeted ASOs relative to exon 6 and the surrounding introns. FIG. 2B shows the RT-PCR samples measured by capillary electrophoresis. A 100 bp DNA ladder is shown for size reference with the exon 6 inclusion band at 445 bp and exclusion band at 368 bp. These results were quantified and are depicted in FIG. 2C. Observing both FIGS. 2B and 2C it is clear that targeting the intronic regions surrounding exon 6 induces exon 6 inclusion of both wildtype and M645R variant minigenes. These observations suggest antisense oligonucleotides targeting these regions or "hotspots" (positions 54522-54593 and 54665-54718 in SEQ ID NO: 1; chr13:52536038-52536109 and chr13:52535966-52535913), e.g., those complementary to a nucleobase sequence in SEQ ID NOs: 3-12 for hotspot 1 and SEQ ID NOs: 28-34 for hotspot 2, may be particularly useful in the treatment of Wilson disease associated with exon 6 skipping (e.g., Wilson disease caused by the M645R mutation).

TABLE 1

| SEQ ID NO | Sequence |
| --- | --- |
| 3 | GTACTTGGTTAAAATATGCA |
| 4 | AGGAAGGTACTTGGTTAAAA |
| 5 | AAAAGGAGGAAGGTACTTGG |
| 6 | TGGGGAAAAAGGAGGAAGGT |
| 7 | AGGGGTGGGGAAAAAGGAGG |
| 8 | AAAGAGAGGGGTGGGGAAAA |
| 9 | CATTAAAAAGAGAGGGGTGG |
| 10 | CTTGTCATTAAAAAGAGAGG |
| 11 | AATTTCCTTGTCATTAAAAA |
| 12 | AAAGCCAATTTCCTTGTCAT |
| 13 | AGCATGAAAGCCAATTTCCT |
| 14 | AGGGAAGCATGAAAGCCAAT |
| 15 | TGGGCCAGGGAAGCATGAAA |
| 16 | TTTCTCTGGGCCAGGGAAGC |
| 17 | TGGGGTTTCTCTGGGCCAGG |
| 18 | GAGCGTTGGGGTTTCTCTGG |
| 19 | AGTGATGAGCGTTGGGGTTT |
| 20 | GGTCCAAGTGATGAGCGTTG |
| 21 | CTTGTGGTCCAAGTGATGAG |
| 22 | TTCCCTCTTGTGGTCCAAGT |
| 23 | CTTTATTTCCCTCTTGTGGT |
| 24 | TACTGCTTTATTTCCCTCTT |
| 25 | TCTACCTACTGCTTTATTTC |

TABLE 1-continued

| SEQ ID NO | Sequence |
|---|---|
| 26 | TTGTGTTCTACCTACTGCTT |
| 27 | TATCTTTTGTGTTCTACCTA |
| 28 | GAGTTTATCTTTTGTGTTCT |
| 29 | GAGCTGGAGTTTATCTTTTG |
| 30 | AGATGAGAGCTGGAGTTTAT |
| 31 | GACTTAGATGAGAGCTGGAG |
| 32 | GGAAGGGACTTAGATGAGAG |
| 33 | GGTAGAGGAAGGGACTTAGA |
| 34 | GCCCAGGTAGAGGAAGGGAC |

Example 2 Characterization of Target Regions (Hot Spots) for Increasing Inclusion of ATP7B Exon 6

To explore the possible use of splice-switching oligonucleotides as a treatment for Wilson disease patients carrying the M645R variant, a hepatic cell line, HepG2, carrying this mutation, 2F3, was derived. The 2F3 line carries the M645R variant at one allele and a large plasmid insertion at the other. This insertion is assumed to render that allele unable to produce functional protein, thus creating a situation analogous to a compound heterozygote, consistent with what found in Wilson disease patients.

The oligonucleotides listed in Table 2 were transfected into 2F3 cells, and RT-PCR products were analyzed using capillary electrophesis. These oligonucleotides were designed to hybridize to the above-identified hotspots and to expand the search for additional hotspots. Percent spliced in (PSI) for exon 6 was then calculated as well as the change in percent spliced in compared toan inactive control antisense oligonucleotide (dPSI) (Table 2). As seen in Table 2, certain antisense oligonucleotides have a negative dPSI indicating an increase in exon 6 exclusion (e.g., SEQ ID NOs: 115-118) which is opposite of the intended effect. Antisense oligonucleotides which are targeted to intronic regions either side of exon 6 are effective showing positive dPSs.

Figure 3:
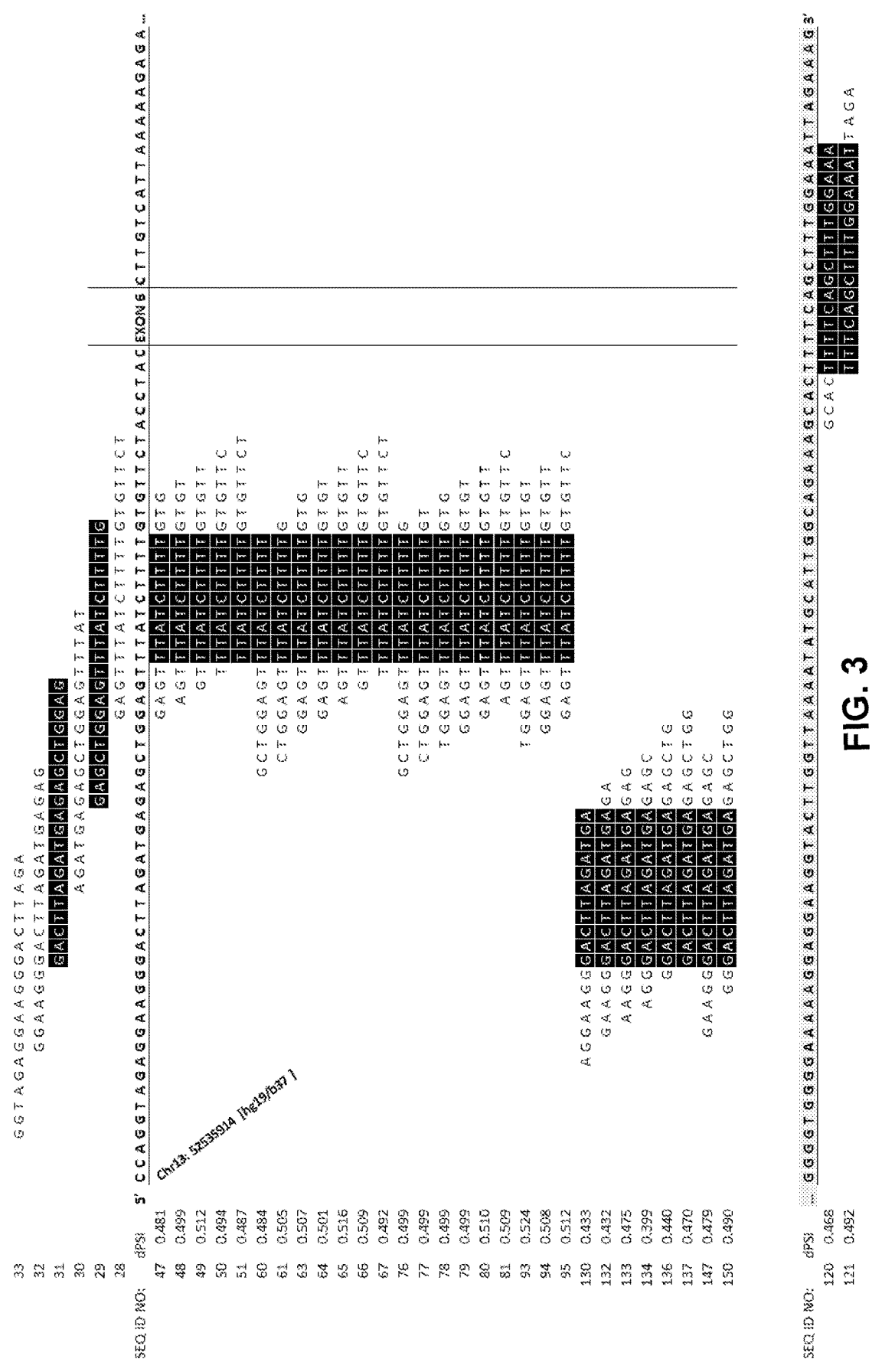

Certain oligonucleotides with high dPSs were aligned to the reference genome chr13: 52535914-52536146[hg9/b37] (SEQ ID NOs:28-33, 47-51, 60, 61, 63-67, 76-81, 93-95, 120, 121, 130, 132, 133-137, 147, and 150). As seen in FIG. 3, a third hotspot for antisense oligonucleotide binding to induce exon 6 inclusion in ATP71BM645R mutants was discovered spanning the area covered by antisense oligonucleotides having sequences set forth in SEQ ID NOs: 119-124 (genomic antisense: positions 54472-54516 in SEQ ID NO:1; chr3:52536115-52536159), in addition to the areas covered by antisense oligonucleotides having sequences set forth in SEQ ID NOs: 3-12 (genomic antisense: positions 54522-54593 in SEQ ID NO:1; chr3:52536038-52536109) and SEQ ID NOs:28-34 (genomic antisense: positions 54665-54718 in SEQ ID NO:1; chr3:52535913-52535966). Three exemplary core sequences were also identified in these areas: SEQ ID NO: 160 (genomic sense: TTATCTTTT; genomic antisense: positions 54672-54680 in SEQ ID NO:1), SEQ ID NO: 161 (genomic sense: GACTTAGATGA; genomic antisense: positions 54691-54701 in SEQ ID NO:1), and SEQ ID NO:162 (genomic sense: TTTCAGCTTTGGAAA; genomic antisense:positions 54492-54506).

TABLE 2

| SEQ ID NO | PSI | sequence | Start Chr13 [hg19/b37] | End Chr13 [hg19/b37] | length | dPSI |
|---|---|---|---|---|---|---|
| 29 | 0.94903506 | GAGCTGGAGTTTATCTTTTG | 52535941 | 52535960 | 20 | 0.491132 |
| 30 | 0.93643194 | AGATGAGAGCTGGAGTTTAT | 52535935 | 52535954 | 20 | 0.478529 |
| 35 | 0.70974518 | AGATGAGAGCTGGAGT | 52535935 | 52535950 | 16 | 0.251842 |
| 36 | 0.79611546 | GATGAGAGCTGGAGTT | 52535936 | 52535951 | 16 | 0.338213 |
| 37 | 0.80660668 | ATGAGAGCTGGAGTTT | 52535937 | 52535952 | 16 | 0.348704 |
| 38 | 0.62920358 | TGAGAGCTGGAGTTTA | 52535938 | 52535953 | 16 | 0.171301 |
| 39 | 1 | GAGAGCTGGAGTTTAT | 52535939 | 52535954 | 16 | 0.542097 |
| 40 | 0.82915652 | AGAGCTGGAGTTTATC | 52535940 | 52535955 | 16 | 0.371254 |
| 41 | 0.80242893 | GAGCTGGAGTTTATCT | 52535941 | 52535956 | 16 | 0.344526 |
| 42 | 0.93324554 | AGCTGGAGTTTATCTT | 52535942 | 52535957 | 16 | 0.475343 |
| 43 | 0.91806589 | GCTGGAGTTTATCTTT | 52535943 | 52535958 | 16 | 0.460163 |
| 44 | 0.92097701 | CTGGAGTTTATCTTTT | 52535944 | 52535959 | 16 | 0.463074 |
| 45 | 0.88136593 | TGGAGTTTATCTTTTG | 52535945 | 52535960 | 16 | 0.423463 |
| 46 | 0.92978378 | GGAGTTTATCTTTTGT | 52535946 | 52535961 | 16 | 0.471881 |
| 47 | 0.93878061 | GAGTTTATCTTTTGTG | 52535947 | 52535962 | 16 | 0.480878 |
| 48 | 0.95719947 | AGTTTATCTTTTGTGT | 52535948 | 52535963 | 16 | 0.499297 |

TABLE 2-continued

| SEQ ID NO | PSI | sequence | Start Chr13 [hg19/b37] | End Chr13 [hg19/b37] | length | dPSI |
| --- | --- | --- | --- | --- | --- | --- |
| 49 | 0.96989269 | GTTTATCTTTTGTGTT | 52535949 | 52535964 | 16 | 0.51199 |
| 50 | 0.95199346 | TTTATCTTTTGTGTTC | 52535950 | 52535965 | 16 | 0.494091 |
| 51 | 0.94531532 | TTATCTTTTGTGTTCT | 52535951 | 52535966 | 16 | 0.487412 |
| 52 | 0.57919401 | AGATGAGAGCTGGAGTT | 52535935 | 52535951 | 17 | 0.121291 |
| 53 | 0.42220616 | GATGAGAGCTGGAGTTT | 52535936 | 52535952 | 17 | −0.0357 |
| 54 | 0.54186296 | ATGAGAGCTGGAGTTTA | 52535937 | 52535953 | 17 | 0.08396 |
| 55 | 0.75146207 | TGAGAGCTGGAGTTTAT | 52535938 | 52535954 | 17 | 0.293559 |
| 56 | 0.83250872 | GAGAGCTGGAGTTTATC | 52535939 | 52535955 | 17 | 0.374606 |
| 57 | 0.84600061 | AGAGCTGGAGTTTATCT | 52535940 | 52535956 | 17 | 0.388098 |
| 58 | 0.90189881 | GAGCTGGAGTTTATCTT | 52535941 | 52535957 | 17 | 0.443996 |
| 59 | 0.85045831 | AGCTGGAGTTTATCTTT | 52535942 | 52535958 | 17 | 0.392555 |
| 60 | 0.94235165 | GCTGGAGTTTATCTTTT | 52535943 | 52535959 | 17 | 0.484449 |
| 61 | 0.96260732 | CTGGAGTTTATCTTTTG | 52535944 | 52535960 | 17 | 0.504704 |
| 62 | 0.93743667 | TGGAGTTTATCTTTTGT | 52535945 | 52535961 | 17 | 0.479534 |
| 63 | 0.96488622 | GGAGTTTATCTTTTGTG | 52535946 | 52535962 | 17 | 0.506983 |
| 64 | 0.95897848 | GAGTTTATCTTTTGTGT | 52535947 | 52535963 | 17 | 0.501076 |
| 65 | 0.97370995 | AGTTTATCTTTTGTGTT | 52535948 | 52535964 | 17 | 0.515807 |
| 66 | 0.96669576 | GTTTATCTTTTGTGTTC | 52535949 | 52535965 | 17 | 0.508793 |
| 67 | 0.94990072 | TTTATCTTTTGTGTTCT | 52535950 | 52535966 | 17 | 0.491998 |
| 68 | 0.41427269 | AGATGAGAGCTGGAGTTT | 52535935 | 52535952 | 18 | −0.04363 |
| 69 | 0.29548406 | GATGAGAGCTGGAGTTTA | 52535936 | 52535953 | 18 | −0.16242 |
| 70 | 0.65272521 | ATGAGAGCTGGAGTTTAT | 52535937 | 52535954 | 18 | 0.194822 |
| 71 | 0.82775724 | TGAGAGCTGGAGTTTATC | 52535938 | 52535955 | 18 | 0.369854 |
| 72 | 0.89482076 | GAGAGCTGGAGTTTATCT | 52535939 | 52535956 | 18 | 0.436918 |
| 73 | 0.89873087 | AGAGCTGGAGTTTATCTT | 52535940 | 52535957 | 18 | 0.440828 |
| 74 | 0.93420851 | GAGCTGGAGTTTATCTTT | 52535941 | 52535958 | 18 | 0.476306 |
| 75 | 0.88748876 | AGCTGGAGTTTATCTTTT | 52535942 | 52535959 | 18 | 0.429586 |
| 76 | 0.95705511 | GCTGGAGTTTATCTTTTG | 52535943 | 52535960 | 18 | 0.499152 |
| 77 | 0.95710864 | CTGGAGTTTATCTTTTGT | 52535944 | 52535961 | 18 | 0.499206 |
| 78 | 0.95718201 | TGGAGTTTATCTTTTGTG | 52535945 | 52535962 | 18 | 0.499279 |
| 79 | 0.95723276 | GGAGTTTATCTTTTGTGT | 52535946 | 52535963 | 18 | 0.49933 |
| 80 | 0.9682069 | GAGTTTATCTTTTGTGTT | 52535947 | 52535964 | 18 | 0.510304 |
| 81 | 0.96703305 | AGTTTATCTTTTGTGTTC | 52535948 | 52535965 | 18 | 0.50913 |
| 82 | 0.89944316 | GTTTATCTTTTGTGTTCT | 52535949 | 52535966 | 18 | 0.44154 |
| 83 | 0.35701069 | AGATGAGAGCTGGAGTTTA | 52535935 | 52535953 | 19 | −0.10089 |
| 84 | 0.37085899 | GATGAGAGCTGGAGTTTAT | 52535936 | 52535954 | 19 | −0.08704 |
| 85 | 0.81174544 | ATGAGAGCTGGAGTTTATC | 52535937 | 52535955 | 19 | 0.353843 |
| 86 | 0.86312479 | TGAGAGCTGGAGTTTATCT | 52535938 | 52535956 | 19 | 0.405222 |

TABLE 2-continued

| SEQ ID NO | PSI | sequence | Start Chr13 [hg19/b37] | End Chr13 [hg19/b37] | length | dPSI |
|---|---|---|---|---|---|---|
| 87 | 0.92042588 | GAGAGCTGGAGTTTATCTT | 52535939 | 52535957 | 19 | 0.462523 |
| 88 | 0.94378406 | AGAGCTGGAGTTTATCTTT | 52535940 | 52535958 | 19 | 0.485881 |
| 89 | 0.90121758 | GAGCTGGAGTTTATCTTTT | 52535941 | 52535959 | 19 | 0.443315 |
| 90 | 0.97875323 | AGCTGGAGTTTATCTTTTG | 52535942 | 52535960 | 19 | 0.52085 |
| 91 | 0.97165722 | GCTGGAGTTTATCTTTTGT | 52535943 | 52535961 | 19 | 0.513754 |
| 92 | 0.974632 | CTGGAGTTTATCTTTTGTG | 52535944 | 52535962 | 19 | 0.516729 |
| 93 | 0.98143024 | TGGAGTTTATCTTTTGTGT | 52535945 | 52535963 | 19 | 0.523527 |
| 94 | 0.96598484 | GGAGTTTATCTTTTGTGTT | 52535946 | 52535964 | 19 | 0.508082 |
| 95 | 0.96947187 | GAGTTTATCTTTTGTGTTC | 52535947 | 52535965 | 19 | 0.511569 |
| 96 | 0.51215069 | AGTTTATCTTTTGTGTTCT | 52535948 | 52535966 | 19 | 0.054248 |
| 97 | 0.43801448 | GATGAGAGCTGGAGTTTATC | 52535936 | 52535955 | 20 | -0.01989 |
| 98 | 0.84294034 | ATGAGAGCTGGAGTTTATCT | 52535937 | 52535956 | 20 | 0.385037 |
| 99 | 0.91506349 | TGAGAGCTGGAGTTTATCTT | 52535938 | 52535957 | 20 | 0.457161 |
| 100 | 0.95571491 | GAGAGCTGGAGTTTATCHT | 52535939 | 52535958 | 20 | 0.497812 |
| 101 | 0.9250529 | AGAGCTGGAGTTTATCTTTT | 52535940 | 52535959 | 20 | 0.46715 |
| 102 | 0.91454039 | AGCTGGAGTTTATCTTTTGT | 52535942 | 52535961 | 20 | 0.456638 |
| 103 | 0.95584009 | GCTGGAGTTTATCTTTTGTG | 52535943 | 52535962 | 20 | 0.497937 |
| 104 | 0.96866415 | CTGGAGTTTATCTTTTGTGT | 52535944 | 52535963 | 20 | 0.510761 |
| 105 | 0.50424102 | GTTGGGCCCAGGTAGAGGAA | 52535908 | 52535927 | 20 | 0.046338 |
| 106 | 0.46400523 | GCAGAGTTGGGCCCAGGTAG | 52535903 | 52535922 | 20 | 0.006102 |
| 107 | 0.55283098 | AGCTGGCAGAGTTGGGCCCA | 52535898 | 52535917 | 20 | 0.094928 |
| 108 | 0.70816205 | AGACCAGCTGGCAGAGTTGG | 52535893 | 52535912 | 20 | 0.250259 |
| 109 | 0.44154369 | AGACAAGACCAGCTGGCAGA | 52535888 | 52535907 | 20 | -0.01636 |
| 110 | 0.44883783 | TGGGAAGAcAAGAcCAGCTG | 52535883 | 52535902 | 20 | -0.00907 |
| 111 | 0.25330097 | CACCATGGGAAGACAAGACC | 52535878 | 52535897 | 20 | -0.2046 |
| 112 | 0.1584088 | GAAGGCACCATGGGAAGACA | 52535873 | 52535892 | 20 | -0.29949 |
| 113 | 0.050187 | AGGAGGAAGGCACCATGGGA | 52535868 | 52535887 | 20 | -0.40772 |
| 114 | 0.05564216 | AATCCAGGAGGAAGGCACCA | 52535863 | 52535882 | 20 | -0.40226 |
| 115 | 0.0583237 | TGGTTAAAATATGCATTGGC | 52536095 | 52536114 | 20 | -0.39958 |
| 116 | 0.0814945 | AAAATATGCATTGGCAGAAA | 52536100 | 52536119 | 20 | -0.37641 |
| 117 | 0.18600916 | ATGCATTGGCAGAAAGCACT | 52536105 | 52536124 | 20 | -0.27189 |
| 118 | 0.2612183 | TTGGCAGAAAGCACTTTTCA | 52536110 | 52536129 | 20 | -0.19668 |
| 119 | 0.7320813 | AGAAAGCACTTTTCAGCTTT | 52536115 | 52536134 | 20 | 0.274178 |
| 120 | 0.92565362 | GCACTTTTCAGCTTTGGAAA | 52536120 | 52536139 | 20 | 0.467751 |
| 121 | 0.9502844 | TTTCAGCTTTGGAAATTAGA | 52536125 | 52536144 | 20 | 0.492382 |
| 122 | 0.96330809 | GCTTTGGAAATTAGAAAGTG | 52536130 | 52536149 | 20 | 0.505405 |
| 123 | 0.80993619 | GGAAATTAGAAAGTGAATCT | 52536135 | 52536154 | 20 | 0.352033 |
| 124 | 0.71516338 | TTAGAAAGTGAATCTAAAAG | 52536140 | 52536159 | 20 | 0.257261 |

TABLE 2-continued

| SEQ ID NO | PSI | sequence | Start Chr13 [hg19/b37] | End Chr13 [hg19/b37] | length | dPSI |
|---|---|---|---|---|---|---|
| 125 | 0.52494194 | GGTAGAGGAAGGGACTTA | 52535918 | 52535935 | 18 | 0.067039 |
| 126 | 0.6689587 | GTAGAGGAAGGGACTTAG | 52535919 | 52535936 | 18 | 0.211056 |
| 127 | 0.68622134 | TAGAGGAAGGGACTTAGA | 52535920 | 52535937 | 18 | 0.228319 |
| 128 | 0.78427472 | AGAGGAAGGGACTTAGAT | 52535921 | 52535938 | 18 | 0.326372 |
| 129 | 0.7981034 | GAGGAAGGGACTTAGATG | 52535922 | 52535939 | 18 | 0.340201 |
| 130 | 0.89063399 | AGGAAGGGACTTAGATGA | 52535923 | 52535940 | 18 | 0.432731 |
| 131 | 0.9141607 | GGAAGGGACTTAGATGAG | 52535924 | 52535941 | 18 | 0.456258 |
| 132 | 0.89012483 | GAAGGGACTTAGATGAGA | 52535925 | 52535942 | 18 | 0.432222 |
| 133 | 0.93330513 | AAGGGACTTAGATGAGAG | 52535926 | 52535943 | 18 | 0.475402 |
| 134 | 0.85689543 | AGGGACTTAGATGAGAGC | 52535927 | 52535944 | 18 | 0.398993 |
| 135 | 0.82924288 | GGGACTTAGATGAGAGCT | 52535928 | 52535945 | 18 | 0.37134 |
| 136 | 0.89801786 | GGACTTAGATGAGAGCTG | 52535929 | 52535946 | 18 | 0.440115 |
| 137 | 0.92780754 | GACTTAGATGAGAGCTGG | 52535930 | 52535947 | 18 | 0.469905 |
| 138 | 0.78670155 | ACTTAGATGAGAGCTGGA | 52535931 | 52535948 | 18 | 0.328799 |
| 139 | 0.85607847 | CTTAGATGAGAGCTGGAG | 52535932 | 52535949 | 18 | 0.398176 |
| 140 | 0.8755492 | TTAGATGAGAGCTGGAGT | 52535933 | 52535950 | 18 | 0.417646 |
| 141 | 0.81911248 | TAGATGAGAGCTGGAGTT | 52535934 | 52535951 | 18 | 0.36121 |
| 142 | 0.65870755 | GTAGAGGAAGGGACTTAGAT | 52535919 | 52535938 | 20 | 0.200805 |
| 143 | 0.68963137 | TAGAGGAAGGGACTTAGATG | 52535920 | 52535939 | 20 | 0.231729 |
| 144 | 0.71236425 | AGAGGAAGGGACTTAGATGA | 52535921 | 52535940 | 20 | 0.254461 |
| 145 | 0.77181564 | GAGGAAGGGACTTAGATGAG | 52535922 | 52535941 | 20 | 0.313913 |
| 146 | 0.91591182 | AGGAAGGGACTTAGATGAGA | 52535923 | 52535942 | 20 | 0.458009 |
| 147 | 0.93671833 | GAAGGGACTTAGATGAGAGC | 52535925 | 52535944 | 20 | 0.478815 |
| 148 | 0.9264989 | AAGGGACTTAGATGAGAGCT | 52535926 | 52535945 | 20 | 0.468596 |
| 149 | 0.96644251 | AGGGACTTAGATGAGAGCTG | 52535927 | 52535946 | 20 | 0.50854 |
| 150 | 0.9477045 | GGGACTTAGATGAGAGCTGG | 52535928 | 52535947 | 20 | 0.489802 |
| 151 | 0.88244294 | GGACTTAGATGAGAGCTGGA | 52535929 | 52535948 | 20 | 0.42454 |
| 152 | 0.82302381 | ACTTAGATGAGAGCTGGAGT | 52535931 | 52535950 | 20 | 0.365121 |
| 153 | 0.68879408 | CTTAGATGAGAGCTGGAGTT | 52535932 | 52535951 | 20 | 0.230891 |
| 154 | 0.61269452 | TTAGATGAGAGCTGGAGTTT | 52535933 | 52535952 | 20 | 0.154792 |
| 155 | 0.50052141 | TAGATGAGAGCTGGAGTTTA | 52535934 | 52535953 | 20 | 0.042619 |

Figure 4A:
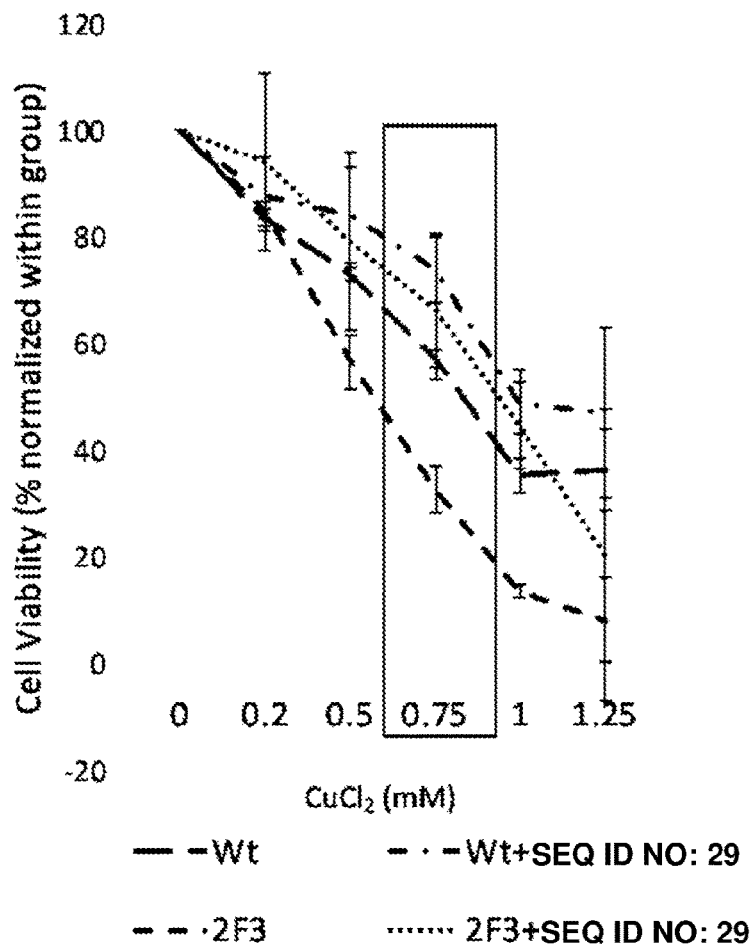
FIGS. 4A and 4B show recovery of copper tolerance and ATP7B protein levels upon treatment with a splice modulating antisense oligonucleotide having a sequence set forth in SEQ ID: 29.
Figure 4B:
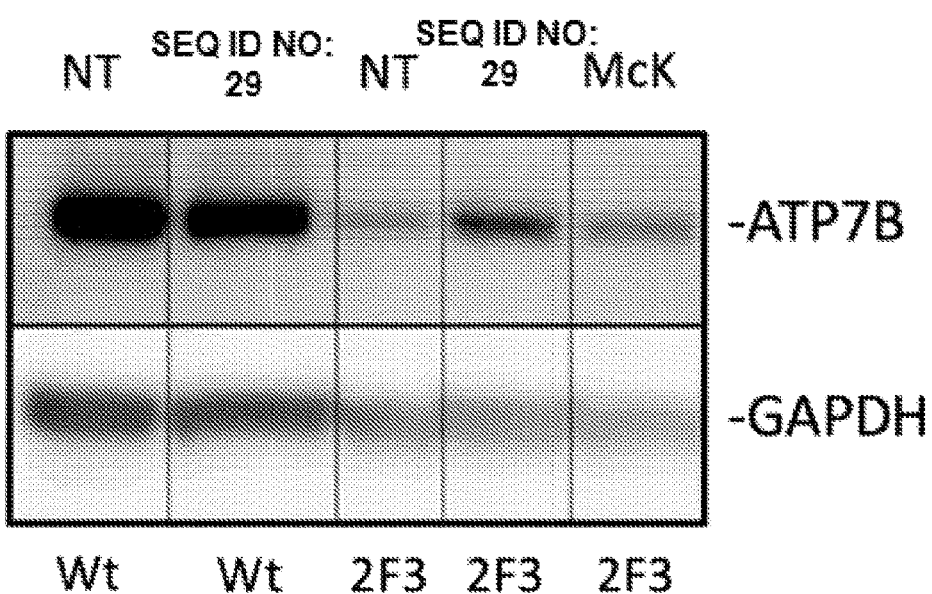

Example 4 Treatment of 2F3 Cells with a Splice Modulating Antisense Oligonucleotide Increases Protein Level and Copper Tolerance To model the effectiveness of an exon 6 inclusion inducing antisense oligonucleotide as a potential treatment for Wilson disease an in vitro copper sensitivity assay has been used. As seen in FIG. 4A, the M645R mutation reduces copper tolerance in 2F3 cells, mirroring Wilson disease where cells are unable to process copper as a result of ATP7B mutations. Transfection with an antisense oligonucleotide having the sequence set forth in SEQ ID 29 increases copper tolerance in 2F3 cells demonstrating that the copper sensitive phenotype can be at least partially rescued by transfection with an oligonucleotide shown herein to increase the inclusion of exon 6. Western blots against the ATP7B protein are consistent with these results, as 2F3 cells produce markedly less ATP7B protein than wild-type HepG2 cells (FIG. 4B). Transfection with an antisense oligonucleotide having the sequence set forth in SEQ ID 29 partially rescues this phenotype and increases ATP7B protein levels in 2F3 cells. This increase in ATP7B protein levels and function demonstrates that treatment with an antisense oligonucleotide known to increase the inclusion of exon 6 partially rescues the Wilson disease phenotype in an in vitro model.

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

What is claimed is:
1. An antisense oligonucleotide comprising 10 to 50 nucleotides with a nucleobase sequence at least 95% complementary over the entire length of the oligonucleotide to an ATPase copper transporting beta protein (ATP7B) pre-mRNA target sequence in exon 6, a 5'-flanking intron, a 3'-flanking intron, or a combination of exon 6 and the 5'-flanking or 3'-flanking intron;
wherein the antisense oligonucleotide comprises at least one modified nucleobase, at least one modified internucleoside linkage, or at least one modified sugar nucleoside, or wherein the antisense oligonucleotide is a morpholino oligomer; and
a) the ATP7B target sequence:
(i) comprises at least one nucleotide located among positions 54672-54680 or 54691-54701 in SEQ ID NO: 1, wherein the 5'-terminal nucleotide of the oligonucleotide is complementary to neither position 54695 nor position 54696 of SEQ ID NO: 1;
(ii) is located within the 5'-flanking intron among positions up to 54517 in SEQ ID NO: 1, the 5'-flanking intron among positions 54522 to 54581 in SEQ ID NO: 1 or the combination of the 5'-flanking intron and exon 6 among positions 54562 to 54593 in SEQ ID NO: 1; or
(iii) is located among positions 54631 to 54677 or 54655 to 54738 in SEQ ID NO: 1 or
b) the nucleobase sequence has at least 95% sequence identity to SEQ ID NO: 3, 4, 5, 6, 7, 8, 9, 10, 11, 22, 23, 24, 25, 28, 29, 30, 31, 32, 33, 34, 35, 36, 37, 38, 39, 40, 41, 42, 43, 44, 45, 46, 47, 48, 49, 50, 51, 52, 54, 55, 56, 57, 58, 59, 60, 61, 62, 63, 64, 65, 66, 67, 70, 71, 72, 73, 74, 75, 76, 77, 78, 79, 80, 81, 82, 85, 86, 87, 88, 89, 90, 91, 92, 93, 94, 95, 96, 98, 99, 100, 101, 102, 103, 104, 105, 106, 107, 108, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154 or 155.

2. The antisense oligonucleotide of claim 1, wherein the ATP7B target sequence comprises at least one nucleotide located among positions 54672-54680 or 54691-54701 in SEQ ID NO: 1, wherein the 5'-terminal nucleotide of the oligonucleotide is complementary to neither position 54695 nor position 54696 of SEQ ID NO: 1.

3. The antisense oligonucleotide of claim 1, wherein the ATP7B target sequence comprises at least one nucleotide located among positions 54492-54506 in SEQ ID NO: 1.

4. The antisense oligonucleotide of claim 1, wherein the ATP7B target sequence comprises at least one nucleotide located among positions 54472-54516, 54522-54593, and 54665-54718 in SEQ ID NO: 1.

5. The antisense oligonucleotide of claim 1, wherein the nucleobase sequence is complementary to a sequence within the 5'-flanking intron.

6. The antisense oligonucleotide of claim 1, wherein the ATP7B target sequence is located within the 5'-flanking intron among positions up to 54517 in SEQ ID NO: 1.

7. The antisense oligonucleotide of claim 1, wherein the nucleobase sequence has at least 95% sequence identity to SEQ ID NO: 3, 4, 5, 6, 7, 8, 9, 10, 11, 22, 23, 24, 25, 28, 29, 30, 31, 32, 33, 34, 35, 36, 37, 38, 39, 40, 41, 42, 43, 44, 45, 46, 47, 48, 49, 50, 51, 52, 54, 55, 56, 57, 58, 59, 60, 61, 62, 63, 64, 65, 66, 67, 70, 71, 72, 73, 74, 75, 76, 77, 78, 79, 80, 81, 82, 85, 86, 87, 88, 89, 90, 91, 92, 93, 94, 95, 96, 98, 99, 100, 101, 102, 103, 104, 105, 106, 107, 108, 119, 120, 121, 122, 123, of 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, or 155.

8. The antisense oligonucleotide of claim 1, wherein the ATP7B target sequence is located within: the 5'-flanking intron among positions 54522 to 54581 in SEQ ID NO: 1; or the combination of the 5'-flanking intron and exon 6 among positions 54562 to 54593 in SEQ ID NO: 1.

9. The antisense oligonucleotide of claim 1, wherein the ATP7B target sequence is located among positions 54631 to 54677 or 54655 to 54738 in SEQ ID NO: 1.

10. The antisense oligonucleotide of claim 1, wherein the antisense oligonucleotide comprises at least one modified nucleobase.

11. The antisense oligonucleotide of claim 1, wherein the antisense oligonucleotide comprises at least one modified internucleoside linkage.

12. The antisense oligonucleotide of claim 11, wherein at least 50% of internucleoside linkages in the antisense oligonucleotide are independently the modified internucleoside linkage.

13. The antisense oligonucleotide of claim 1, wherein the antisense oligonucleotide comprises at least one modified sugar nucleoside.

14. The antisense oligonucleotide of claim 13, wherein at least one modified sugar nucleoside is a bridged nucleic acid.

15. The antisense oligonucleotide of claim 13, wherein all nucleosides in the antisense oligonucleotide are independently the modified sugar nucleosides.

16. The antisense oligonucleotide of claim 1, wherein the antisense oligonucleotide is a morpholino oligomer.

17. The antisense oligonucleotide of claim 1, further comprising a targeting moiety.

18. The antisense oligonucleotide of claim 17, wherein: the targeting moiety is covalently conjugated at the 5'-terminus of the antisense oligonucleotide; or the targeting moiety is covalently conjugated at the 3'-terminus of the antisense oligonucleotide; or the targeting moiety is covalently conjugated at an internucleoside linkage of the antisense oligonucleotide.

19. The antisense oligonucleotide of claim 18, wherein the targeting moiety is covalently conjugated through a linker.

20. The antisense oligonucleotide of claim 19, wherein the linker is a cleavable linker.

21. The antisense oligonucleotide of claim 1, wherein the antisense oligonucleotide comprises 12 to 30 nucleosides.

22. The antisense oligonucleotide of claim 1, wherein the nucleobase sequence is as set forth in SEQ ID NO: 29.

23. The antisense oligonucleotide of claim 1, wherein the antisense oligonucleotide is modulatory for ATP7B variant splicing to yield an increase in exon 6 inclusion.

24. A pharmaceutical composition comprising the antisense oligonucleotide of claim 1 and a pharmaceutically acceptable excipient.

25. A method of increasing the level of exon 6-containing ATP7B mRNA molecules in a cell expressing an aberrant ATP7B gene, the method comprising contacting the cell with the antisense oligonucleotide of claim 1.

26. A method of treating Wilson disease in a subject having an aberrant ATP7B gene, the method comprising administering a therapeutically effective amount of the antisense oligonucleotide of claim 1 to the subject in need thereof.

27. The method of claim 26, wherein the aberrant ATP7B gene is ATP7B having a g·54646T>G mutation in SEQ ID NO: 1.

28. The method of claim 26, wherein the antisense oligonucleotide comprises the nucleobase sequence as set forth in SEQ ID NO: 29 and further comprises a targeting moiety, wherein the targeting moiety comprises N-acetylgalactosamine.

* * * * *